US010781183B2

(12) United States Patent
Neamati et al.

(10) Patent No.: US 10,781,183 B2
(45) Date of Patent: Sep. 22, 2020

(54) SMALL MOLECULE INDUCERS OF REACTIVE OXYGEN SPECIES AND INHIBITORS OF MITOCHONDRIAL ACTIVITY

(71) Applicants: The Regents of the University of Michigan, Ann Arbor, MI (US); UNIVERSITÀ DEGLI STUDI DI SASSARI, Sassari (IT)

(72) Inventors: Nouri Neamati, Ann Arbor, MI (US); Mario Sechi, Sassari (IT)

(73) Assignees: The Regents of the University of Michigan, Ann Arbor, MI (US); UNIVERSITA DEGLI STUDI DI SASSARI, Sassari (IT)

( * ) Notice: Subject to any disclaimer, the term of this patent is extended or adjusted under 35 U.S.C. 154(b) by 0 days.

(21) Appl. No.: 16/083,376

(22) PCT Filed: Mar. 7, 2017

(86) PCT No.: PCT/US2017/021150
§ 371 (c)(1),
(2) Date: Sep. 7, 2018

(87) PCT Pub. No.: WO2017/155991
PCT Pub. Date: Sep. 14, 2017

(65) Prior Publication Data
US 2019/0308942 A1  Oct. 10, 2019

Related U.S. Application Data

(60) Provisional application No. 62/305,367, filed on Mar. 8, 2016.

(51) Int. Cl.
*C07D 239/74* (2006.01)
*A61P 35/00* (2006.01)
*C07D 401/12* (2006.01)
*C07D 403/12* (2006.01)
*C07D 405/12* (2006.01)
*C07D 413/12* (2006.01)
*C07D 417/12* (2006.01)
*C07D 471/04* (2006.01)
*A61K 31/5377* (2006.01)
*A61K 45/06* (2006.01)
*A61K 31/517* (2006.01)

(52) U.S. Cl.
CPC .......... *C07D 239/74* (2013.01); *A61K 31/517* (2013.01); *A61K 31/5377* (2013.01); *A61K 45/06* (2013.01); *A61P 35/00* (2018.01); *C07D 401/12* (2013.01); *C07D 403/12* (2013.01); *C07D 405/12* (2013.01); *C07D 413/12* (2013.01); *C07D 417/12* (2013.01); *C07D 471/04* (2013.01)

(58) Field of Classification Search
CPC .................................................. C07D 239/74
See application file for complete search history.

(56) References Cited

U.S. PATENT DOCUMENTS 5,712,289 A    1/1998  Behforouz et al.

FOREIGN PATENT DOCUMENTS

| EP | 0107367 B1 | 5/1984 |
| WO | WO 97/21432 | 6/1997 |
| WO | WO9721432 | * 6/1997 |
| WO | WO 2004/022059 | 3/2004 |

OTHER PUBLICATIONS

Pinedo et al. (2000).*
McMahon et al. (2000).*
Pathania Divya et al., British Journal of Pharmacology (2015), 172(1), 50-63.*
Vippagunta et al. (2001).*
Alam, J., et al. Nrf2, a Cap'n'Collar transcription factor, regulates induction of the heme oxygenase-1 gene. J Biol Chem. Sep. 10, 1999;274(37):26071-8.
Alexeyev, M., et al., The maintenance of mitochondrial DNA integrity—critical analysis and update. Cold Spring Harb Perspect Biol. May 1, 2013;5(5):a012641.
Ali, S., et al., Differentially expressed miRNAs in the plasma may provide a molecular signature for aggressive pancreatic cancer. Am J Transl Res. Sep. 28, 2010;3(1):28-47.
Arlt, A., et al., Inhibition of the Nrf2 transcription factor by the alkaloid trigonelline renders pancreatic cancer cells more susceptible to apoptosis through decreased proteasomal gene expression and proteasome activity. Oncogene. Oct. 2013;32(40):4825-35.
Choi, A. M. et al., Heme oxygenase-1: function, regulation, and implication of a novel stress-inducible protein in oxidant-induced lung injury. Am J Respir Cell Mol Biol. Jul. 1996;15(1):9-19.
Choi, E.K. et al., Upregulation of NAD(P)H:Quinone Oxidoreductase by Radiation Potentiates the Effect of Bioreductive Betta-Lapachone on Cancer Cells. Neoplasia, vol. 9, No. 8, Aug. 2007, pp. 634-642; abstract; p. 643, col. 2, paragraph 2.
Cohen, S. J., et al., A phase I study of imexon plus gemcitabine as first-line therapy for advanced pancreatic cancer. Cancer Chemother Pharmacol. Jul. 2010;66(2):287-94.
Conroy, T., et al., Folfirinox versus gemcitabine for metastatic pancreatic cancer. N Engl J Med. May 12, 2011;364(19):1817-25.
Denicola, G. M., et al., Oncogene-induced Nrf2 transcription promotes ROS detoxification and tumorigenesis. Nature. Jul. 6, 2011;475(7354):106-9.

(Continued)

*Primary Examiner* — Paul V Ward
(74) *Attorney, Agent, or Firm* — Casimir Jones, SC; Robert A. Goetz

(57) ABSTRACT

This invention is in the field of medicinal chemistry. In particular, the invention relates to a new class of small-molecules having a quinazolinedione structure which function as reactive oxygen species (ROS) inducers and inhibitors of mitochondrial activity within cancer cells (e.g., pancreatic cancer cells), and their use as therapeutics for the treatment of cancer (e.g., pancreatic cancer) and other diseases.

9 Claims, 18 Drawing Sheets

(56) References Cited

OTHER PUBLICATIONS

Dhillon, H., et al., Piperlongumine induces pancreatic cancer cell death by enhancing reactive oxygen species and DNA damage. Toxicol Rep. 2014;1:309-318.

Dinkova-Kostova, A. T. et al., Persuasive evidence that quinone reductase type 1 (DT diaphorase) protects cells against the toxicity of electrophiles and reactive forms of oxygen. Free Radic Biol Med. Aug. 2000;29(3-4):231-40.

Dinkova-Kostova, A. T., et al., Direct evidence that sulfhydryl groups of Keap1 are the sensors regulating induction of phase 2 enzymes that protect against carcinogens and oxidants. Proc Natl Acad Sci U S A. Sep. 3, 2002;99(18):11908-13.

Dorr, R. T., et al., Induction of apoptosis and cell cycle arrest by imexon in human pancreatic cancer cell lines. Int J Gastrointest Cancer. 2005;36(1):15-28.

Falkenberg, M., et al., DNA replication and transcription in mammalian mitochondria. Annu Rev Biochem. 2007;76:679-99.

Fruehauf, J. P. et al., Reactive oxygen species: a breath of life or death? Clin Cancer Res. Feb. 1, 2007;13(3):789-94.

Guleng, G., et al., Mitochondrial microsatellite instability in colorectal carcinomas—frequency and association with nuclear microsatellite instability. Cancer Lett. Feb. 28, 2005;219(1):97-103.

Halliwell, B. et al., DNA damage by oxygen-derived species. Its mechanism and measurement in mammalian systems. FEBS Lett. Apr. 9, 1991;281(1-2):9-19.

Harding, H. P., et al., Perk is essential for translational regulation and cell survival during the unfolded protein response. Mol Cell. May 2000; 5(5):897-904.

Hayes, J. D. et al., NRF2 and KEAP1 mutations: permanent activation of an adaptive response in cancer. Trends Biochem Sci. Apr. 2009; 34(4):176-88.

Haze, K., et al., Mammalian transcription factor ATF6 is synthesized as a transmembrane protein and activated by proteolysis in response to endoplasmic reticulum stress. Mol Biol Cell. Nov. 1999;10(11):3787-99.

Hetz, C. The unfolded protein response: controlling cell fate decisions under ER stress and beyond. Nat Rev Mol Cell Biol. Jan. 18, 2012;13(2):89-102.

Jaiswal, A. K. Nrf2 signaling in coordinated activation of antioxidant gene expression. Free Radic Biol Med. May 15, 200;36(10):1199-207.

Kabekkodu, S. P., et al., Mitochondrial DNA variation analysis in cervical cancer. Mitochondrion. May 2014;16:73-82.

Kim, B.W. et al. Mitochondrial oxidative phosphorylation system is recruited to detergent-resistant lipid rafts during myogenesis, Proteomics, vol. 10, 2010, pp. 2498-2515; abstract.

Kim, R., et al., Role of the unfolded protein response in cell death. Apoptosis. Jan. 2006;11(1):5-13.

Kong, B., et al., Overview on how oncogenic Kras promotes pancreatic carcinogenesis by inducing low intracellular ROS levels. Front Physiol. Sep. 12, 2013;4:246.

Lee, Y.C. et al., Contribution of Vascular Endolthelial Growth Factor to Airway Hyperresponsiveness and Inflammation in a Murine Model of Toluene Diisocyante-Induced Asthma, The Journal of Immunology, vol. 168, 2002, pp. 3595-3600; abstract.

Li, X., et al., Targeting mitochondrial reactive oxygen species as novel therapy for inflammatory diseases and cancers. J Hematol Oncol. Feb. 25, 2013;6:19.

Lievre, A., et al., Clinical value of mitochondrial mutations in colorectal cancer. J Clin Oncol. May 20, 2005;23(15):3517-25.

Lister, A., et al. Nrf2 is overexpressed in pancreatic cancer: implications for cell proliferation and therapy. Mol Cancer. Apr. 13, 2011;10:37.

Malhotra, J. D. et al., Endoplasmic reticulum stress and oxidative stress: a vicious cycle or a double-edged sword? Antioxid Redox Signal. Dec. 2007;9(12):2277-93.

Montoya, J., et al., The pattern of transcription of the human mitochondrial rRNA genes reveals two overlapping transcription units. Cell. Aug. 1983;34(1):151-9.

Moon, E. J. et al., Dual roles of NRF2 in tumor prevention and progression: Possible implications in cancer treatment. Free Radic Biol Med. Feb. 2015;79:292-9.

Mootha, V. K., et al., PGC-1alpha-responsive genes involved in oxidative phosphorylation are coordinately downregulated in human diabetes. Nat Genet. Jul. 2003;34(3):267-73.

Na, H. K. et al., Oncogenic potential of Nrf2 and its principal target protein heme oxygenase-1. Free Radic Biol Med. Feb. 2014;67:353-65.

Nioi, P., et al, Identification of a novel Nrf2-regulated antioxidant response element (ARE) in the mouse NAD(P)H:quinone oxidoreductase 1 gene: reassessment of the ARE consensus sequence. Biochem J. Sep. 1, 2003;374(Pt 2):337-48.

Nishitoh, H. CHOP is a multifunctional transcription factor in the ER stress response. J Biochem. Mar. 2012;151(3):217-9.

Ojala, D. et al., tRNA punctuation model of RNA processing in human mitochondria. Nature. Apr. 9, 1981;290(5806):470-4.

Ouyang, H., et al., Immortal human pancreatic duct epithelial cell lines with near normal genotype and phenotype. Am J Pathol. Nov. 2000;157(5):1623-31.

Oyadomari, S. et al., Roles of CHOP/GADD153 in endoplasmic reticulum stress. Cell Death Differ. Apr. 2004;11(4):381-9.

Pathania, D., et al., Mechanisms underlying the cytotoxicity of a novel quinazolinedione-based redox modulator, QD232, in pancreatic cancer cells. Br J Pharmacol. Jan. 2015;172(1):50-63.

Pathania, D., et al., Design and discovery of novel quinazolinedione-based redox modulators as therapies for pancreatic cancer. Biochim Biophys Acta. Jan. 2014;1840(1):332-43.

Paulsen, M. T., et al., Use of Bru-Seq and BruChase-Seq for genome-wide assessment of the synthesis and stability of RNA. Methods. May 1, 2014;67(1):45-54.

Paulsen, M. T., et al., Coordinated regulation of synthesis and stability of RNA during the acute TNF-induced proinflammatory response. Proc Natl Acad Sci U S A. Feb. 5, 2013;110(6):2240-5.

Pelicano, H. et al. ROS stress in cancer cells and therapeutic implications. Drug Resist Updat. Apr. 2004;7(2):97-110.

Ross, D.,et al., NAD(P)H:quinone oxidoreductase 1 (NQO1): chemoprotection, bioactivation, gene regulation and genetic polymorphisms. Chem Biol Interact. Dec. 1, 2000;129(1-2):77-97.

Ryan, D. P., et al., Pancreatic adenocarcinoma. N Engl J Med. Sep. 11, 2014;371(11):1039-49.

Sabharwal, S. S. et al., Mitochondrial ROS in cancer: initiators, amplifiers or an Achilles' heel? Nat Rev Cancer. Nov. 2014;14(11):709-21.

Salazar, J. J. et al., Preferential mitochondrial DNA injury caused by glucose oxidase as a steady generator of hydrogen peroxide in human fibroblasts. Mutat Res. Nov. 1997;385(2):139-49.

Schroder, M. et al., The Mammalian Unfolded Protein Reponse. Annual Review in Biochemistry, vol. 74, 2005, pp. 739-789, figure 1, figure 1 legend; p. 758, figure 4; p. 759, figure 4 legend.

Shamu, C. E. et al., Oligomerization and phosphorylation of the Ire1p kinase during intracellular signaling from the endoplasmic reticulum to the nucleus. EMBO J. Jun. 17, 1996;15(12):3028-39.

Shokolenko, I. N., et al., Persistent damage induces mitochondrial DNA degradation. DNA Repair (Amst). Jul. 2013;12(7):488-99.

Siegel, R., et al., Cancer statistics, 2014. CA Cancer J Clin. Jan.-Feb. 2014;64(1):9-29.

Subramanian, A., et al., Gene set enrichment analysis: a knowledge-based approach for interpreting genome-wide expression profiles. Proc Natl Acad Sci U S A. Oct. 25, 2005;102(43):15545-50.

Suzuki, M., et al., Alterations in the mitochondrial displacement loop in lung cancers. Clin Cancer Res. Nov. 15, 2003;9(15):5636-41.

Vadrot, N., et al., Mitochondrial DNA maintenance is regulated in human hepatoma cells by glycogen synthase kinase 3beta and p53 in response to tumor necrosis factor alpha. PLoS One. 2012;7(7):e40879.

Verfaillie, T., et al., Targeting ER stress induced apoptosis and inflammation in cancer. Cancer Lett. May 28, 2013;332(2):249-64.

Von Hoff, D. D., et al., Increased survival in pancreatic cancer with nab-paclitaxel plus gemcitabine. N Engl J Med. Oct. 31, 2013;369(18):1691-703.

(56) References Cited

OTHER PUBLICATIONS

Wheelhouse, N. M., et al., Mitochondrial D-loop mutations and deletion profiles of cancerous and noncancerous liver tissue in hepatitis B virus-infected liver. Br J Cancer. Apr. 11, 2005;92(7):1268-72.

Yakes, F. M. et al., Mitochondrial DNA damage is more extensive and persists longer than nuclear DNA damage in human cells following oxidative stress. Proc Natl Acad Sci U S A. Jan. 21, 1997;94(2):514-9.

Ye, K., et al., Extensive pathogenicity of mitochondrial heteroplasmy in healthy human individuals. Proc Natl Acad Sci U S A. Jul. 22, 2014;111(29):10654-9.

Zhang, D. D. et al., Distinct cysteine residues in Keap1 are required for Keap1-dependent ubiquitination of Nrf2 and for stabilization of Nrf2 by chemopreventive agents and oxidative stress. Mol Cell Biol. Nov. 2003;23(22):8137-51.

\* cited by examiner

SMALL MOLECULE INDUCERS OF REACTIVE OXYGEN SPECIES AND INHIBITORS OF MITOCHONDRIAL ACTIVITY

CROSS-REFERENCE TO RELATED APPLICATIONS

This application is a Section 371 U.S. national stage entry of International Patent Application No. PCT/US2017/021150, International Filing Date Mar. 7, 2017 which claims priority to and the benefit of U.S. Provisional Application No. 62/305,367, filed Mar. 8, 2016, which are hereby incorporated by reference in their entireties.

STATEMENT REGARDING FEDERALLY SPONSORED RESEARCH OR DEVELOPMENT

This invention was made with government support under CA188252 awarded by the National Institutes of Health. The Government has certain rights in the invention.

FIELD OF THE INVENTION

This invention is in the field of medicinal chemistry. In particular, the invention relates to a new class of small-molecules having a quinazolinedione structure which function as reactive oxygen species (ROS) inducers and inhibitors of mitochondrial activity within cancer cells (e.g., pancreatic cancer cells), and their use as therapeutics for the treatment of cancer (e.g., pancreatic cancer) and other diseases.

INTRODUCTION

Pancreatic cancer is the fourth leading cause of cancer related death in both genders in the United States, claiming 39590 lives in 2014 alone (Siegel et al., 2014). Given its asymptomatic and metastatic nature, over 50% of pancreatic cancer cases are diagnosed at late stages, when the tumor has metastasized and is unresectable. Therefore, treatment of pancreatic cancer is largely dependent on systemic chemotherapy. Ever since its approval by the FDA in 1996, gemcitabine-based regimes have been the standard of care for pancreatic cancer (Ryan et al., 2014). However, limited by late-stage diagnosis and inherent/acquired resistance to current chemotherapy, the overall five-year survival rate of pancreatic cancer is only 6.7%, one of the lowest among all types of cancers. Recently, two combination regimens with modest clinical activity have been added to the options. The addition of nab-paclitaxel (albumin-bound paclitaxel) to gemcitabine increased median overall survival from 6.7 to 8.5 months (Von Hoff et al., 2013). The combination FOLFIRINOX (oxaliplatin, irinotecan, fluorouracil and leucovorin) was approved for the treatment of metastatic pancreatic cancer by increasing median overall survival from 6.8 months in the gemcitabine group to 11.1 months in the FOLFIRINOX group (Conroy et al., 2011) but increased toxicity is the major concern for these new treatment options.

Therefore, novel therapeutics is urgently needed to enhance the survival of patients with this devastating disease.

SUMMARY OF THE INVENTION

Altered redox homeostasis in cancer cells provides a new opportunity for tumor intervention. Reactive oxygen species (ROS), a natural byproduct from mitochondrial respiration, play an important role as second messengers in cell signaling (Li et al., 2013). However, when present at high concentrations, ROS can be detrimental to cellular processes, inducing damage to DNA, lipids and proteins by oxidation. Therefore, excessive intracellular ROS are constantly eliminated by antioxidants regulated by the ROS-detoxifying machinery to ensure a healthy redox state. In tumor cells, antioxidant enzymes are often active as a result of elevated levels of intrinsic ROS (Fruehauf and Meyskens, 2007). Oncogenic mutations like $Kras^{G12D}$, commonly present in pancreatic ductal adenocarcinoma (PDAC), activate the master antioxidant switch Nrf2 in the basal state (DeNicola et al., 2011, Kong et al., 2013). Altered redox homeostasis in tumors make them more susceptible to induced oxidative stress that overwhelms their adaptive antioxidant capacity and triggers ROS-mediated cell death (Pelicano et al., 2004, Sabharwal and Schumacker, 2014).

Previously, it was shown that the quinazolinedione QD232 exerts ROS-dependent cytotoxicity in pancreatic cancer models (Pathania et al., 2015, Pathania et al., 2014). Experiments conducted during the course of developing embodiments for the present invention performed a lead optimization campaign and identified QD325

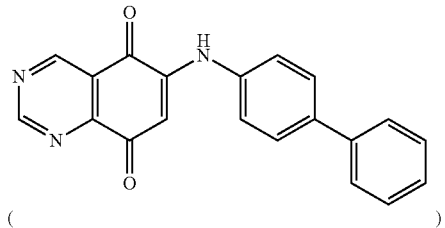 [SMILES: O=C1C(Nc2ccc(-c3ccccc3)cc2)=CC(=O)c2ncncc21]

as a lead compound for in-depth preclinical and mechanistic studies. Such experiments demonstrate that selective inhibition of the mitochondrial D-loop can be efficacious and be further explored as innovative therapeutic approach to target cancers that heavily depend on mitochondrial function.

As such, the present invention provides a new class of small-molecules having a quinazolinedione structure which function as ROS inducers and inhibitors of mitochondrial function, and as therapeutics for the treatment of cancer (e.g., pancreatic cancer) (e.g., any type of cancer) and other diseases.

Accordingly, the present invention contemplates that exposure of animals (e.g., humans) suffering from cancer (e.g., pancreatic cancer) (e.g., PDAC) (e.g., and/or cancer related disorders) (e.g., any type of cancer) to therapeutically effective amounts of drug(s) having a quinazolinedione structure (e.g., small molecules having a quinazolinedione structure) that induce ROS and inhibit mitochondrial activity will inhibit the growth of cancer cells (e.g., PDAC cells) (e.g., any type of cancer) and/or supporting cells outright and/or render such cells as a population more susceptible to the cell death-inducing activity of cancer therapeutic drugs or radiation therapies.

In some embodiments, the inhibition of mitochondrial activity occurs through, for example, activating Nrf2-mediated oxidative stress and unfolded protein responses. For example, in some embodiments, such activating of Nrf2-mediated oxidative stress and unfolded protein responses occurs through increased nascent RNA synthesis of representative genes NQO1, HMOX1, DDIT3 and HSPA5.

In some embodiments, the inhibition of mitochondrial activity occurs through, for example, inhibiting synthesis of mtDNA transcripts and downregulating mtDNA-encoded OXPHOS enzyme.

The present invention contemplates that inhibitors of mitochondrial activity in PDAC cells satisfy an unmet need for the treatment of PDAC, either when administered as monotherapy to induce cell growth inhibition, apoptosis and/or cell cycle arrest in such cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent produces a greater tumor response and clinical benefit in such animals compared to those treated with the compound or anticancer drugs/radiation alone. Since the doses for all approved anticancer drugs and radiation treatments are known, the present invention contemplates the various combinations of them with the present compounds.

The Applicants have found that certain quinazolinedione compounds function as ROS-inducers and inhibitors of mitochondrial activity, and serve as therapeutics for the treatment of cancer (e.g., PDAC) and other diseases. Thus, the present invention relates to quinazolinedione compounds useful for inducing ROS, inhibiting mitochondrial activity (e.g., thereby facilitating cell apoptosis), and increasing the sensitivity of cells to inducers of apoptosis and/or cell cycle arrest.

Certain quinazolinedione compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, quinazolinedione compounds encompassed within Formula I are provided:

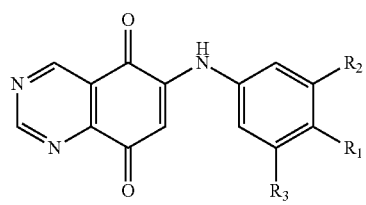

(Formula I)

or

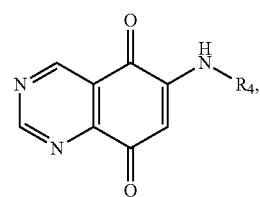

(Formula II)

including pharmaceutically acceptable salts, solvates, and/or prodrugs thereof.

Formula I is not limited to a particular chemical moiety for $R_1$, $R_2$, and $R_3$. Formula II is not limited to a particular chemical moiety for $R_4$.

In some embodiments, the particular chemical moiety for $R_1$, $R_2$, and $R_3$ independently include any chemical moiety that permits the resulting compound to induce ROS and inhibit mitochondrial activity within cancer cells. In some embodiments, the particular chemical moiety for $R_4$ includes any chemical moiety that permits the resulting compound to induce ROS and inhibit mitochondrial activity within cancer cells.

In some embodiments, the particular chemical moiety for $R_1$, $R_2$, and $R_3$ independently include any chemical moiety that permits the resulting compound to induce ROS and inhibit mitochondrial activity within cancer cells through activating Nrf2-mediated oxidative stress and unfolded protein responses (e.g., through increased nascent RNA synthesis of representative genes NQO1, HMOX1, DDIT3 and HSPA5). In some embodiments, the particular chemical moiety for $R_4$ includes any chemical moiety that permits the resulting compound to induce ROS and inhibit mitochondrial activity within cancer cells through activating Nrf2-mediated oxidative stress and unfolded protein responses (e.g., through increased nascent RNA synthesis of representative genes NQO1, HMOX1, DDIT3 and HSPA5).

In some embodiments, the particular chemical moiety for $R_1$, $R_2$, and $R_3$ independently include any chemical moiety that permits the resulting compound to induce ROS and inhibit mitochondrial activity occurs through, for example, inhibiting synthesis of mtDNA transcripts and downregulating mtDNA-encoded OXPHOS enzyme. In some embodiments, the particular chemical moiety for $R_4$ includes any chemical moiety that permits the resulting compound to induce ROS and inhibit mitochondrial activity occurs through, for example, inhibiting synthesis of mtDNA transcripts and downregulating mtDNA-encoded OXPHOS enzyme.

In some embodiments, $R_1$ is a chemical moiety selected from Hydrogen,

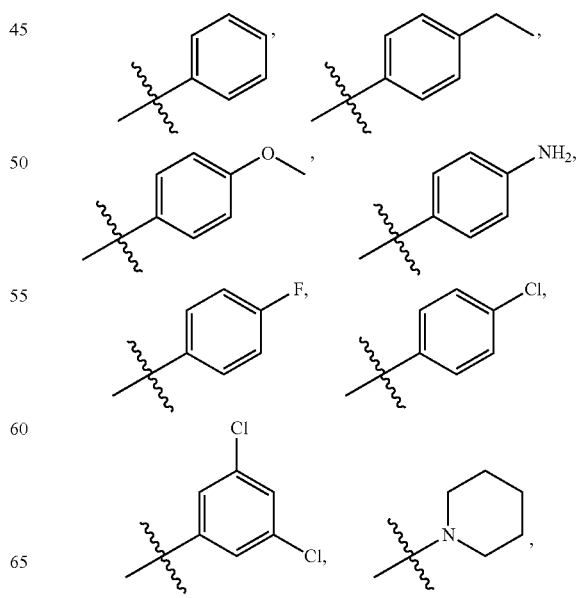

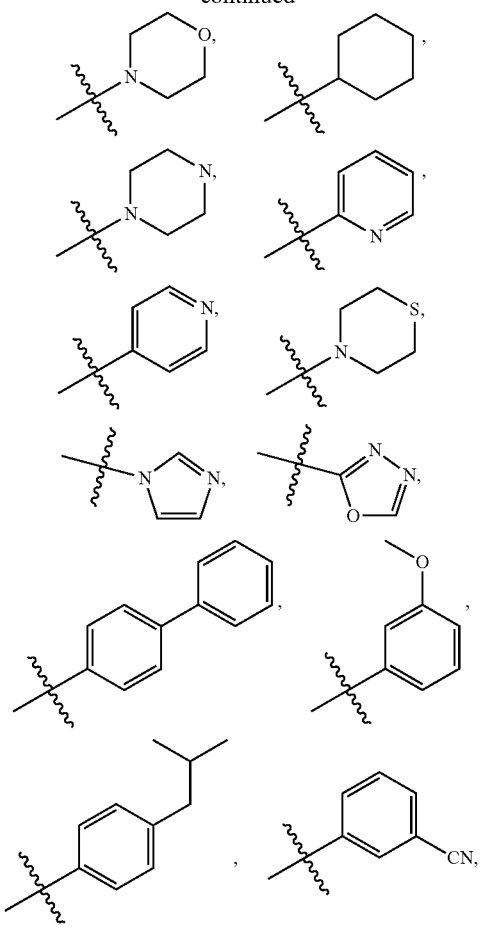
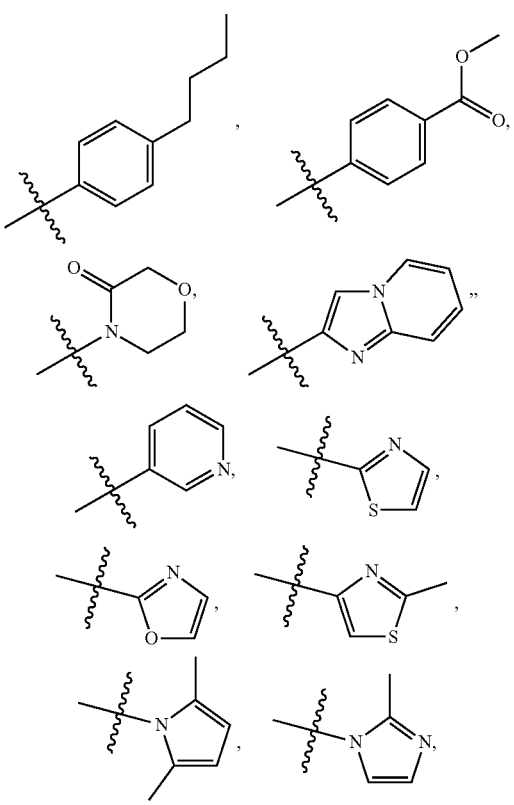
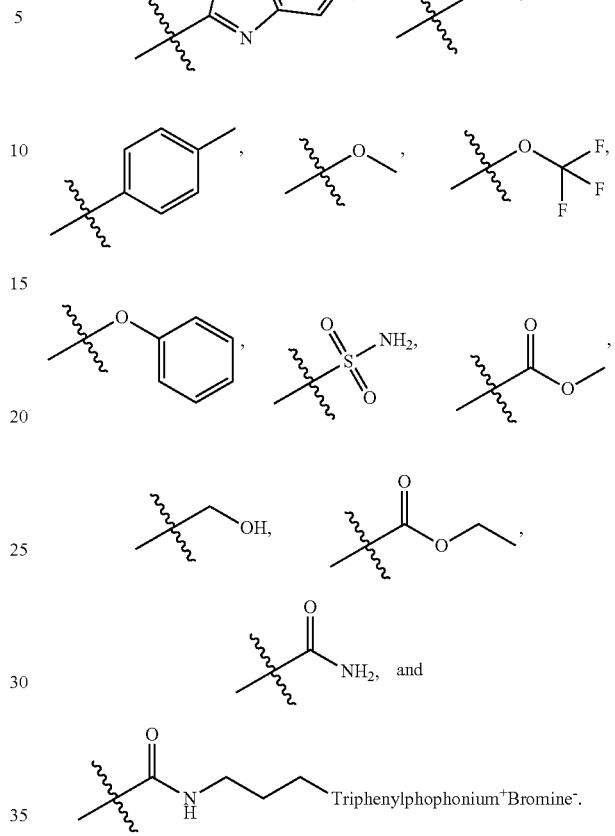
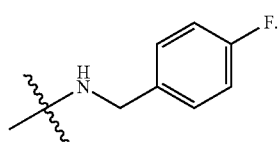 [SMILES: *NCc1ccc(F)cc1]
In some embodiments, $R_2$ is a chemical moiety selected from Hydrogen,
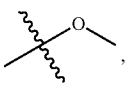
Fluorine, and
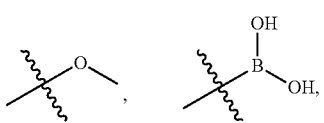
In some embodiments, $R_3$ is a chemical moiety selected from Hydrogen,
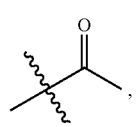

Fluorine, and
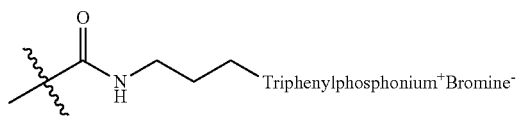
In some embodiments, R4 is a chemical moiety selected from Hydrogen,
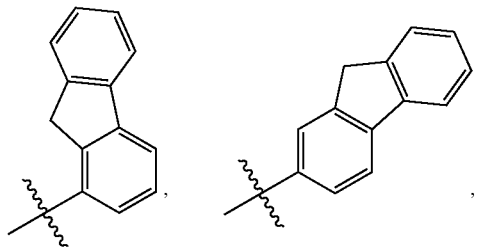
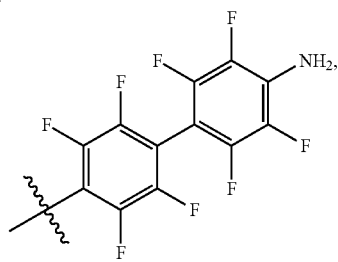
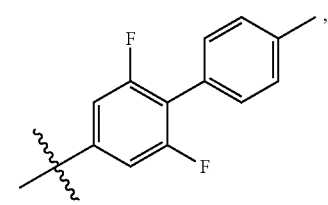
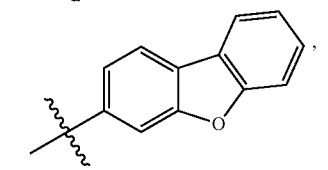
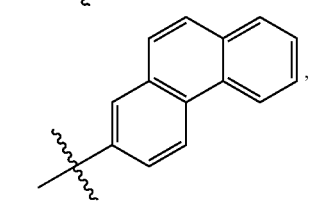
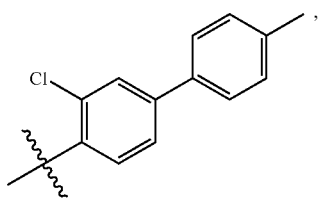
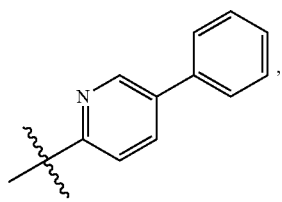
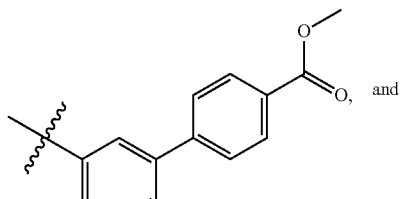
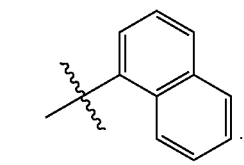
In some embodiments, the following compounds are contemplated for Formula I or Formula II:
(325)
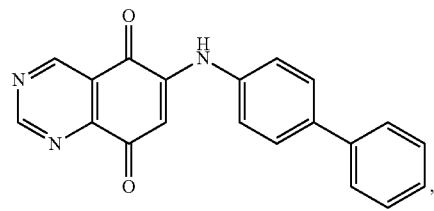
(356)
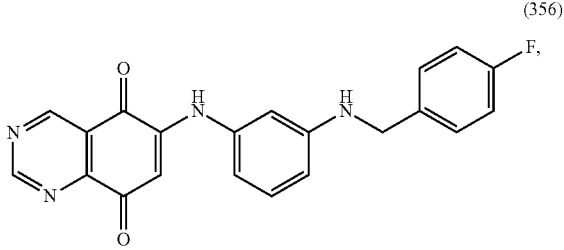
(335)
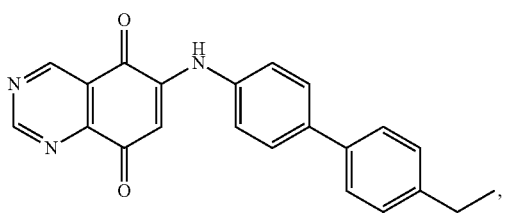

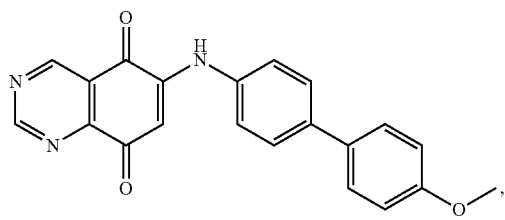
(336)
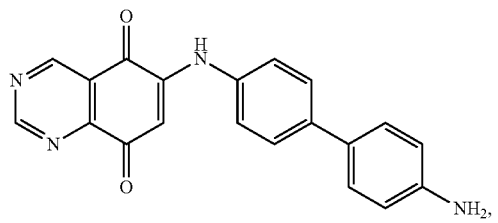
(337)
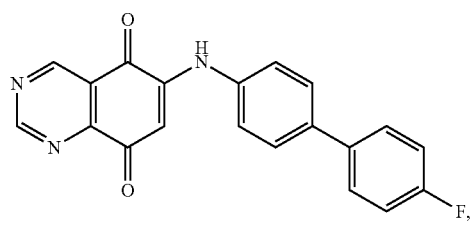
(334)
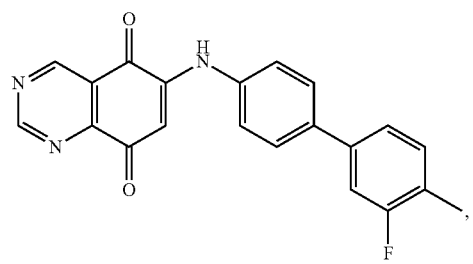
(338)
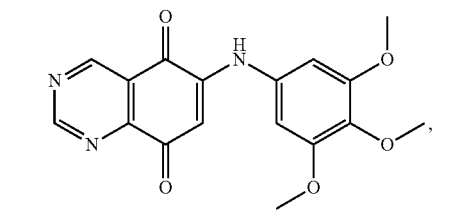
(326)
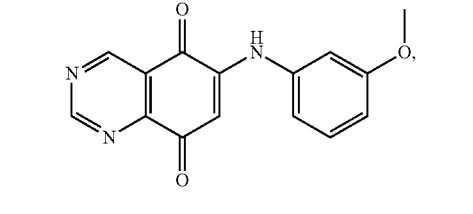
(353)
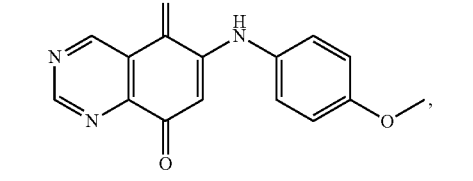
(354)
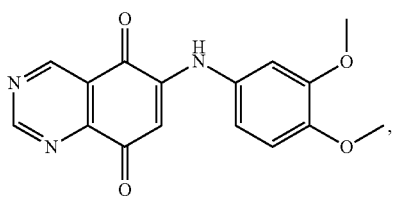
(355)
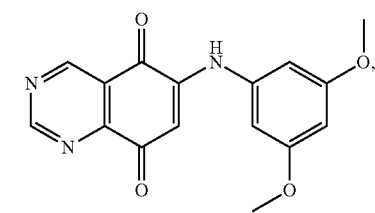
(357)
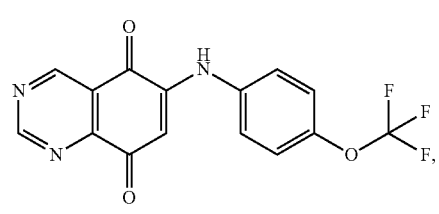
(327)
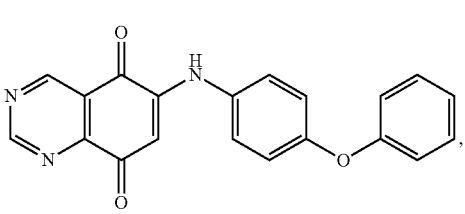
(324)
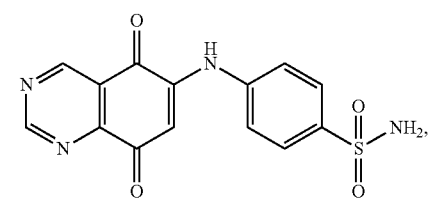
(328)
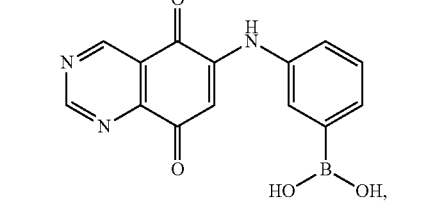
(333)
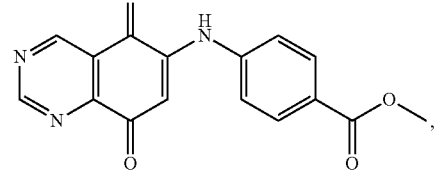
(331)

(329)
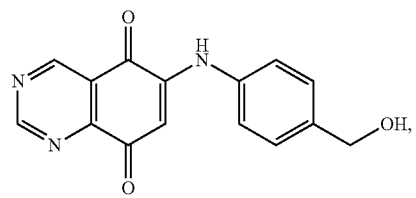
(332)
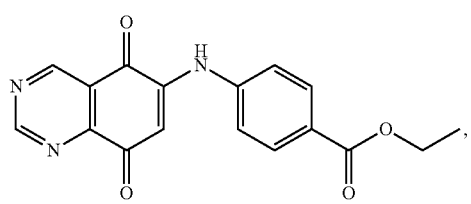
(330)
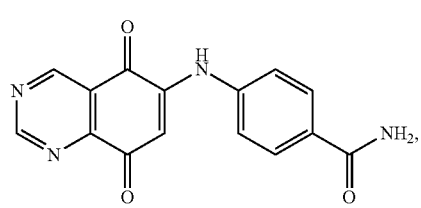
(340)
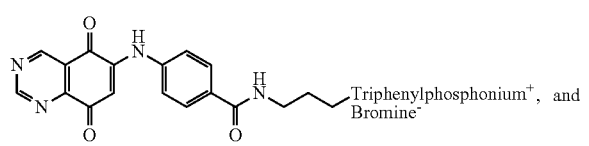
(359)
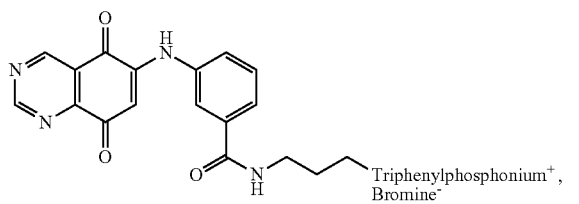
(396)
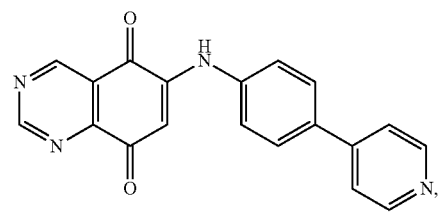
(397)
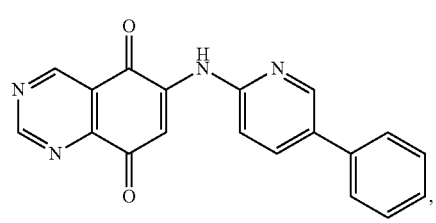
(398)
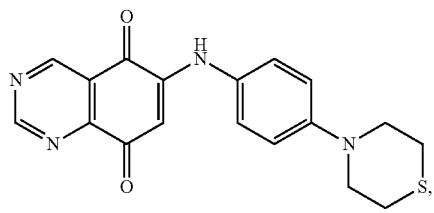
(399)
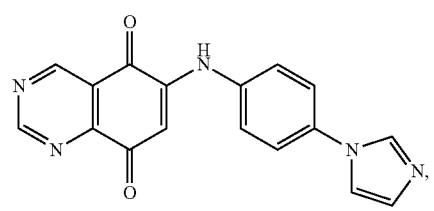
(400)
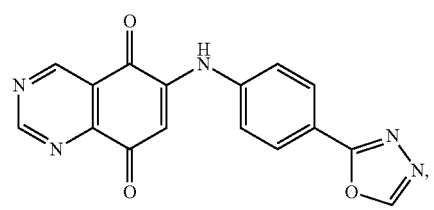
(401)
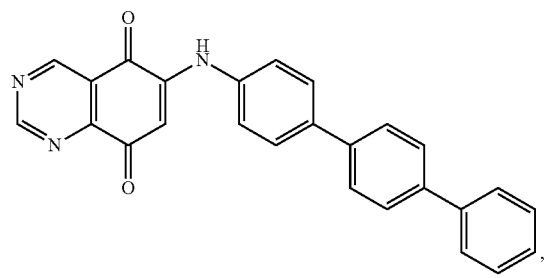
(402)
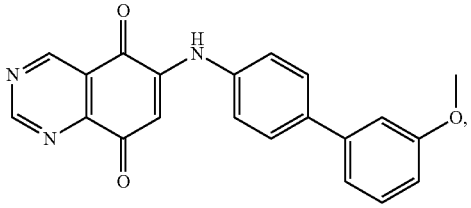
(403)
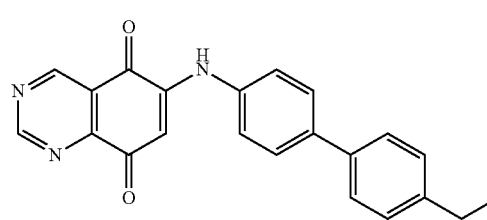
(404)
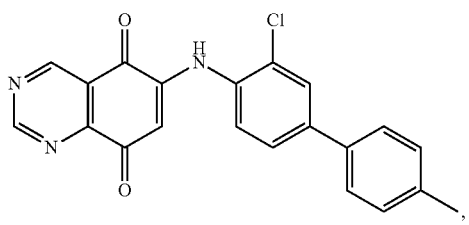

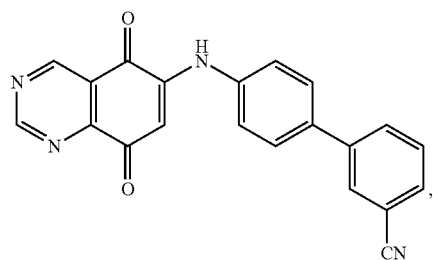
(405)
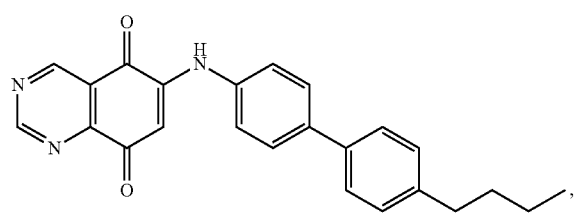
(406)
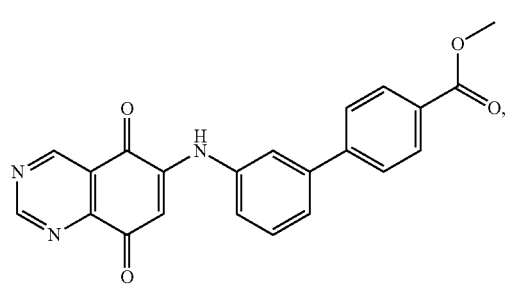
(407)
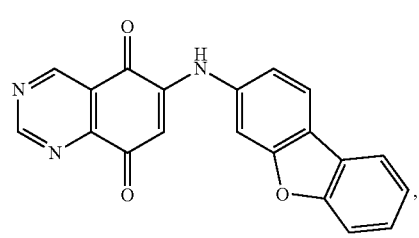
(408)
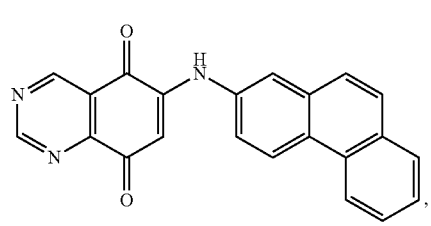
(409)
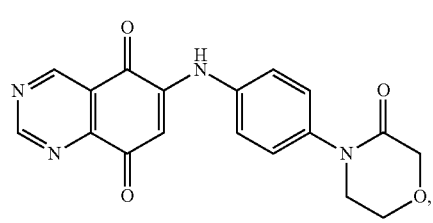
(410)
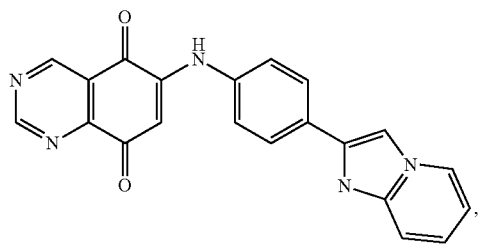
(411)
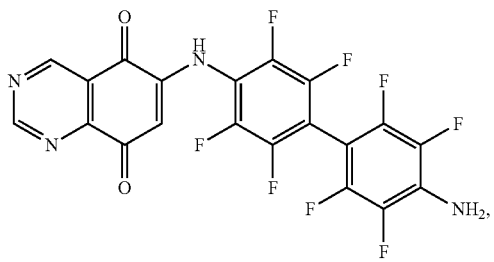
(412)
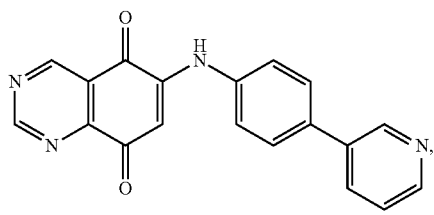
(413)
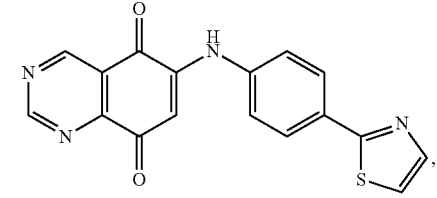
(414)
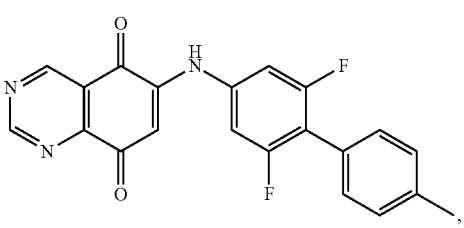
(415)
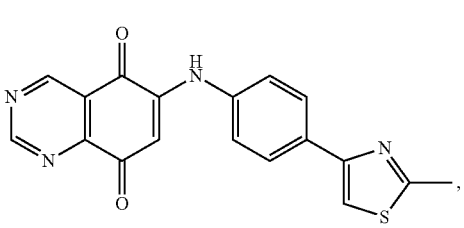
(416)
(417)

-continued

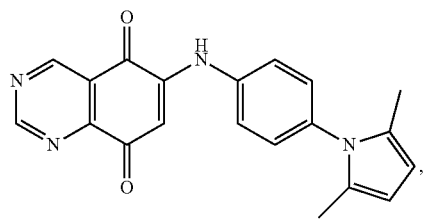
(418)

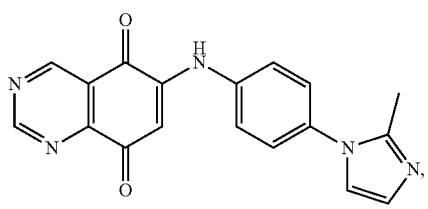
(419)

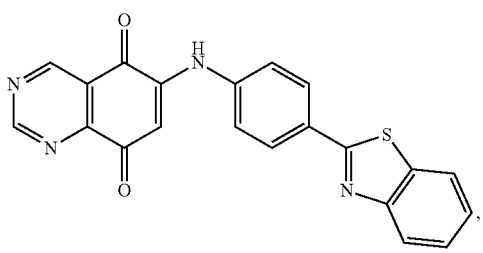
(420)

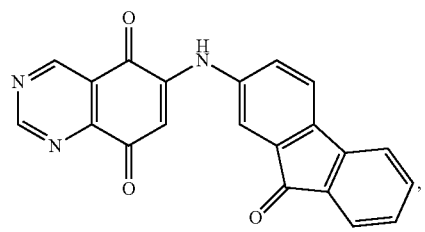
(421)

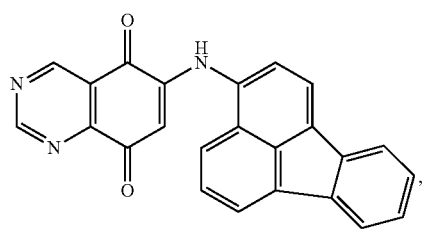
(422)

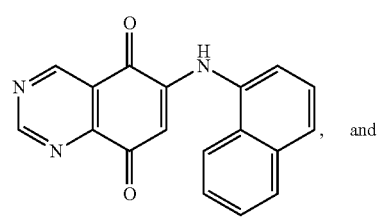
(423)

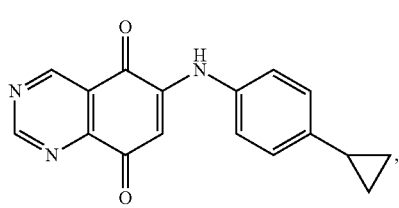
(424)

or a pharmaceutically acceptable salt, solvate, or prodrug thereof.

Table 1 (see, Examples) shows the structure and cytotoxicity of such QD compounds in MiaPaCa2, Panc-1 and BxPC-3 cells by MTT assay.

The invention further provides processes for preparing any of the compounds of the present invention through following at least a portion of the techniques recited the Examples.

The invention also relates to the use of compounds for sensitizing cells to additional agent(s), such as inducers of apoptosis and/or cell cycle arrest, and chemoprotection of normal cells through the induction of cell cycle arrest prior to treatment with chemotherapeutic agents. The compounds of the invention are useful for the treatment, amelioration, or prevention of disorders, such as those responsive to induction of apoptotic cell death, e.g., disorders characterized by dysregulation of apoptosis, including hyperproliferative diseases such as cancer (e.g., PDAC). In certain embodiments, the compounds can be used to treat, ameliorate, or prevent cancer that is characterized by resistance to cancer therapies (e.g., those cancer cells which are chemoresistant, radiation resistant, hormone resistant, and the like). In certain embodiments, the cancer is pancreatic cancer and/or PDAC. In some embodiments, the cancer is selected from breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

The invention also provides pharmaceutical compositions comprising the compounds of the invention in a pharmaceutically acceptable carrier.

The invention also provides kits comprising a compound of the invention and instructions for administering the compound to an animal. The kits may optionally contain other therapeutic agents, e.g., anticancer agents or apoptosis-modulating agents.

Figure 1:
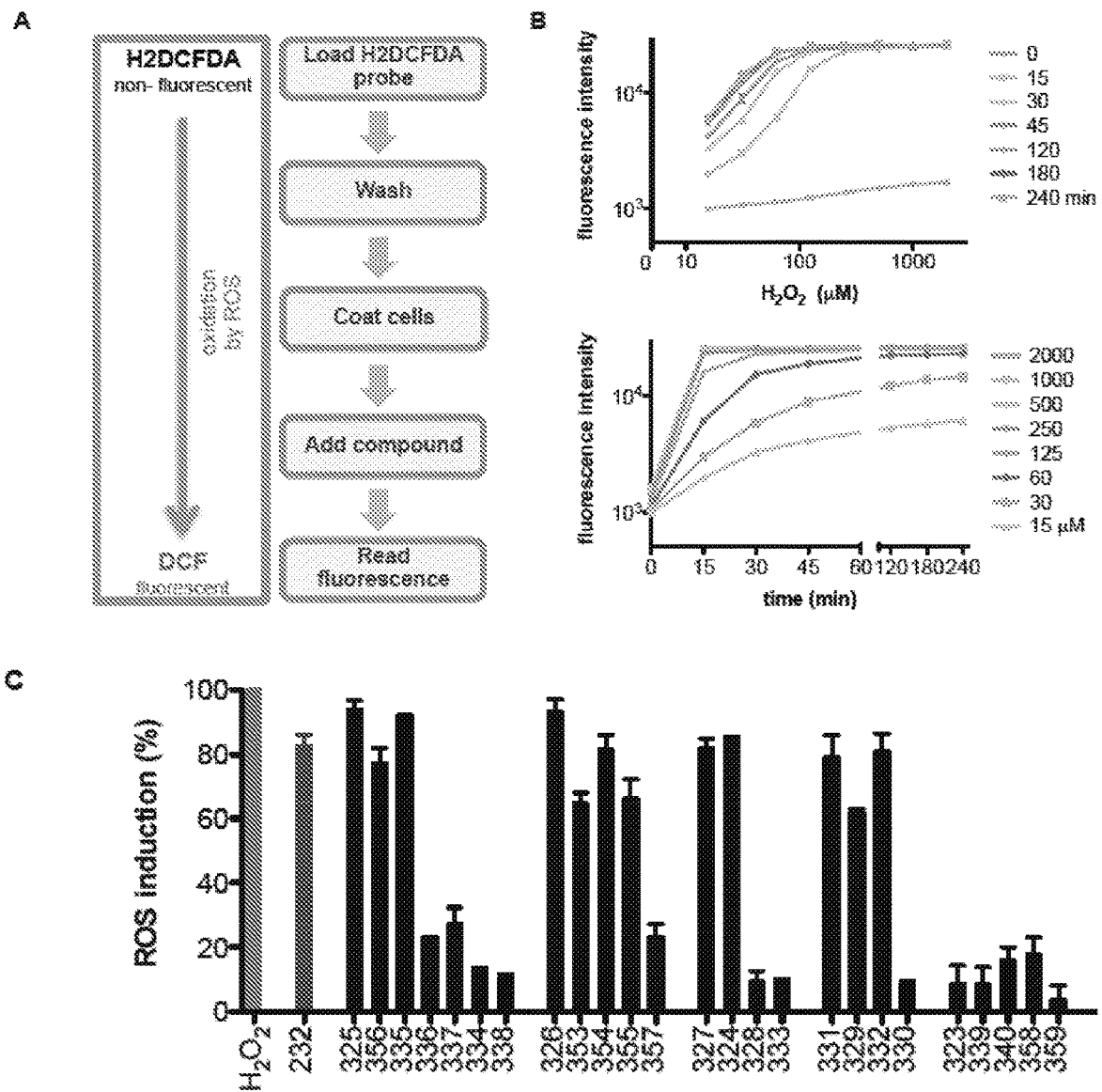
FIG. 1A-C: Cytotoxicity of QD compounds correlates with ROS induction. A) Illustration of cell-based ROS detection assay. Cell permeable H2DCFDA probe was added to MiaPaCa-2 cells and converted into highly fluorescent DCF in the presence of ROS. Fluorescent signal was detected by BioTek H1 plate reader as indicator of ROS level. B) $H_2O_2$, a form of ROS, induces conversion of H2DCFDA into DCF dose and time dependently. C) Arranged by structural groups, new QD analogues show different ROS induction activity at 10 µM after 24 h treatment. H$_2$O$_2$ treatment at 300 µM for 24 h is used as positive control representing full activation. ROS induction activity of QD compounds was normalized to positive control. Graphical data is presented as Mean±SD from three independent experiments.

SCID mice. MiaPaCa-2 engrafted mice were randomized into vehicle control (n=5) or QD325 treatment (n=5) group when tumor size reached 65 mm$^3$. QD325 was given at 5 mg/kg five times a week until day 44. B) Body weight of engrafted mice was not affected by QD325 treatment at 5 mg/kg. Data points represent Mean±SEM. C) Representative micrographs of hematoxylin and eosin (H&E)-stained organ sections. Images were taken with Olympus IX83 inverted microscope at 20× magnification. In histopathology study, no major microscopic changes were detected in major organs after QD325 treatment. D) Representative immunohistochemistry images for Ki67 staining of MiaPaCa-2 xenograft sections. QD325 decreased Ki67 index (percentage of Ki67 positive cells in the field) of treated tumors. Data represents Mean±SD (n=9, 3 tumors from each group, 3 images of each tumor section). P values were calculated using student's t-test. E) NQO1, HO-1, CHOP, GRP78 protein levels in vehicle or QD325 treated MiaPaCa-2 xenograft.

FIG. 13A-F shows that QD325 inhibits tumor growth of MiaPaCa-2 xenograft. A) QD325 treatment at 5 mg/kg inhibits growth of MiaPaCa-2 xenograft in NOD/SCID mice. MiaPaCa-2 engrafted mice were randomized into vehicle control (n=5) or QD325 treatment (n=5) group when tumor size reached 65 mm3. QD325 were given at 5 mg/kg five times a week until day 44. Three mice from each group were euthanized for tissue analysis. Two mice remained in each group after day 44 and QD325 doses were increased from 5 mg/kg to 20 mg/kg until day 67. B) Body weight of engrafted mice was not affected by QD325 treatment from 5-20 mg/kg. Error bars indicate mean±SEM. C) Gemcitabine treatment at 15 mg/kg inhibits growth of MiaPaCa-2 xenograft in NOD/SCID mice. MiaPaCa-2 engrafted mice were randomized into vehicle control (n=4), gemcitabine treatment 1 (n=3), gemcitabine treatment 2 (n=4) groups when tumor size reached 75 mm3. In treatment 1, gemcitabine was given at 15 mg/kg once a week for 48 days; in treatment 2, gemcitabine was given at 15 mg/kg twice a week for 15 days. Data points represent Mean±SEM. D) Body weight of engrafted mice is not affected by gemcitabine treatment in either dosing frequency. E) QD325 treatment at 5 mg/kg inhibits growth of MiaPaCa-2 xenograft in NOD/SCID mice. MiaPaCa-2 engrafted mice were randomized into vehicle control (n=4), gemcitabine treatment (n=3), QD325 treatment (n=3) and combination treatment groups (n=3) when tumor size reached 75 mm3. QD325 was given at 5 mg/kg five times a week and gemcitabine was given at 15 mg/kg once a week. Data points represent Mean±SEM. F) Body weight of engrafted mice was not affected by gemcitabine or QD325 treatment.

DEFINITIONS

The term "anticancer agent" as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1; herein incorporated by reference in its entirety).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula NW$_4^+$, wherein W is C$_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a benzoic acid compound of the invention), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 450%, or at least about 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The term "neoplastic disease," as used herein, refers to any abnormal growth of cells being either benign (non-cancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

DETAILED DESCRIPTION OF THE INVENTION

Altered redox homeostasis provides distinctive therapeutic opportunities for the treatment of pancreatic cancer. The novel quinazolinediones (QDs) described herein are redox modulators leading to potent growth inhibition in pancreatic ductal adenocarcinoma (PDAC) cell lines. In experiments conducted during the course of developing embodiments for the present invention, a lead optimization campaign yielded QD325 as the most potent candidate with substantial ROS induction. Mechanistic studies with next-generation sequencing revealed global stress responses with QD compounds in nucleus, endoplasmic reticulum, and mitochondria. QDs activated Nrf2-mediated oxidative stress and unfolded protein responses as demonstrated by dose dependent increases in nascent RNA synthesis of representative genes NQO1, HMOX1, DDIT3 and HSPA5. At higher concentrations, QDs could block mitochondria function by inhibiting synthesis of mtDNA transcripts and downregulating mtDNA-encoded OXPHOS enzyme. More significantly, QD325 treatment was well tolerated in vivo and significantly delayed tumor growth in mice. Such results support the use of QD325 as a new therapeutic strategy in the treatment of PDAC.

Accordingly, the present invention relates to a new class of small-molecules having a quinazolinedione structure which function as ROS inducers and inhibitors of mitochondrial activity, and their use as therapeutics for the treatment of cancer and other diseases.

In a particular embodiment, quinazolinedione compounds encompassed within Formula I are provided:

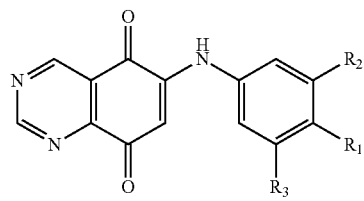

(Formula I)

or

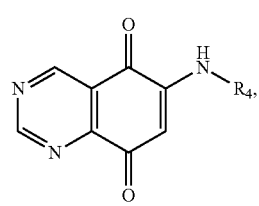

(Formula II)

including pharmaceutically acceptable salts, solvates, and/or prodrugs thereof.

Formula I is not limited to a particular chemical moiety for $R_1$, $R_2$, and $R_3$. Formula II is not limited to a particular chemical moiety for $R_4$.

In some embodiments, the particular chemical moiety for $R_1$, $R_2$, and $R_3$ independently include any chemical moiety that permits the resulting compound to induce ROS and inhibit mitochondrial activity within cancer cells. In some embodiments, the particular chemical moiety for $R_4$ includes any chemical moiety that permits the resulting compound to induce ROS and inhibit mitochondrial activity within cancer cells.

In some embodiments, the particular chemical moiety for $R_1$, $R_2$, and $R_3$ independently include any chemical moiety that permits the resulting compound to induce ROS and inhibit mitochondrial activity within cancer cells through activating Nrf2-mediated oxidative stress and unfolded protein responses (e.g., through increased nascent RNA synthesis of representative genes NQO1, HMOX1, DDIT3 and HSPA5). In some embodiments, the particular chemical moiety for $R_4$ includes any chemical moiety that permits the resulting compound to induce ROS and inhibit mitochondrial activity within cancer cells through activating Nrf2-mediated oxidative stress and unfolded protein responses (e.g., through increased nascent RNA synthesis of representative genes NQO1, HMOX1, DDIT3 and HSPA5).

In some embodiments, the particular chemical moiety for $R_1$, $R_2$, and $R_3$ independently include any chemical moiety that permits the resulting compound to induce ROS and inhibit mitochondrial activity occurs through, for example, inhibiting synthesis of mtDNA transcripts and downregulating mtDNA-encoded OXPHOS enzyme. In some embodiments, the particular chemical moiety for $R_4$ includes any chemical moiety that permits the resulting compound to induce ROS and inhibit mitochondrial activity occurs through, for example, inhibiting synthesis of mtDNA transcripts and downregulating mtDNA-encoded OXPHOS enzyme.

In some embodiments, $R_1$ is a chemical moiety selected from Hydrogen,

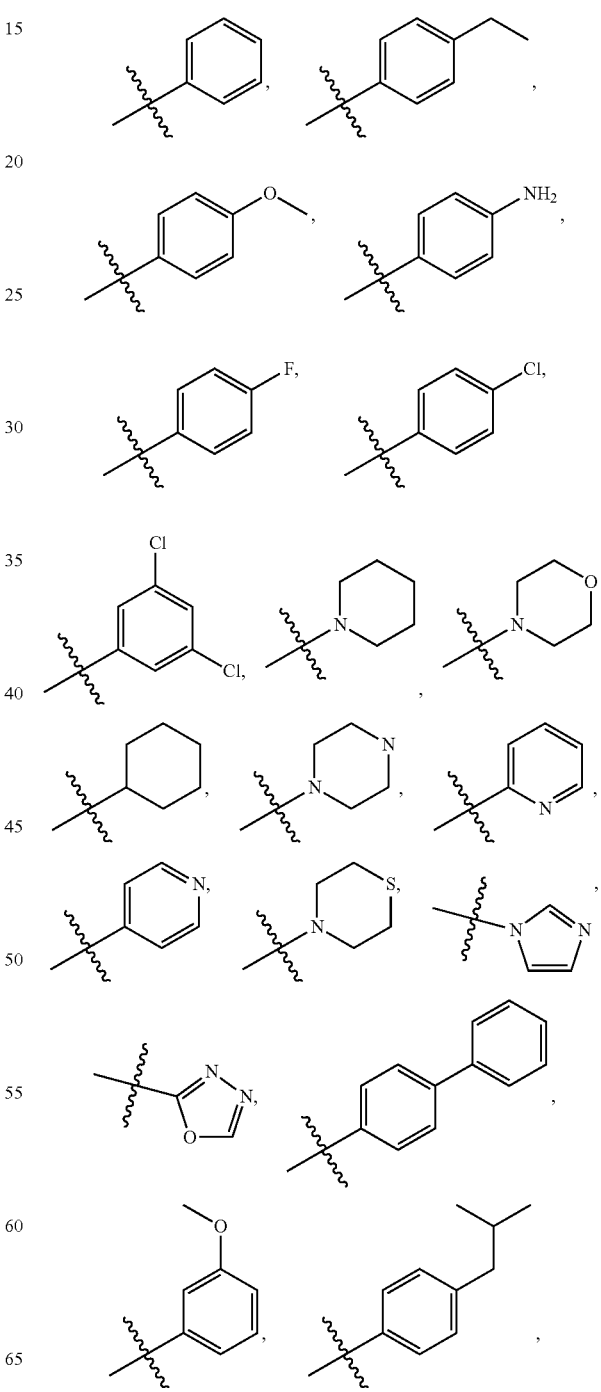

-continued
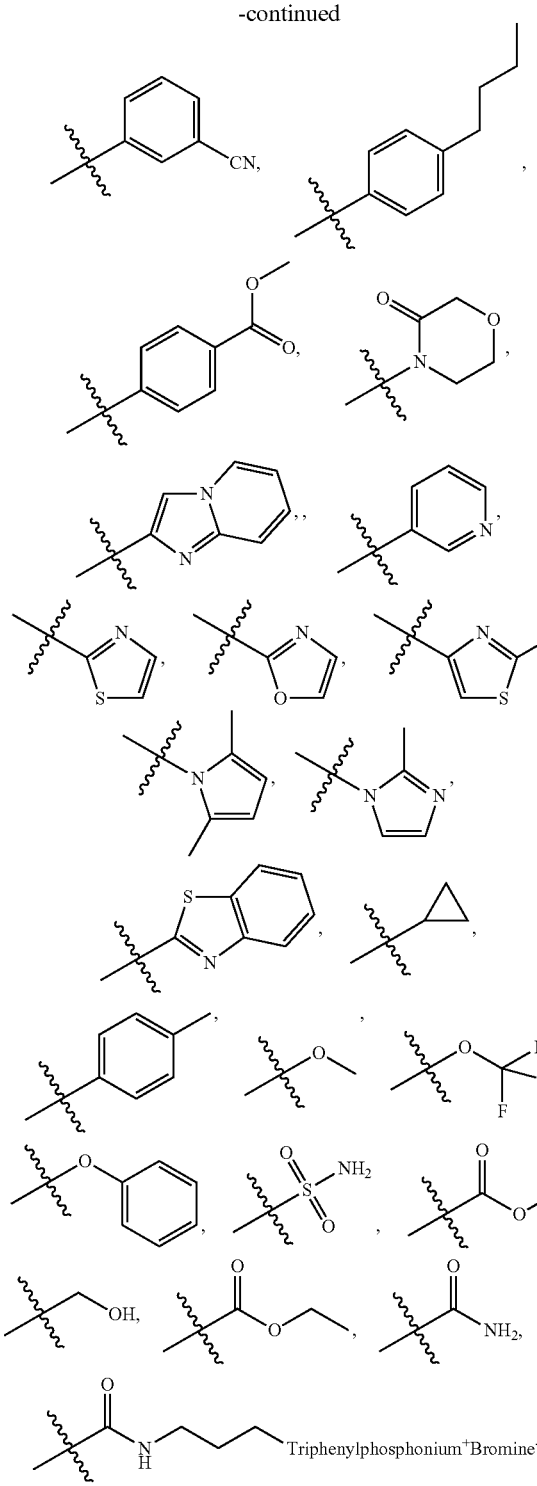
In some embodiments, R₂ is a chemical moiety selected from Hydrogen,
Fluorine, and
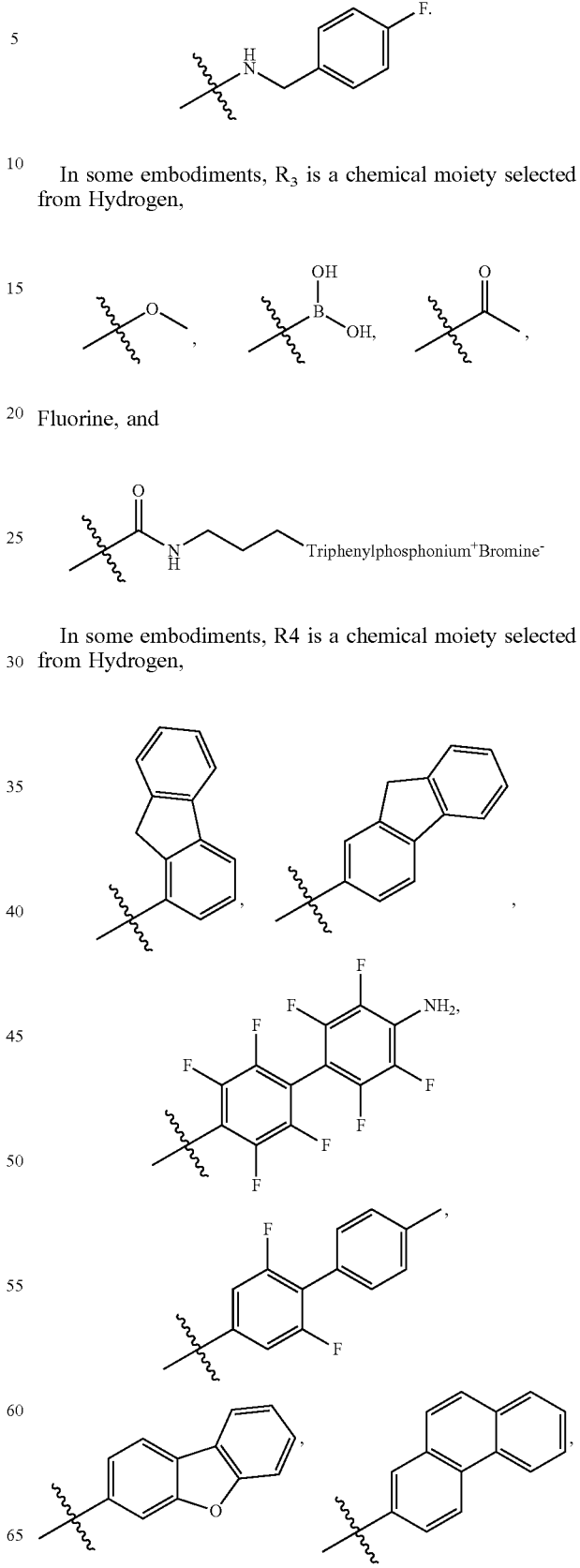
In some embodiments, $R_3$ is a chemical moiety selected from Hydrogen,
Fluorine, and
In some embodiments, R4 is a chemical moiety selected from Hydrogen,

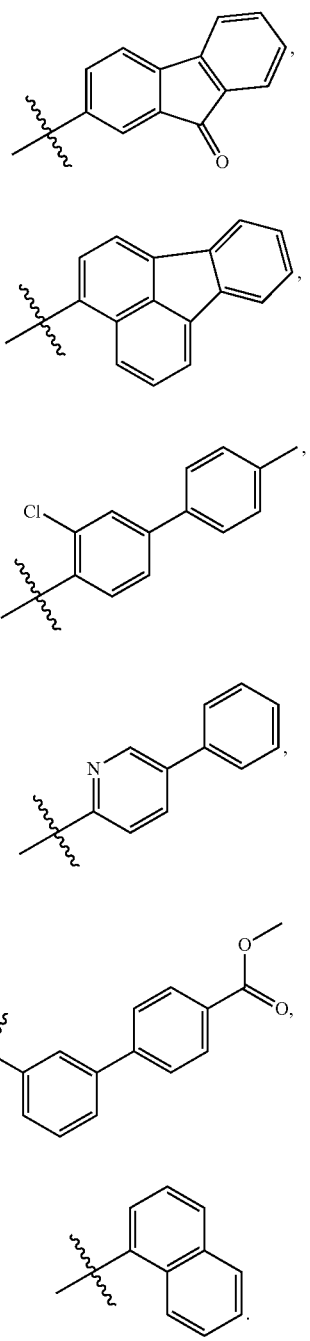
In some embodiments, the following compounds are contemplated for Formula I or Formula II:
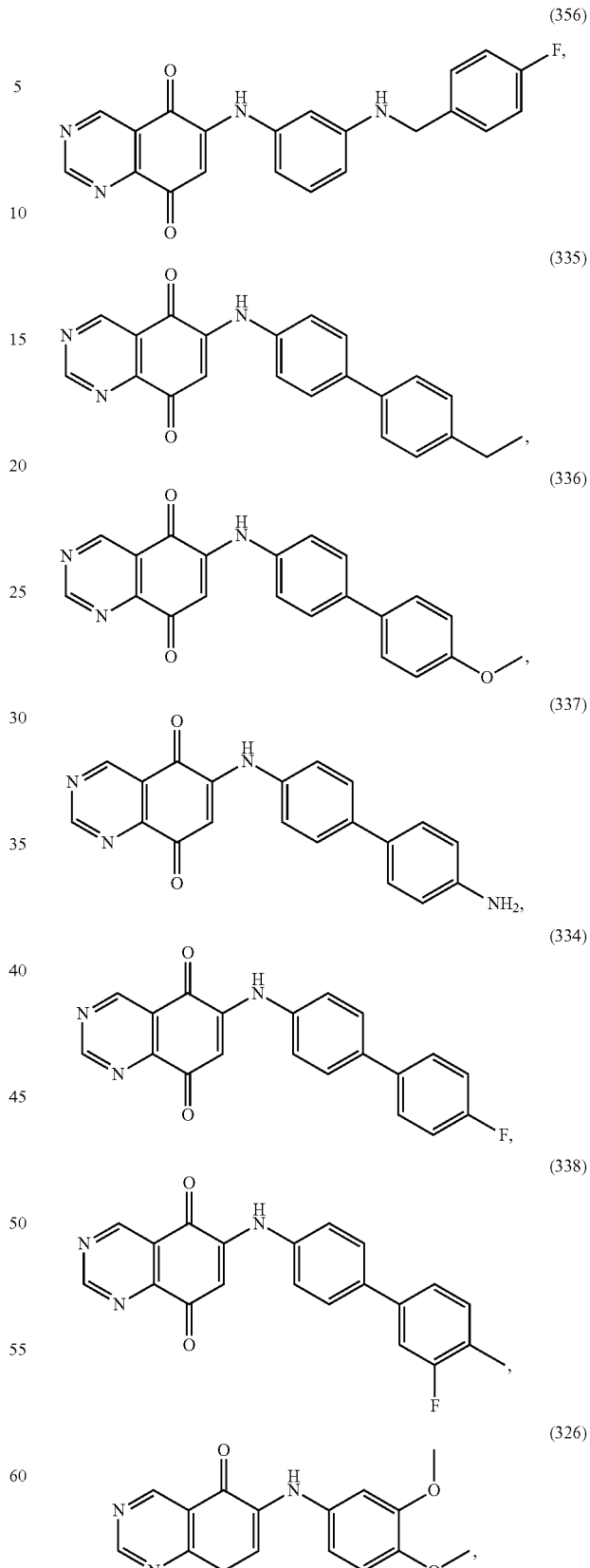

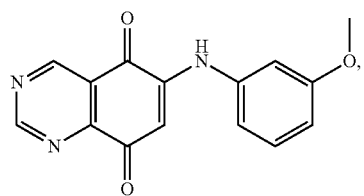
(353)
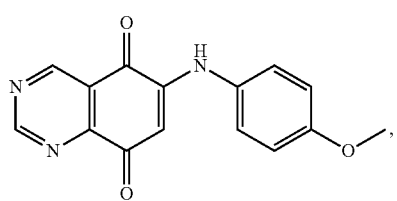
(354)
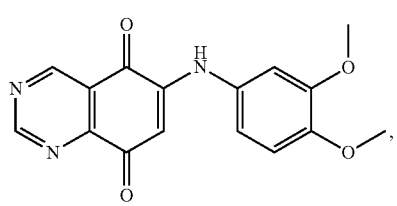
(355)
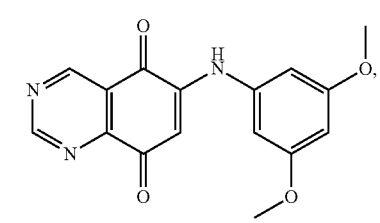
(357)
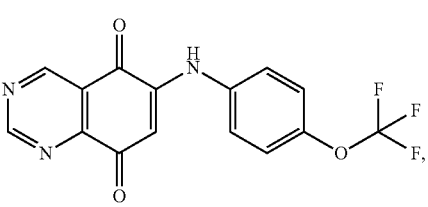
(327)
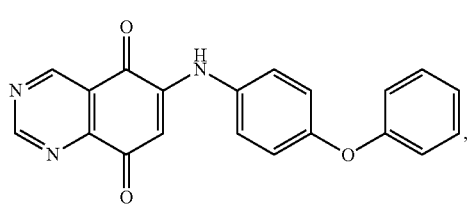
(324)
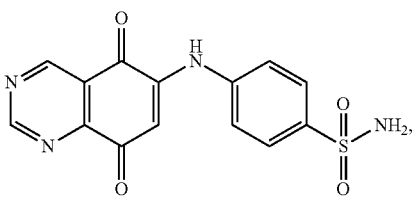
(328)
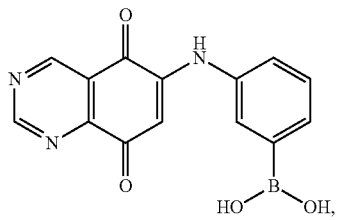
(333)
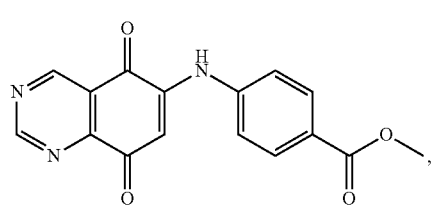
(331)
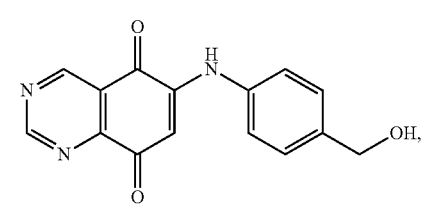
(329)
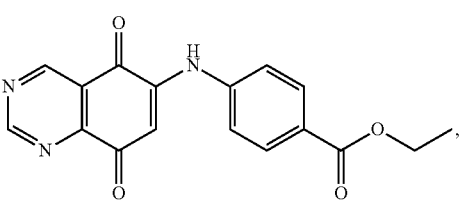
(332)
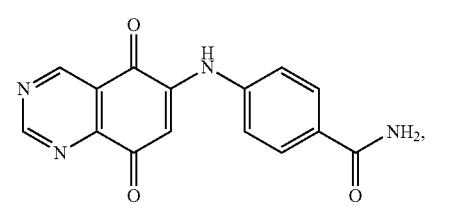
(330)
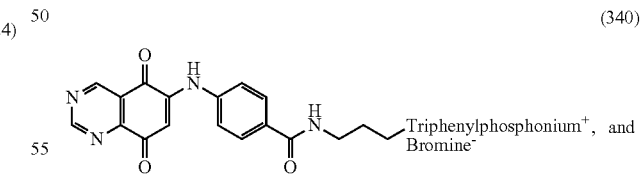
(340)
and
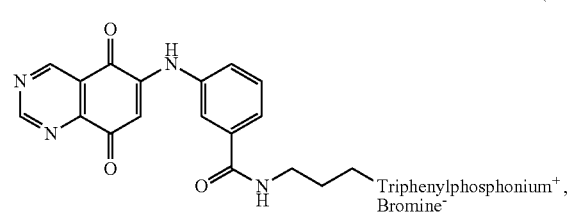
(359)

(396) 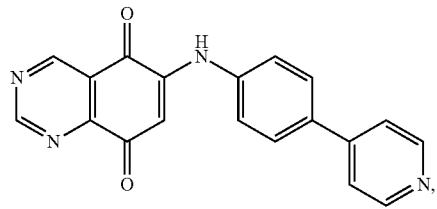
(397) 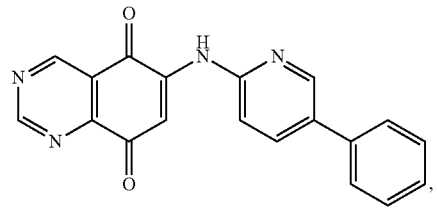
(398) 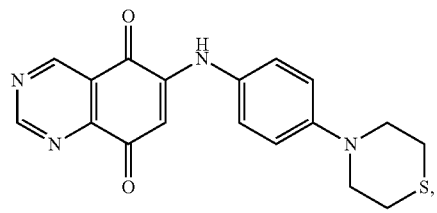
(399) 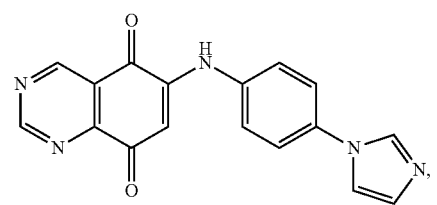
(400) 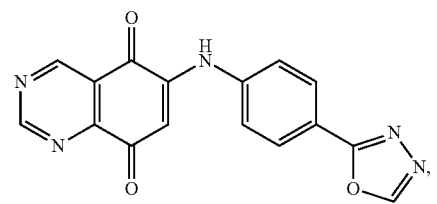
(401) 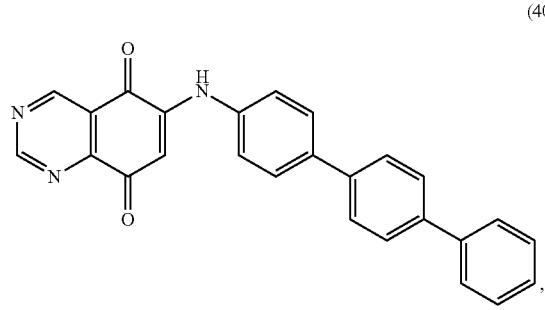
(402) 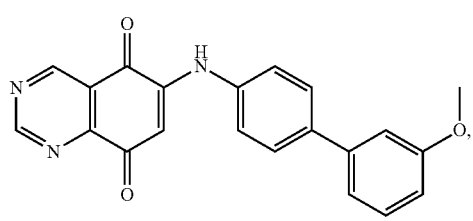
(403) 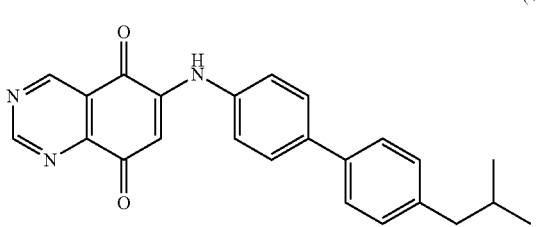
(404) 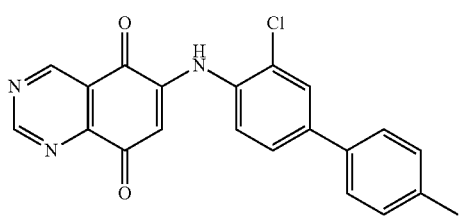
(405) 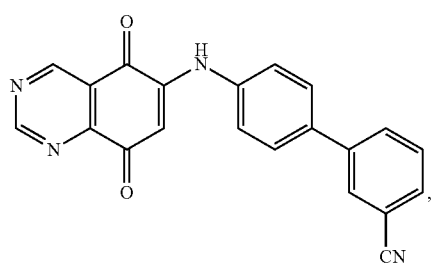
(406) 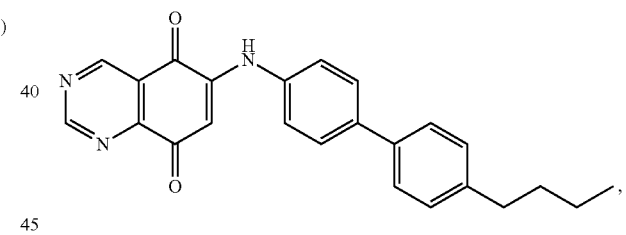
(407) 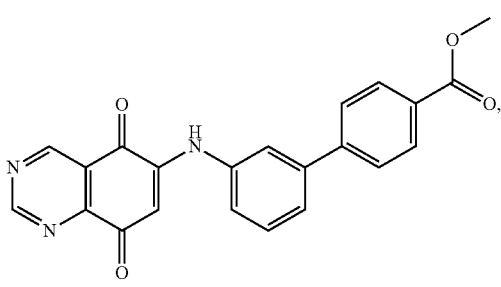
(408) 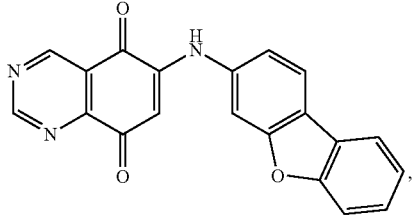

(409)
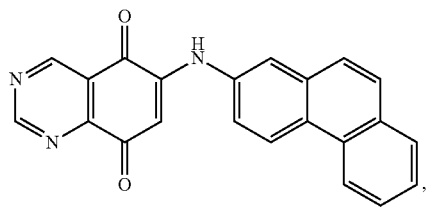
(410)
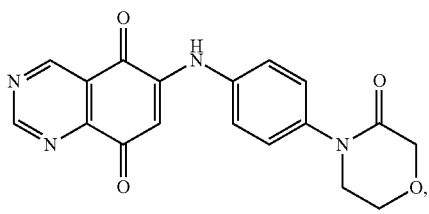
(411)
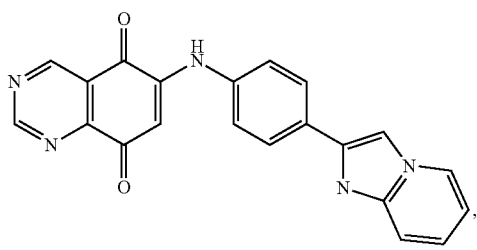
(412)
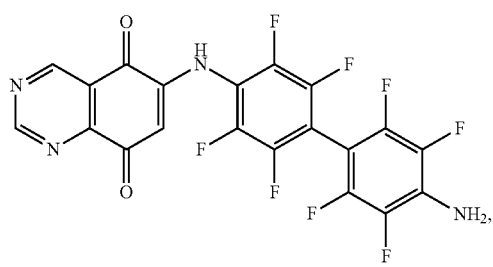
(413)
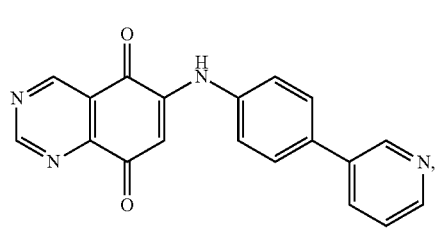
(414)
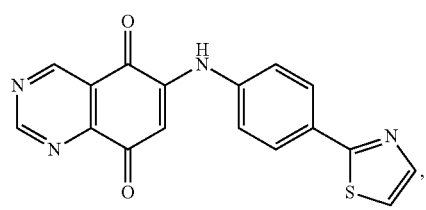
(415)
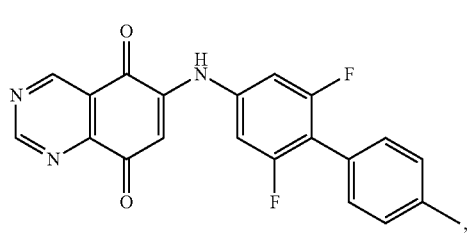
(416)
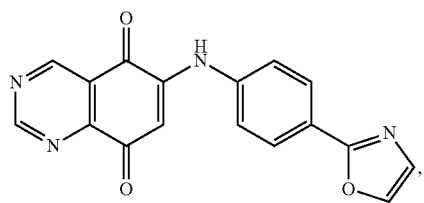
(417)
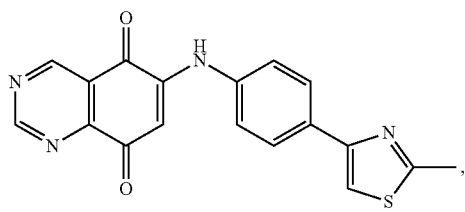
(418)
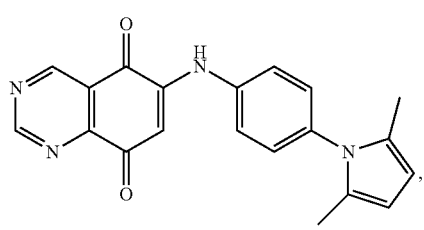
(419)
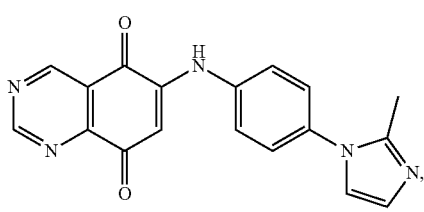
(420)
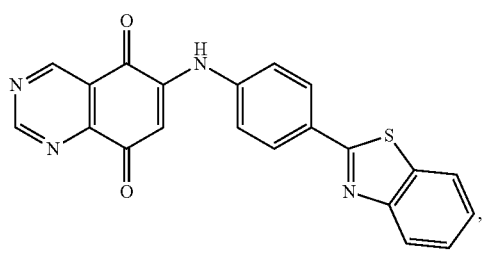
(421)
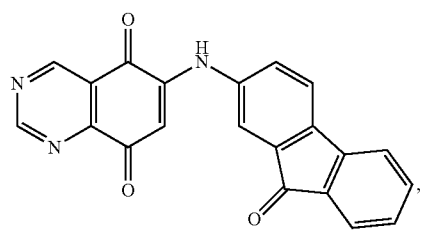
(422)
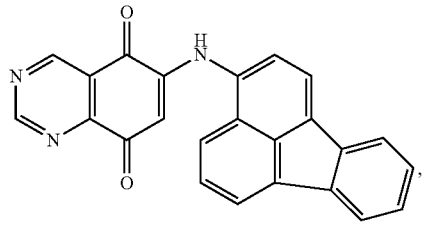

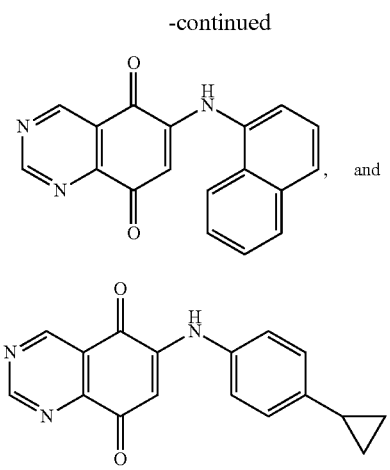

or a pharmaceutically acceptable salt, solvate, or prodrug thereof.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, pancreatic cancer, PDAC, and other types of cancer (e.g., breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma). In some embodiments, the cancer cells being treated are metastatic. In other embodiments, the cancer cells being treated are resistant to anticancer agents.

Some embodiments of the present invention provide methods for administering an effective amount of a compound of the invention and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is an anticancer agent.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 3 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 3

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2, 4, 6-triamine) | Hexalen | US Bioscience, West Conshohocken, PA |

TABLE 3-continued

| | | |
|---|---|---|
| Amifostine (ethanethiol, 2-[(3-aminopropyl)amino]-, dihydrogen phosphate (ester)) | Ethyol | US Bioscience |
| Anastrozole (1,3-Benzenediacetonitrile, a, a, a', a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0, 0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |

TABLE 3-continued

| | | |
|---|---|---|
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1 S,3 S )-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-0-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3, 17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2', 2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator titmetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin MA | Biogen IDEC, Inc., Cambridge |

TABLE 3-continued

| | | |
|---|---|---|
| Idarubicin (5, 12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyOmethyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3', 4': 6,7] indolizino[1,2-b] quinoline-3,14(4H, 12H) dione hydrochloride trihydrate) | Camptosa | Pharmaciar & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]ami no]benzoyl], calcium salt (1:1)) | Wellcovorin, Leucovorin | Immunex, Corp., Seattle, WA |
| Levamisole HCl ((-)-( S)-2,3,5, 6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α( acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6 H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methyl-amino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)ami no]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β, 20-Epoxy-1,2a, 4,7β, 10β, 13a-hexahydroxytax-11-en-9-one 4,10-diacetate 2-benzoate 13-ester with (2R, 3 S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypoly-ethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., |

TABLE 3-continued

| | | |
|---|---|---|
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-( 1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rittiximab (recombinant anti-CD20 antibody) | Rittman | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N, N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr ]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1"-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3', 4': 6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoyl-phorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflomithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpimase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifamib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of the invention with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of the invention and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

This example demonstrates that QD compounds inhibit proliferation of pancreatic cancer cells.

To establish a robust structure-activity relationships for a QD series of compounds, 25 new analogues of the previous lead compound, QD232, were designed and synthesized to better elucidate their mechanisms of action. The cytotoxicity of these compounds were first tested using MTT assay in three PDAC cell lines MiaPaCa-2, Panc-1 and BxPC-3. Nine of these novel analogues showed improved cytotoxicity in at least two cell lines (Table 1). QD325 was shown to be the best analogue with $IC_{50}$ values <1 μM in the three PDAC cell lines.

TABLE 1

Cytotoxicity of QD compounds in pancreatic cancer cell lines by MTT assay

| | $IC_{50}$ (μM)[1] | | |
|---|---|---|---|
| ID | Mia PaCa-2 | Panc-1 | BxPC-3 |
| 232 | 2.3 ± 0.2 | 0.9 ± 0.2 | 5.2 ± 0.8 |
| 323 | 9.4 ± 0.9 | 18.0 ± 2.5 | 19.4 ± 1.6 |
| 324 | 3.7 ± 0.7 | 1.8 ± 0.2 | 3.6 ± 0.4 |
| 325 | 0.9 ± 0.2 | 0.4 ± 0.1 | 0.5 ± 0.1 |
| 326 | 1.5 ± 0.1 | 0.8 ± 0.1 | 1.6 ± 0.3 |
| 327 | 1.4 ± 0.2 | 0.9 ± 0.1 | 0.9 ± 0.1 |
| 328 | >10 | >10 | >10 |
| 329 | 3.5 ± 1.3 | 1.0 ± 0.2 | 2.7 ± 0.3 |
| 330 | 8.0 ± 0.9 | 6.3 ± 0.3 | >10 |
| 331 | 2.2 ± 0.4 | 1.1 ± 0.4 | 5.8 ± 0.3 |
| 332 | 5.5 ± 1.5 | 1.6 ± 0.3 | 5.9 ± 0.1 |
| 333 | >10 | 9.0 ± 1.0 | >10 |
| 334 | 3.5 ± 1.0 | 3.2 ± 0.8 | 4.4 ± 0.9 |
| 335 | 2.0 ± 0.1 | 1.2 ± 0.1 | 3.1 ± 0.7 |
| 336 | 2.1 ± 0.5 | 2.3 ± 0.3 | 3.5 ± 0.5 |
| 337 | 2.5 ± 0.2 | 3.7 ± 0.1 | 3.5 ± 0.6 |
| 338 | 4.6 ± 1.1 | 4.8 ± 0.1 | 5.0 ± 0.7 |
| 339 | >30 | >30 | >30 |
| 340 | 15.3 ± 2.5 | 11.7 ± 1.5 | 21.5 ± 2.3 |
| 353 | 1.8 ± 0.3 | 0.6 ± 0.1 | 1.8 ± 0.1 |
| 354 | 1.9 ± 0.2 | 0.8 ± 0.2 | 1.7 ± 0.2 |
| 355 | 1.8 ± 0.1 | 0.9 ± 0.3 | 1.5 ± 0.2 |
| 356 | 1.7 ± 0.2 | 1.0 ± 0.1 | 1.4 ± 0.2 |
| 357 | 7.7 ± 2.0 | 7.2 ± 0.8 | 16.3 ± 1.5 |
| 358 | >30 | >30 | >30 |
| 359 | 16.3 ± 3.6 | 14.3 ± 1.5 | 21.3 ± 2.5 |
| Gemcitabine | 0.11 ± 0.07 | 0.20 ± 0.10 | 0.05 ± 0.02 |

[1]Data are presented as Mean ± SD from three independent experiments.

The QD analogues can be grouped into 5 major classes by chemical structures (Table 2). QD325 with phenyl group substitution on QD232 achieves more than two fold improvement in cytotoxicity, however, further modification with alkyl, methoxy, amine or fluorine substituted phenyl group did not further improve potency. Another major improvement in potency was achieved by methoxy substitution on QD232.

TABLE 2

Structure and cytotoxicity of QD compounds in MiaPaCa-2, Panc-1 and BxPC-3 cells by MTT assay. QD compounds are grouped by structure.

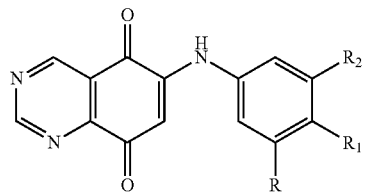

QD 232, 325-338, 340, 353-357, 359

| | Substitution group | | | IC$_{50}$ (μM)[1] | | |
|---|---|---|---|---|---|---|
| ID | R | R$_1$ | R$_2$ | MiaPaCa-2 | Panc-1 | BxPC-3 |
| 232 | COCH$_3$ | H | H | 2.3 ± 0.2 | 0.9 ± 0.2 | 5.2 ± 0.8 |
| 325 | H | Ph | H | 0.9 ± 0.2 | 0.4 ± 0.1 | 0.5 ± 0.1 |
| 356 | H | H | NHCH$_2$-(4-F-Ph) | 1.7 ± 0.2 | 1.0 ± 0.1 | 1.4 ± 0.2 |
| 335 | H | 4-Et-Ph | H | 2.0 ± 0.1 | 1.2 ± 0.1 | 3.1 ± 0.7 |
| 336 | H | 4-OCH$_3$-Ph | H | 2.1 ± 0.5 | 2.3 ± 0.3 | 3.5 ± 0.5 |
| 337 | H | 4-NH$_2$-Ph | H | 2.5 ± 0.2 | 3.7 ± 0.1 | 3.5 ± 0.6 |
| 334 | H | 4-F-Ph | H | 3.5 ± 1.0 | 3.2 ± 0.8 | 4.4 ± 0.9 |
| 338 | F | 4-CH$_3$-Ph | H | 4.6 ± 1.1 | 4.8 ± 0.1 | 5.0 ± 0.7 |
| 326 | OCH$_3$ | OCH$_3$ | OCH$_3$ | 1.5 ± 0.1 | 0.8 ± 0.1 | 1.6 ± 0.3 |
| 353 | H | H | OCH$_3$ | 1.8 ± 0.3 | 0.6 ± 0.1 | 1.8 ± 0.1 |
| 354 | H | OCH$_3$ | H | 1.9 ± 0.2 | 0.8 ± 0.2 | 1.7 ± 0.2 |
| 355 | H | OCH$_3$ | OCH$_3$ | 1.8 ± 0.1 | 0.9 ± 0.3 | 1.5 ± 0.2 |
| 357 | OCH$_3$ | H | OCH$_3$ | 7.7 ± 2.0 | 7.2 ± 0.8 | 16.3 ± 1.5 |
| 327 | H | OCF$_3$ | H | 1.4 ± 0.2 | 0.9 ± 0.1 | 0.9 ± 0.1 |
| 324 | H | O-Ph | H | 3.7 ± 0.7 | 1.8 ± 0.2 | 3.6 ± 0.4 |
| 328 | H | SO$_2$NH$_2$ | H | >10 | >10 | >10 |
| 333 | B(OH)$_2$ | H | H | >10 | 9.0 ± 1.0 | >10 |
| 331 | H | COOCH$_3$ | H | 2.2 ± 0.4 | 1.1 ± 0.4 | 5.8 ± 0.3 |
| 329 | H | CH$_2$OH | H | 3.5 ± 1.3 | 1.0 ± 0.2 | 5.7 ± 0.3 |
| 332 | H | COOCH$_2$CH$_3$ | H | 5.5 ± 1.5 | 1.6 ± 0.3 | 5.9 ± 0.1 |
| 330 | H | CONH$_2$ | H | 8.0 ± 0.9 | 6.3 ± 0.3 | >10 |
| 323[2] | N/A | N/A | N/A | 9.4 ± 0.9 | 18.0 ± 2.5 | 19.4 ± 1.6 |
| 339[3] | N/A | N/A | N/A | >30 | >30 | >30 |
| 358[4] | N/A | N/A | N/A | >30 | >30 | >30 |
| 331 | H | COOCH$_3$ | H | 2.2 ± 0.4 | 1.1 ± 0.4 | 5.8 ± 0.3 |
| 340 | H | CONH(CH$_2$)$_3$(TPP)$^+$Br$^{-}$[5] | H | 15.3 ± 2.5 | 11.7 ± 1.5 | 21.5 ± 2.3 |
| 232 | COCH$_3$ | H | H | 2.3 ± 0.2 | 0.9 ± 0.2 | 5.2 ± 0.8 |
| 359 | CONH(CH$_2$)$_3$(TPP)$^+$Br$^{-}$[5] | H | H | 16.3 ± 3.5 | 14.3 ± 1.5 | 21.3 ± 2.5 |

[1]Data is presented as Mean ± SD from three independent experiments.
[2]Structure of intermediate QD323 is shown in Scheme 1.
[3]Structure of intermediate QD339 is shown in Scheme 4.
[4]Structure of intermediate QD358 is shown in Scheme 5.
[5]TPP stands for triphenylphosphonium.

Example II

This example demonstrates that cytotoxicity of QD compounds correlates with increased ROS production.

To quantify ROS induction by redox modulators, a high throughput ROS assay in 384-well plates using H2DCFDA as the ROS detection probe was developed (FIG. 1A). Using H$_2$O$_2$ as the positive control, detected time- and dose-dependent changes with a Z factor of 0.879 were measured, demonstrating good sensitivity and reproducibility of the assay (FIG. 1B).

Figure 2:
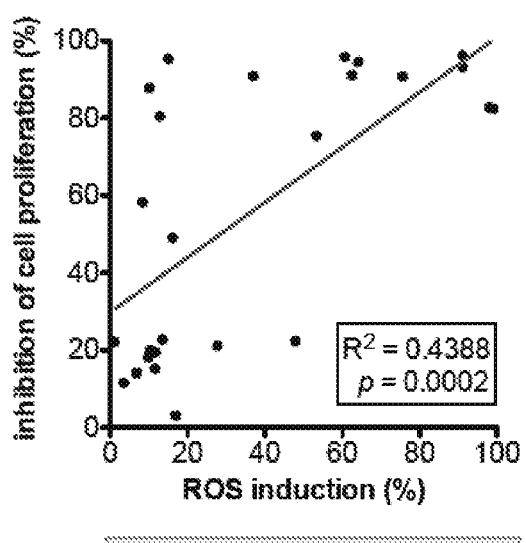
FIG. 2 shows that cytotoxicity of QD compounds correlates with ROS induction. Cytotoxicity of QD compounds is represented by inhibition of cell proliferation (%) at 3.3 or 10 µm after 72 h treatment in MiaPaCa-2 cells. ROS induction was determined for QD compounds at 3.3 or 10 µm after 24 h treatment in MiaPaCa-2 cells. Data points represent the mean values of three independent experiments. Linear correlation was analyzed by Prism.
Figure 2:
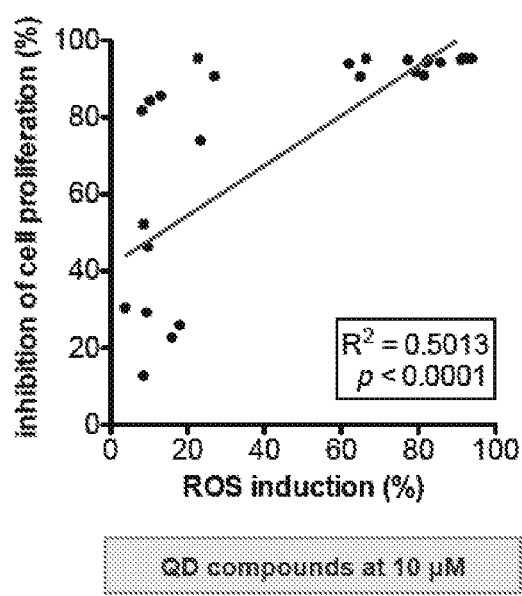

Treatment with QD compounds elicited significant ROS accumulation in MiaPaCa-2 cells. Among the 25 analogues, QD325, QD335 and QD326 exhibited significantly higher ROS induction than the lead compound QD232 after 24 h treatment (FIG. 1C), whereas six other analogues show similar ROS induction as the earlier lead. After 24 h the ROS dependent DCF fluorescence plateaued for all compounds and this time point was chosen for compound comparison. Inhibition of cell proliferation and ROS induction by QD compounds showed linear correlation with Pearson's correlation coefficient r of 0.66 at 3.3 μM (p=0.00002) and 0.7080 at 10 μM (p<0.0001), indicating positive correlations in both cases (FIG. 2). In general, the most cytotoxic compounds are also high ROS inducers (Table 2).

Figure 3:
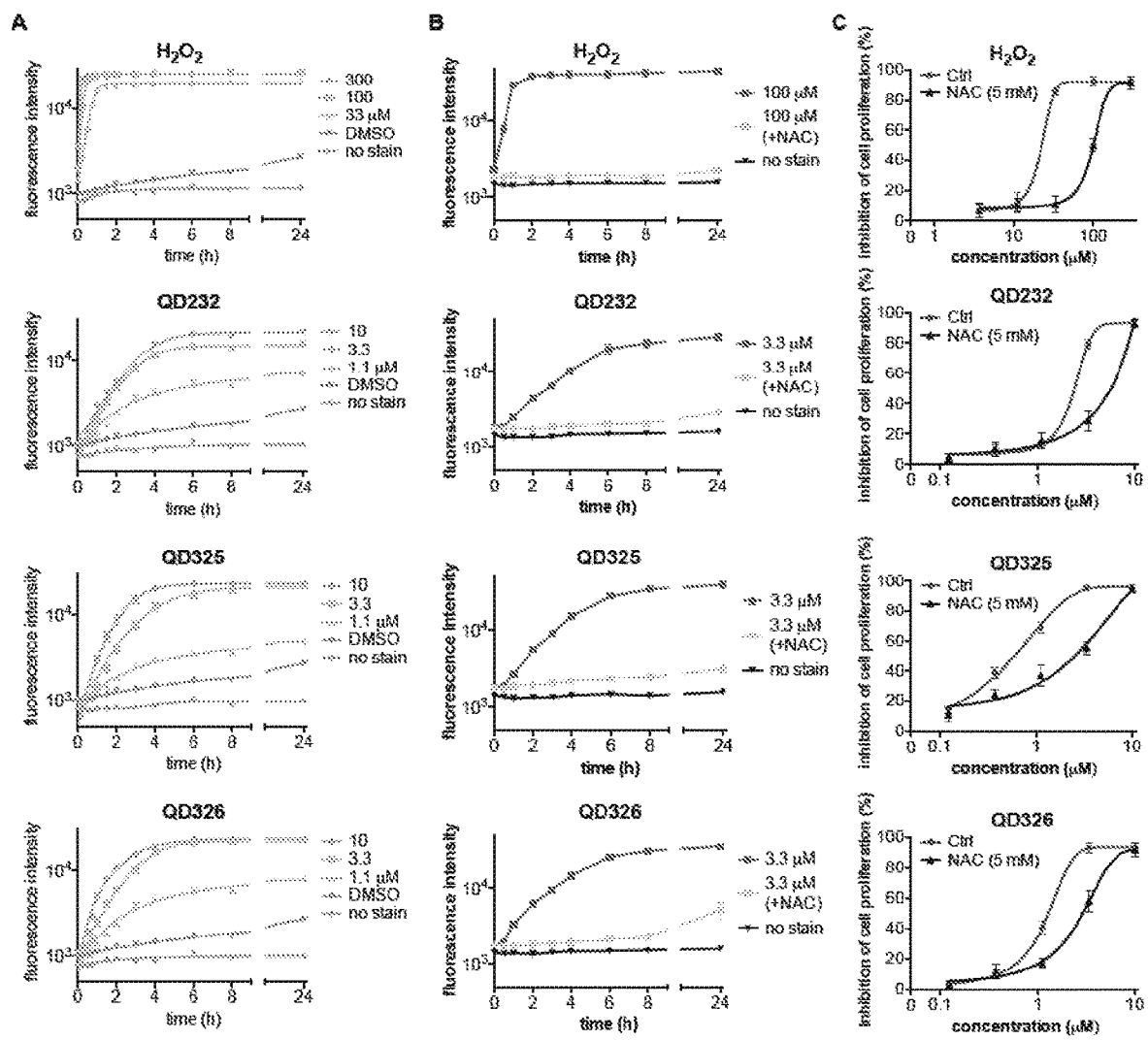
FIG. 3A-C: Cytotoxicity of QD compounds is reduced by NAC in MiaPaCa-2 cells. A) Parental compound QD232 induces ROS accumulation dose and time dependently. New analogues QD325 and QD326 induce stronger and more rapid ROS accumulation in MiaPaCa-2 cells. Compounds were tested at 10, 3.3 or 1.1 µM. DMSO was used as negative control to determine basal signal of the assay (DMSO). Cells without preloaded H2DCFDA were treated with compounds at 10 µM at the same conditions to determine the endogenous fluorescence of the compounds (no stain). Data points represent Mean±SD from duplicates. Graphs are representatives of three independent experiments. B) ROS induction by QD232, 325 and 326 is inhibited by NAC pretreatment (5 mM for 30 min). Data points represent Mean±SD from duplicates. Graphs are representatives of three independent experiments. C) Presence of NAC at 5 mM decreases cytotoxicity of QD232, 325 and 326. Cytotoxicity was determined by MTT assay after 72 h treatment. Data points represent Mean±SD from three independent experiments.

To validate ROS induction as the mechanism for cytotoxicity, the effect of QD compounds were evaluated in the presence and absence of the antioxidant N-acetyl-cysteine (NAC). For the lead compound QD232 and the two active analogues QD325 and QD326, a time- and dose-dependent accumulation of ROS was observed (FIG. 3A). A negative control without the H2DCFDA probe was included to exclude potential fluorescence of compounds interfering with the assay. While H$_2$O$_2$ treatment leads to immediate conversion of H2DCFDA to fluorescent DCF, treatment with QD compounds leads to a gradual induction of the fluorescent signal, implying ROS accumulation. For QD232, QD325 and QD326 treatments, ROS accumulation reaches peak levels after 4-6 h. At 10 and 3.3 μM, both QD325 and QD326 induce rapid and high ROS accumulation.

When cells were pretreated with 5 mM NAC, ROS induction by H$_2$O$_2$ and QD compounds was blocked (FIG.

3B). In the MTT assay, NAC decreased cytotoxicity of $H_2O_2$, QD232, QD325 and QD326 (FIG. 3C). These results demonstrate that ROS accumulation is the primary mechanism for cytotoxicity of QD compounds. However, NAC treatment did not completely block the cytotoxicity of QDs and $H_2O_2$, suggesting additional cellular effects responsible for the inhibition of cell proliferation.

Example III

This example demonstrates that QD compounds induce oxidative stress and unfolded protein response.

Figure 8A:
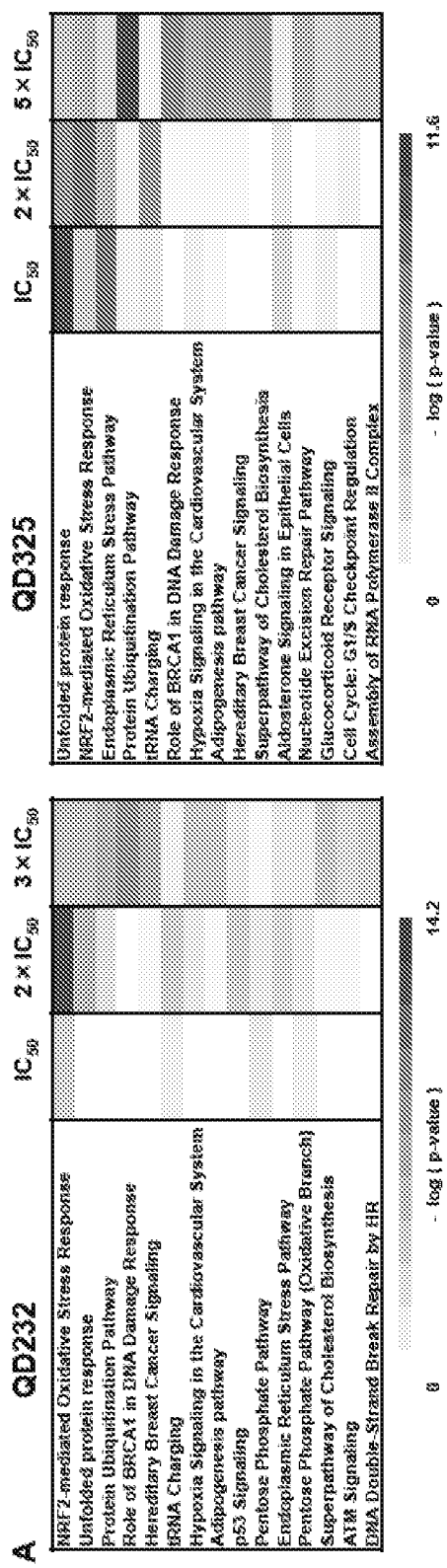
FIG. 8A-C: QD compounds induce cellular responses for oxidative stress and unfolded protein response. A) Top 15 canonical pathways regulated by QD232 or QD325 treatment as revealed by IPA analysis of Bru-seq data. MiaPaCa-2 cells were treated by QD232 (at 1, 2 or 3 times IC$_{50}$) or QD325 (at 1, 2 or 5 times IC$_{50}$) for 4 h. Nascent RNA was labeled by bromouridine in the last 30 min of treatment, isolated, and subjected to next generation sequencing. B) Transcription of oxidative stress responsive genes NQO1 and HMOX1 was upregulated by QD232 or QD325 treatment in MiaPaCa-2 cells dose dependently. C) Transcription of unfolded protein response target genes DDIT3 and HSPA5 was upregulated by QD232 or QD325 treatment in MiaPaCa-2 cells.

A bromouridine labeled RNA sequencing (Bru-seq) technique was used to better characterize molecular mechanisms of these novel agents. Bru-seq is able to capture real-time synthesis of the nascent RNA, so as to provide information on global gene transcription without interference by RNA stability or biased gene selection (Paulsen et al., 2014, Paulsen et al., 2013). Similar transcription signatures were observed for QD232 and QD325 through Ingenuity Pathway Analysis (IPA) or Gene Set Enrichment Analysis (GSEA) (FIGS. 4, 5, 6, 7), implying similar mechanisms of action for the two compounds. Profiling of all genes with >1.5-fold change in expression upon treatment of QD232 or QD325 identified NRF2-mediated oxidative stress response and unfolded protein response (UPR) as key pathways implicated in drug action (FIG. 8A).

NRF2 (NFE2L2, nuclear factor erythroid-derived 2 like 2) is a transcription factor from the cap'n'collar (CNC) family that plays a pivotal role in response to oxidative and electrophilic stresses by regulating transcription of detoxifying enzymes (Jaiswal, 2004). Upon oxidative challenges, Nrf2 dissociates from its cytosolic inhibitor protein KEAP1, translocates to the nucleus (Dinkova-Kostova et al., 2002, Zhang and Hannink, 2003), and activates transcription of antioxidant genes containing the ARE (antioxidant response element) or the MARE (MAF recognition element) cis-acting enhancer.

Figure 8B:
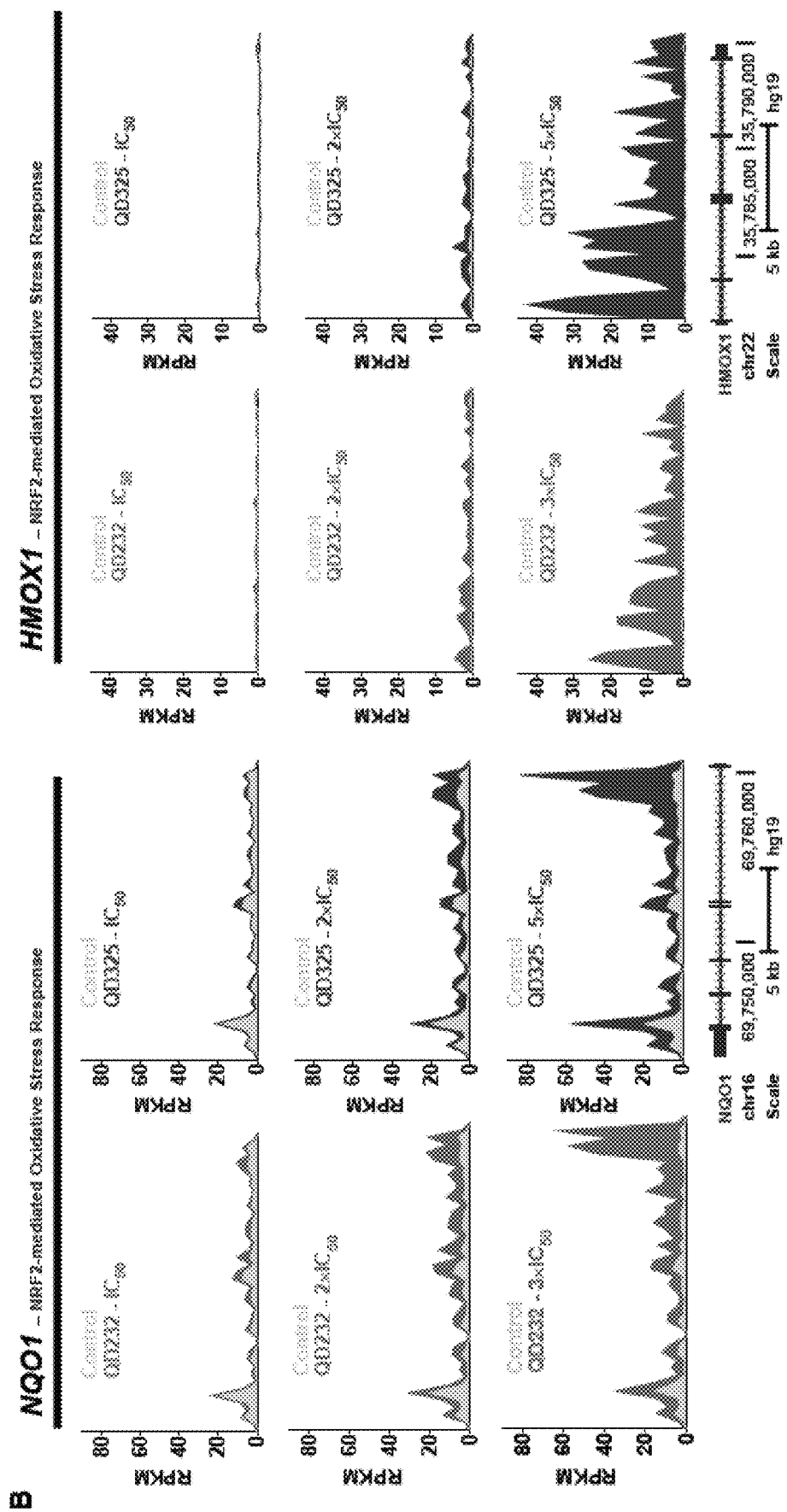

NQO1 and HMOX1 are two target genes in the NRF2 signaling pathway that mediate responses to oxidative stress (Alam et al., 1999, Nioi et al., 2003). NQO1 encodes the flavoprotein NAD(P)H:quinone oxidoreductase 1 that catalyzes the two-electron reduction of quinones to hydroquinones and exhibits chemo protective effects (Ross et al., 2000, Dinkova-Kostova and Talalay, 2000). HMOX1 encodes heme oxygenase 1 (HO-1), whose antioxidant properties arise from degradation of the pro-oxidant heme and production of antioxidant bilirubin from biliverdin (Choi and Alam, 1996). As revealed by Bru-seq, synthesis of NQO1 and HMOX1 RNAs is dose-dependently upregulated by QD232 and QD325 treatment (FIG. 8B).

UPR comprises three different pathways regulated respectively by the ER trans-membrane proteins inositol-requiring enzyme 1a (IRE1a), activating transcription factor 6 (ATF6), and protein kinase RNA-like endoplasmic reticulum kinase (PERK) (Shamu and Walter, 1996, Harding et al., 2000, Haze et al., 1999). During ER stress, misfolded proteins in the ER lumen bind to the ER chaperone 78-kDa glucose regulated protein (GRP78) competitively, leading to activation of IRE1a, ATF6 and PERK and downstream responses to UPR (Hetz, 2012). Depending on the severity and duration of the ER stress, the UPR can function as a pro-survival mechanism and restore homeostasis, or trigger apoptosis when the stress burden is beyond the capacity of this adaptive response (Kim et al., 2006, Verfaillie et al., 2013).

Figure 8C:
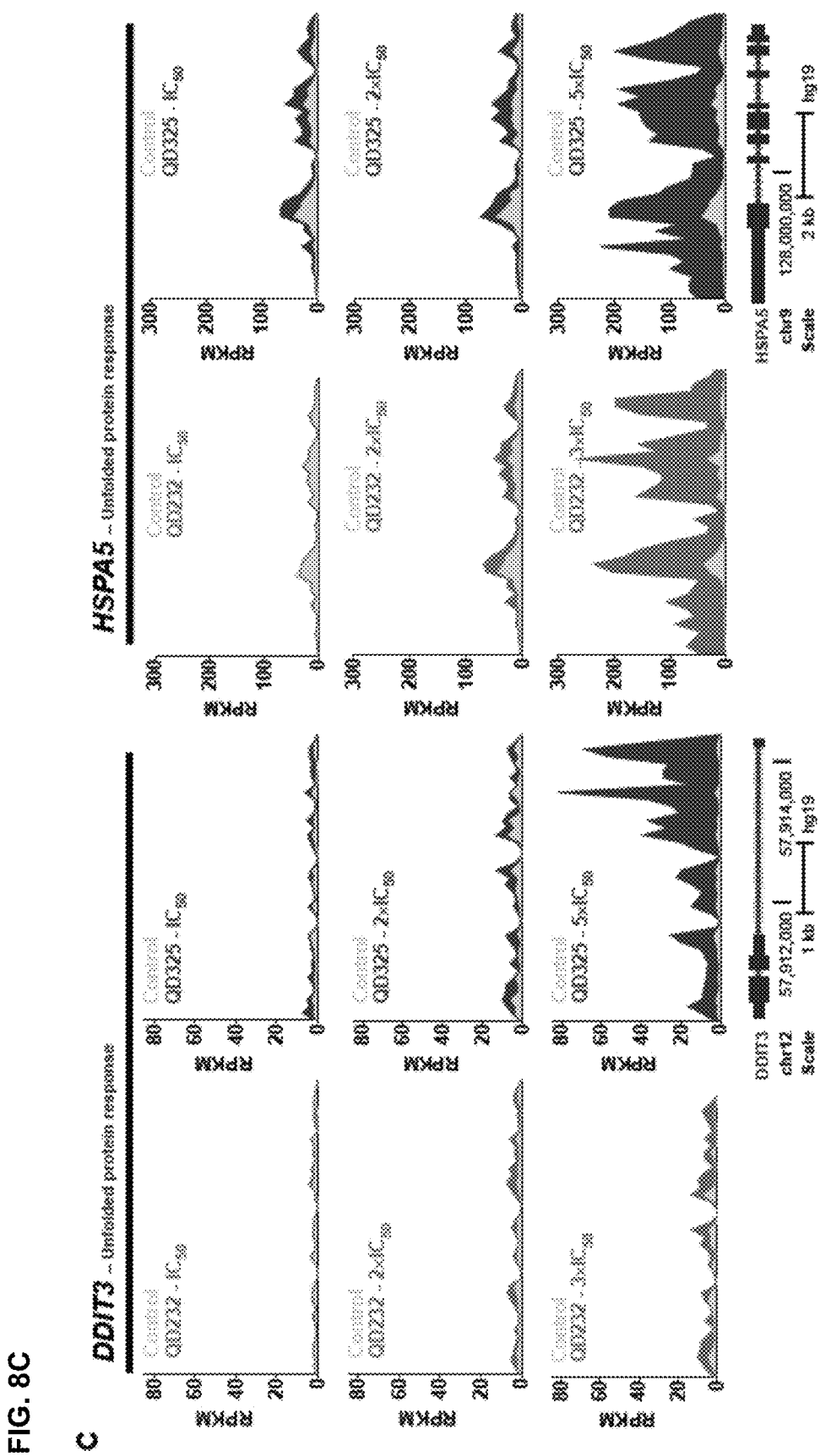

DDIT3 and HSPA5 are representative genes of UPR signaling. HSPA5 encodes GRP78, the master regulatory protein of ER stress. DDIT3 is a downstream target gene that responds to all three arms of UPR. As a transcription factor, the DDIT3 gene product CHOP (CCAAT-enhancer-binding protein homologous protein) promotes apoptosis under prolong ER stress (Nishitoh, 2012, Oyadomari and Mori, 2004). Transcription of the two stress responsive genes DDIT3 and HSPA5 is significantly increased by QD232 or QD325 treatment dose dependently (FIG. 8C).

Figure 9:
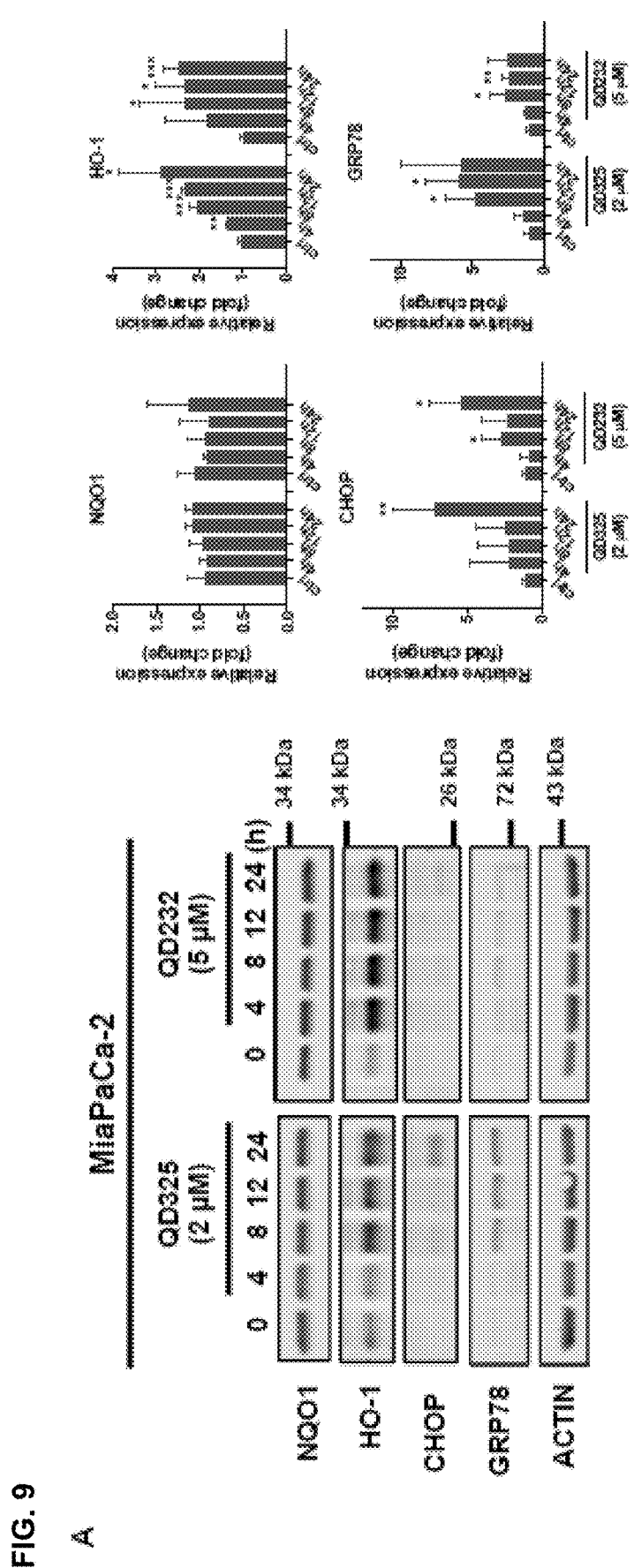
FIG. 9A-C: QD compounds induce protein expression of target genes for oxidative stress and unfolded protein response. Expression levels of oxidative stress responsive proteins NQO1, HO-1 and unfolded protein response target proteins CHOP and GRP78 were regulated to different extents by QD232 or QD325 treatment time dependently in A) MiaPaCa-2, B) Panc-1 and C) BxPC-3 cells. Protein levels were quantified by ImageJ and normalized to respective loading controls. Data on quantification plots represent Mean±SD from three independent experiments. P values were calculated using student's t-test. *, p<0.05; , p<0.01, *, p<0.001.
Figure 9:
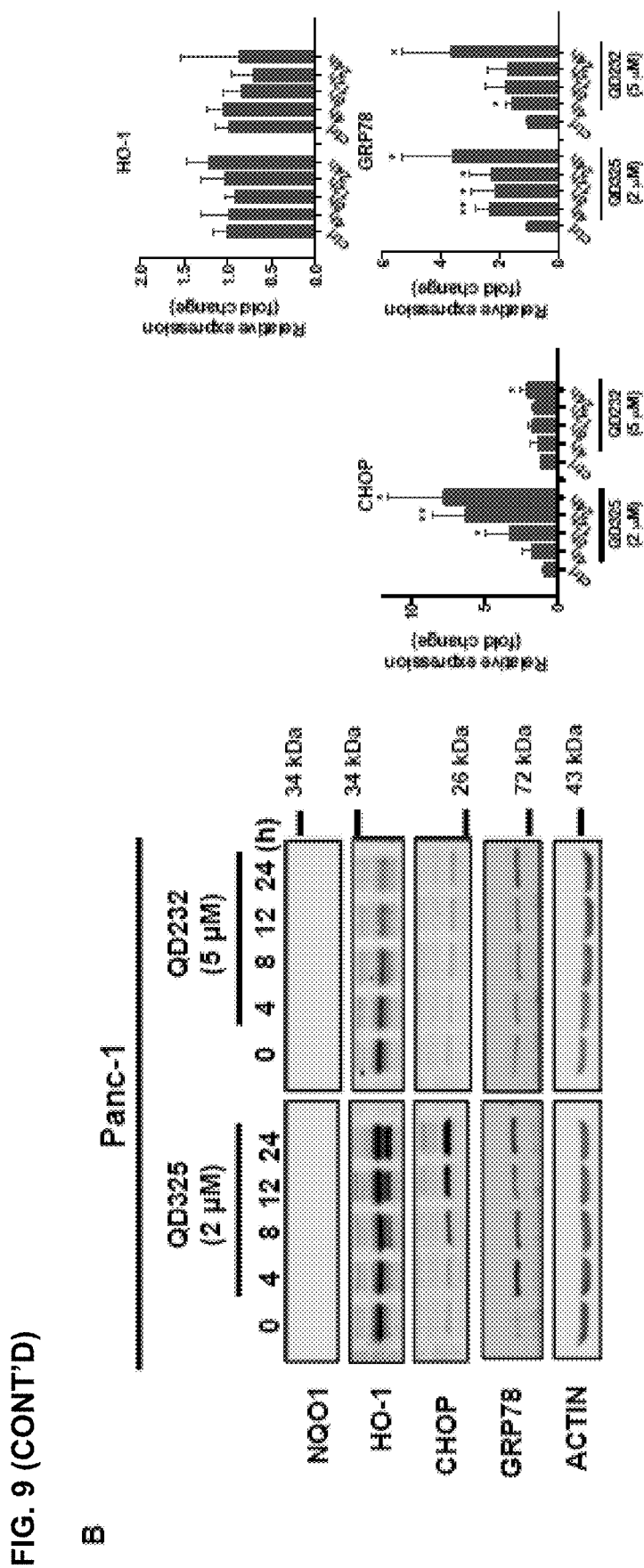
Figure 9:
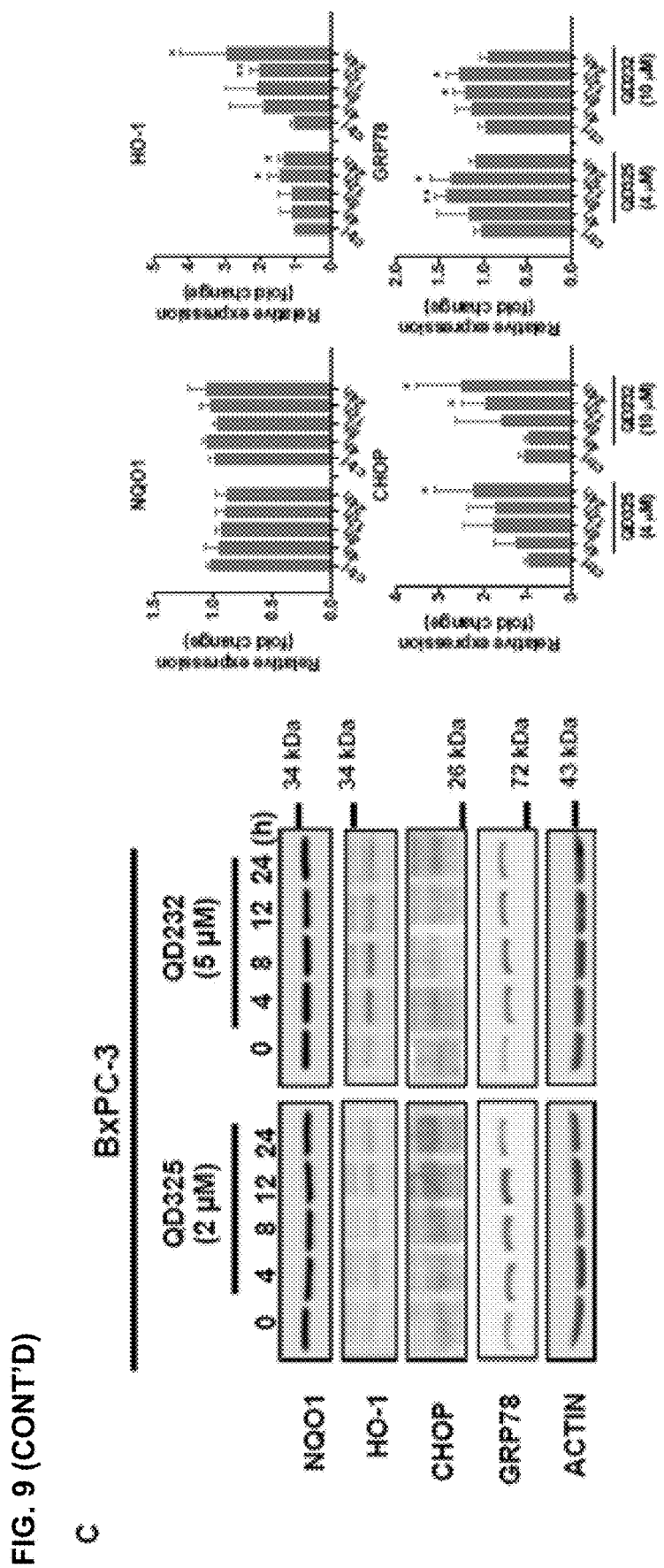

Upregulation of mRNA synthesis is further translated into increased protein levels of these major stress responsive genes. Increased protein levels of CHOP and GRP78 in MiaPaCa-2, Panc-1, and BxPC-3 cells was observed (FIG. 9A-C) confirming UPR as a major mechanism. For the oxidative responsive genes, HO-1 was upregulated by QD treatments in MiaPaCa-2 and BxPC-3, while no significant change was detected in Panc-1. Of note, NQO1 gene is deleted in Panc-1 cells, and no expression of the gene was observed in this cell line. In MiaPaCa-2 and BxPC-3, NQO1 showed high basal expression levels, thus no further induction were observed. These results suggest that oxidative stress responses are more sensitive in MiaPaCa-2 and BxPC-3 cells.

Figure 4:
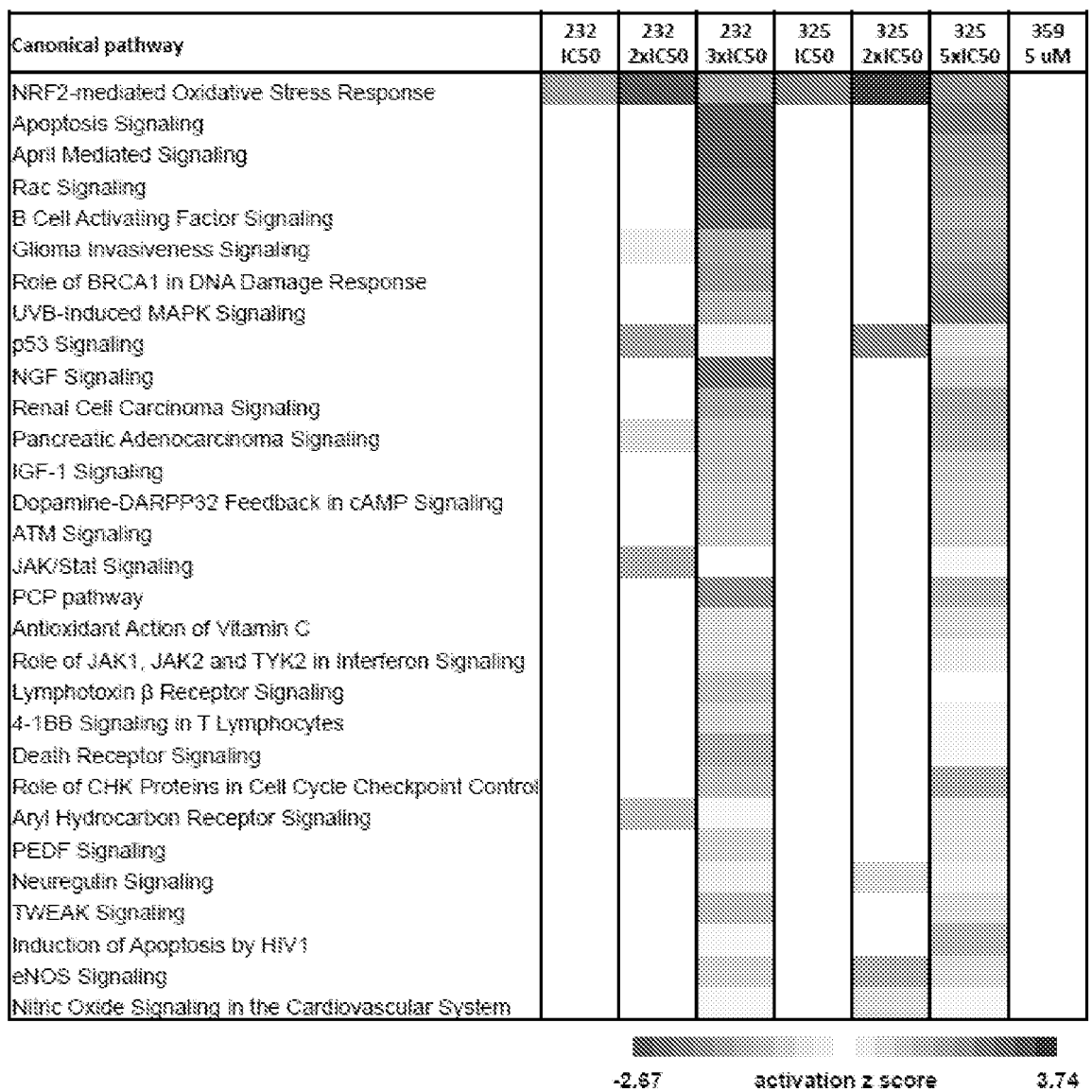
FIG. 4 shows the top 30 canonical pathways affected by QD compound treatments as shown with IPA (z score). List was generated by IPA based on activation z score, which indicates activation/inhibition of specific pathway.
Figure 5:
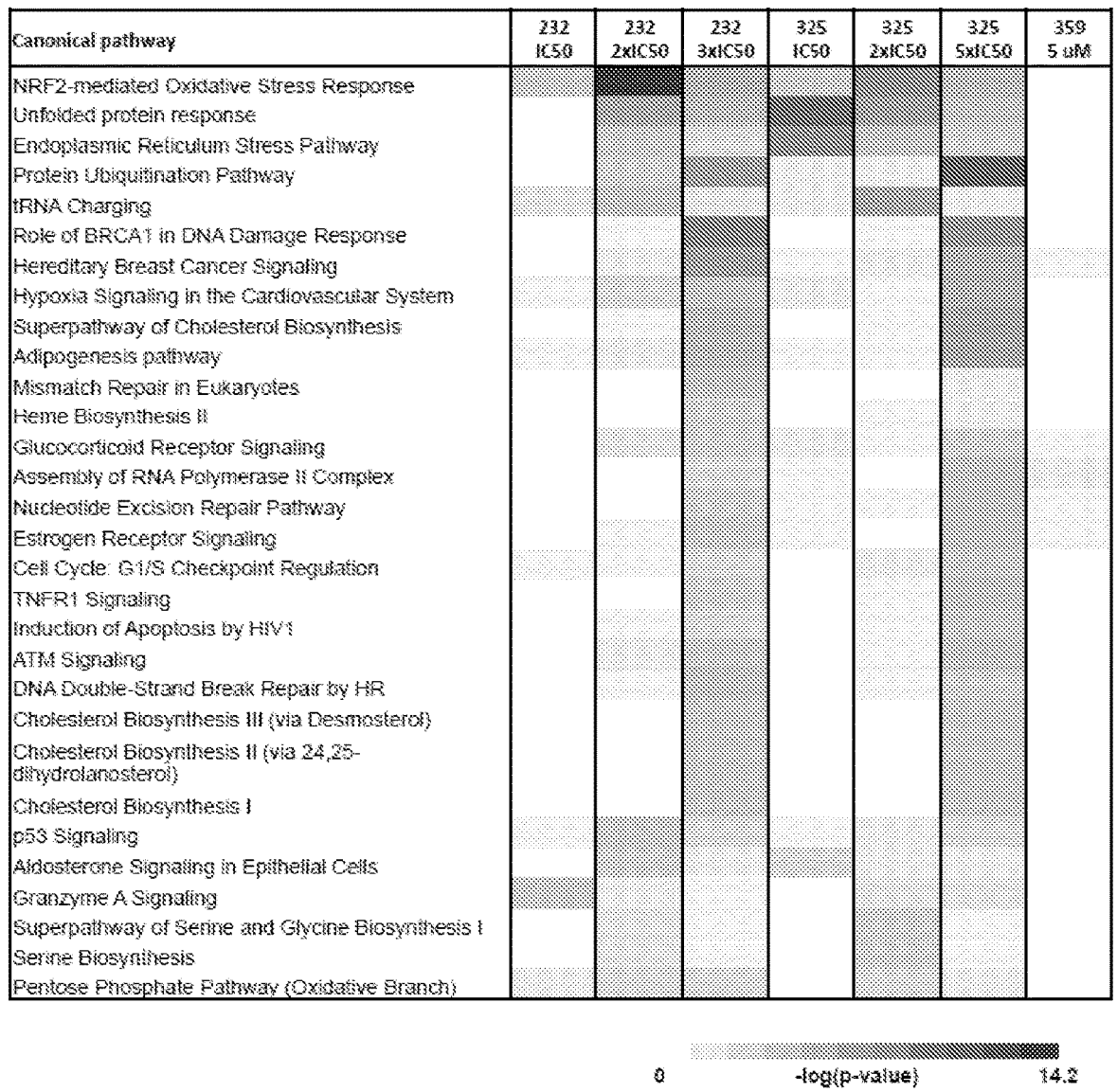
FIG. 5 shows the top 30 canonical pathways affected by QD compound treatments as shown with IPA (p value). List was generated by IPA comparison analysis based on p value. List was sorted by hierarchical clusters.
Figure 6:
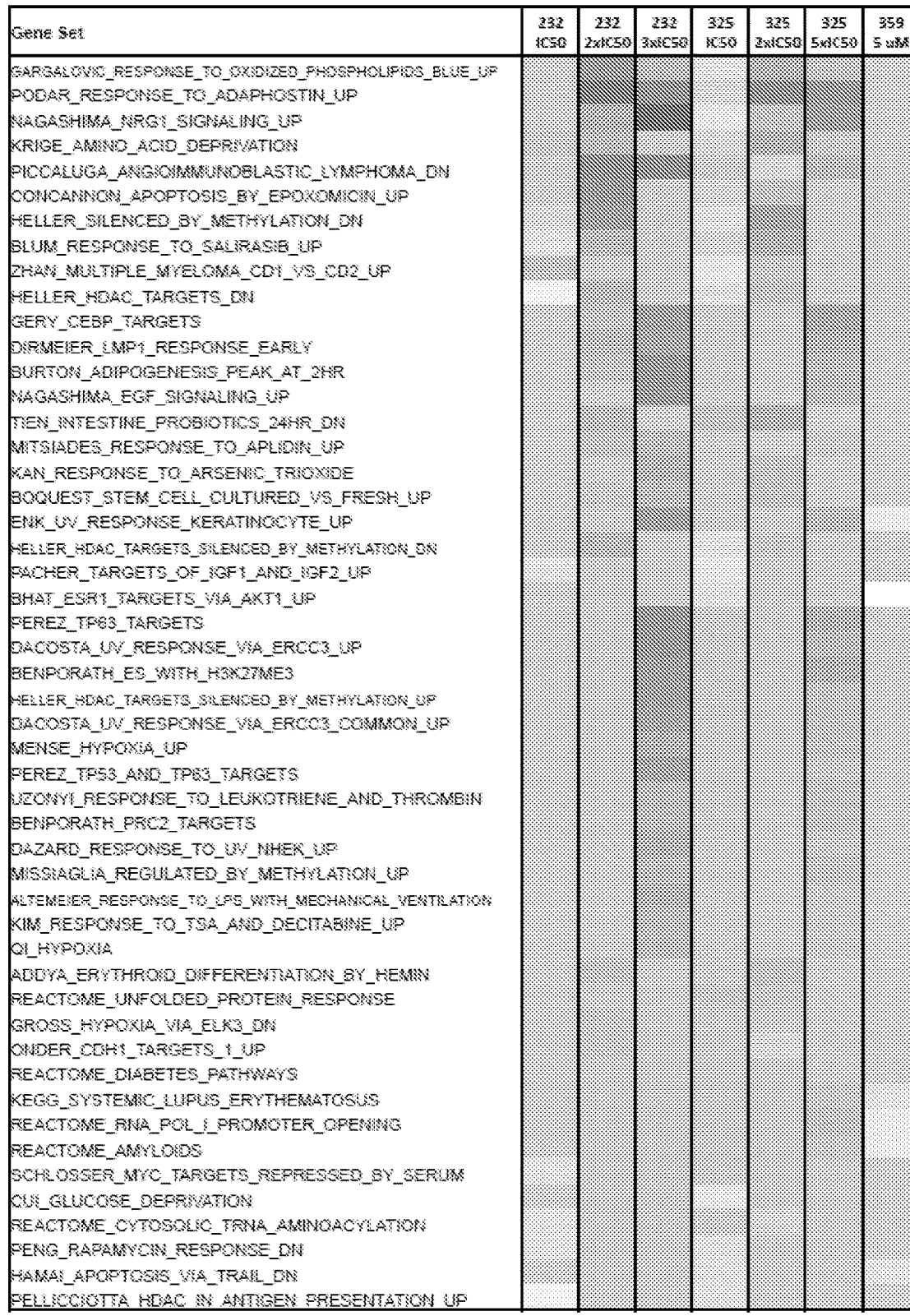
FIG. 6 shows the top 50 gene sets up regulated by QD compound treatments as shown with GSEA. Top 30 gene sets (FDR q-value <0.1) affected by each QD treatment were selected and compiled. The compiled list across all treatments was sorted according to sum of normalized enrichment score (NES). Top 50 gene sets are shown from the sorted list. Cells in gray indicates blank, which means the specific gene set was not among the top 30 gene sets affected by the indicated treatment. Heat map was generated based on NES.
Figure 7:
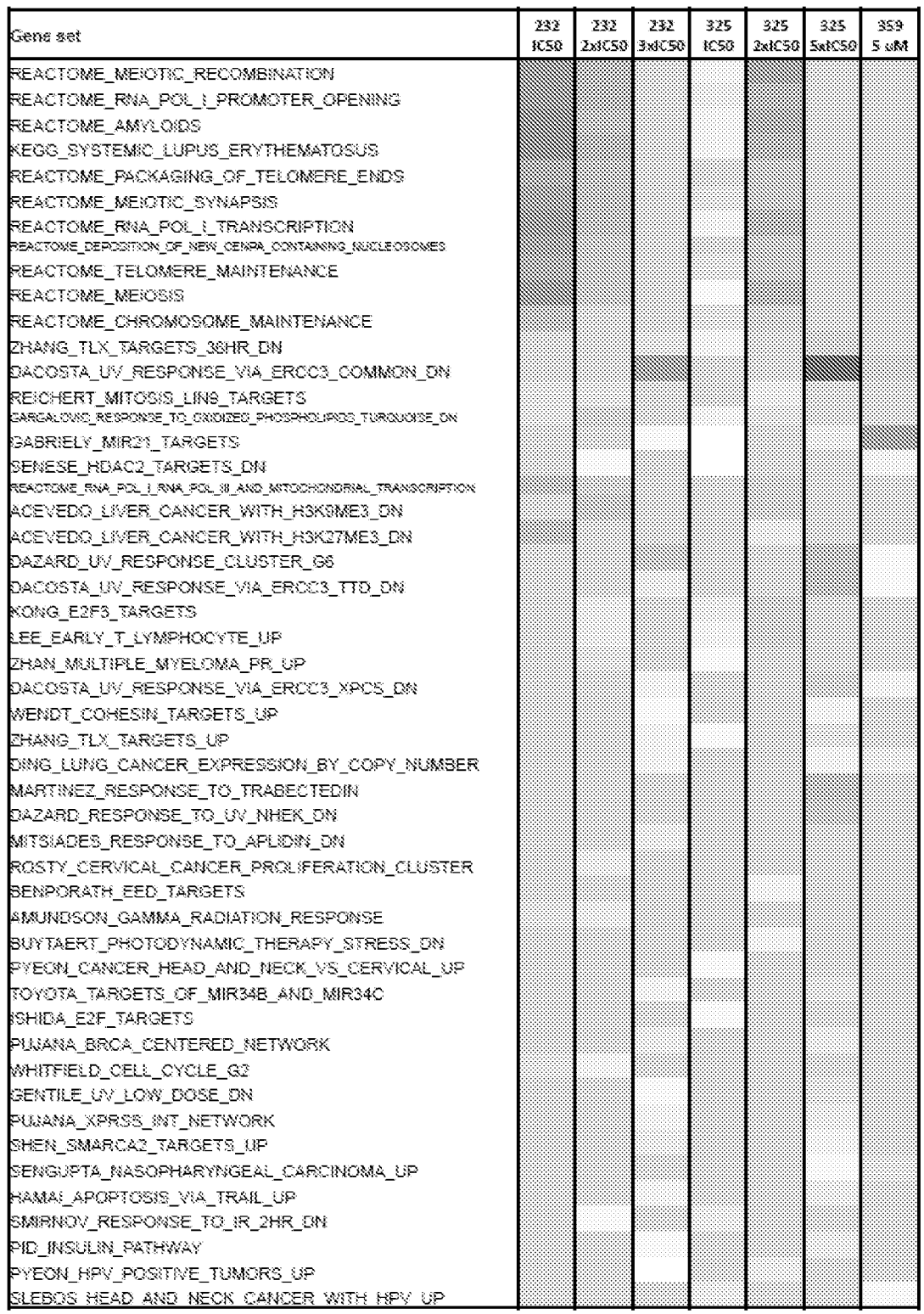
FIG. 7 shows the top 50 gene sets down regulated by QD compound treatments as shown with GSEA. Top 30 gene sets (FDR q-value <0.1) affected by each QD treatment were selected and compiled. The compiled list across all treatments was sorted according to sum of normalized enrichment score (NES). Top 50 gene sets are shown from the sorted list. Cells in gray indicates blank, which means the specific gene set was not among the top 30 gene sets affected by the indicated treatment. Heat map was generated based on NES.
Figure 7:
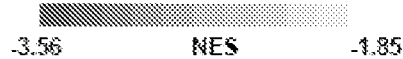

While response to oxidative stress was triggered as a result of ROS accumulation to restore redox homeostasis, switches in stress signaling directs cells down the apoptosis path for elimination when the stress is beyond repair. IPA analysis suggests significant activation of apoptosis signaling at higher concentration of QD232 (3 times $IC_{50}$) or QD325 (5 times $IC_{50}$) after 4 h treatment (FIG. 4).

Exhibit IV

This example demonstrates that QD compounds inhibit transcription of mtDNA from the D-loop.

Figure 10:
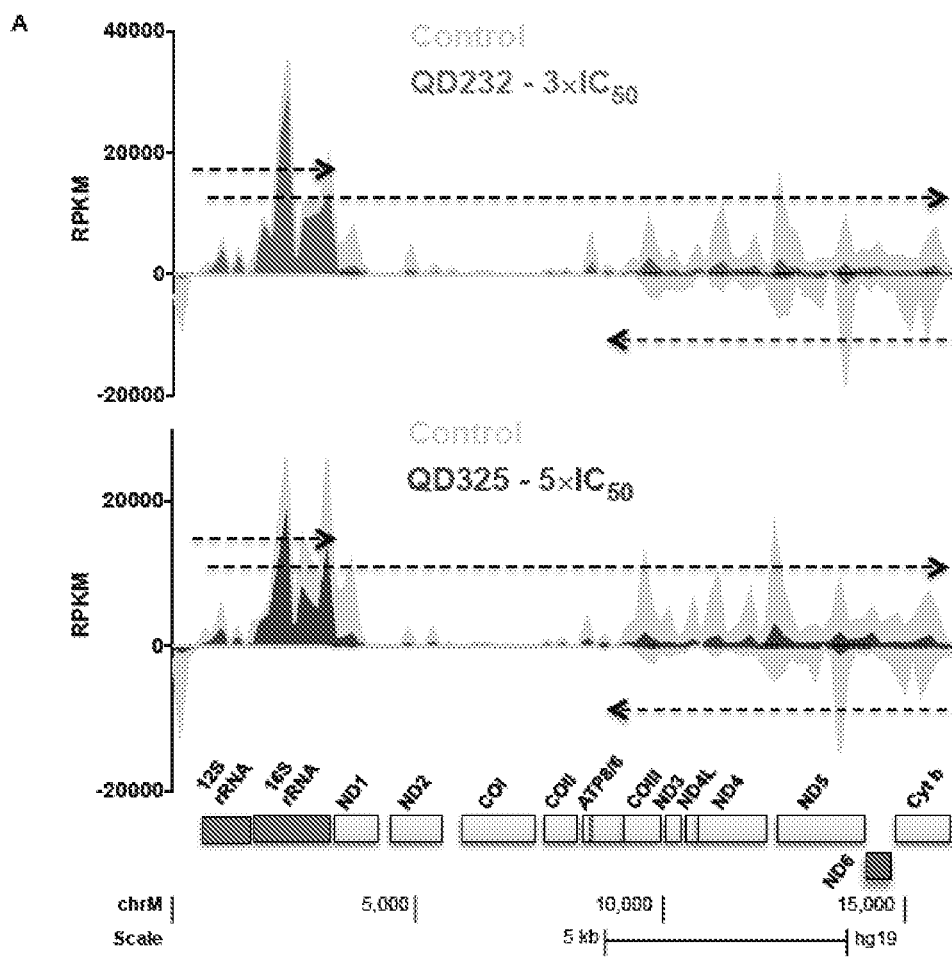
FIG. 10A-B: QD compounds inhibit transcription of mitochondrial genome. A) Nascent RNA synthesis of MiaPaCa-2 cells was inhibited by 4 h QD232 (at 6.9 µM) or QD325 (at 5.0 µM) treatment. Top forward arrows represent transcripts from the heavy strand. While the shorter arrow represents the shorter transcript regulated by the H1 promoter, the longer arrow represents transcript regulated by the H2 promoter that covers full length of the mitochondrial genome. Bottom reverse arrow represents the light strand transcript regulated by the L promoter. Signal from control is shown in yellow, signal from QD232 treated sample is shown in blue, and signal from QD325 treated sample is shown in red. The full-length transcripts from both heavy and light strands are further processed into functional tRNA, rRNA and mRNA molecules, whose corresponding genes are shown at the bottom of the panel. B) Protein (COXIII) expression levels of the mitochondrial gene COIII are decreased by treatment of QD compounds in MiaPaCa-2. Protein levels were quantified by ImageJ and normalized to respective loading controls. Data on quantification plots represent Mean±SD from three independent experiments. P values were calculated using student's t-test. *, p<0.05; **, p<0.01.
Figure 10:
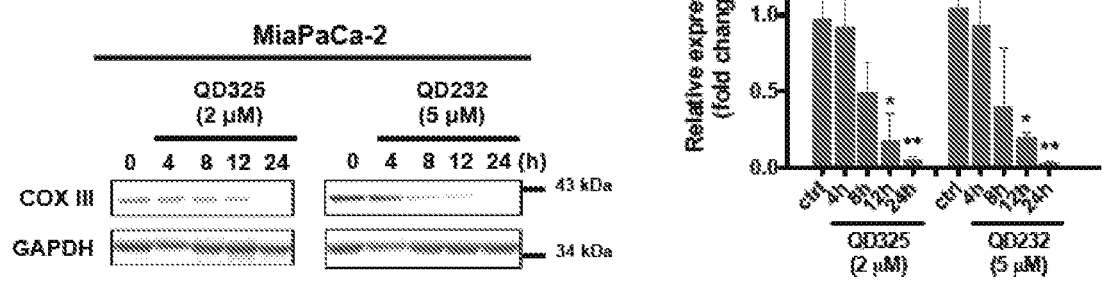
Figure 11A:
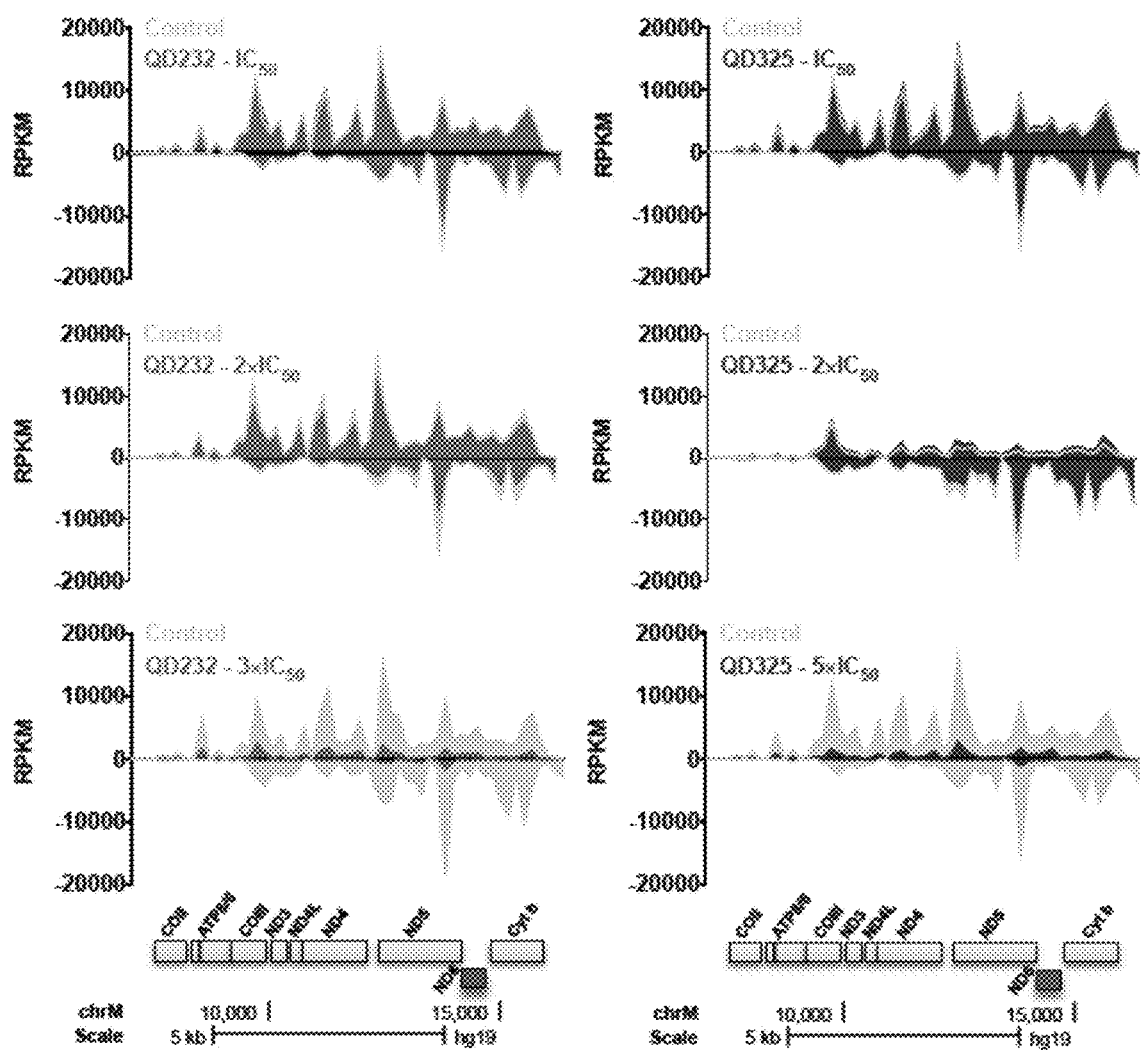
FIG. 11A-C shows QD232 or QD325 treatment selectively inhibits synthesis of mtDNA transcripts. A) Nascent RNA synthesis of MiaPaCa-2 cells was inhibited by 4 h QD232 (at 6.9 µM) or QD325 (at 5.0 µM) treatment. Top curves represent reads mapped to the heavy strand transcript regulated by the HSP2 promoter, bottom curves represent reads mapped to the light strand transcript regulated by the LSP promoter. Signal from control is shown in yellow, signal from QD232 treated sample is shown in blue, and signal from QD325 treated sample is shown in red. The full-length transcripts from both heavy and light strands are further processed into functional tRNA, rRNA and mRNA molecules, whose corresponding genes are shown at the bottom of the panel. B) Relative levels of mtDNA are decreased by 6 h treatment of active QD compounds in MiaPaCa-2. mtDNA content is calculated by comparing mtDNA 12S rRNA to genomic 18S rRNA, and data is normalized to controls. Data is shown as Mean±SD from three independent experiments. C) Relative levels of mtDNA are decreased time dependently after QD232 or QD325 treatment in MiaPaCa-2.
Figure 11B:
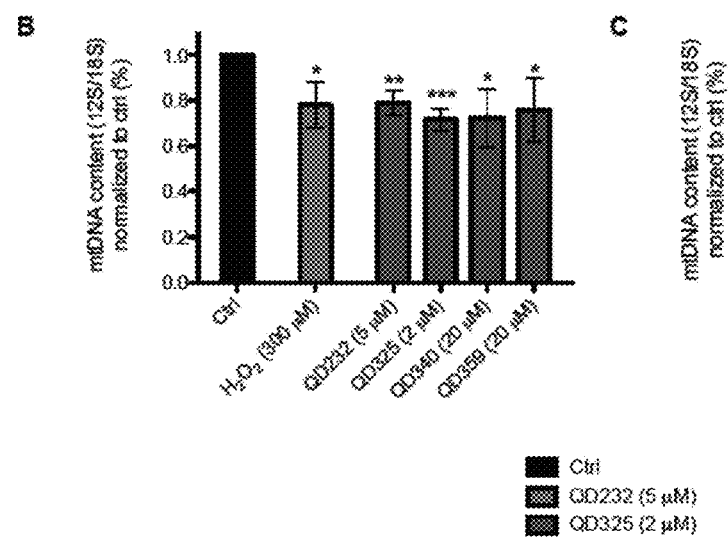
Figure 11C:
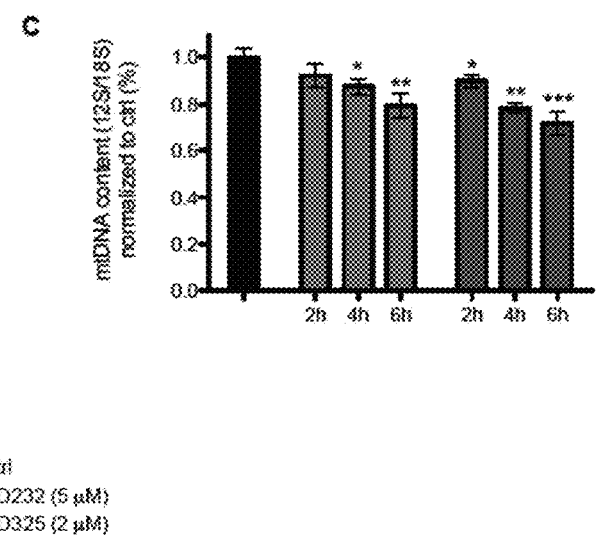

Mitochondria play an important role in redox homeostasis in mammalian cells. Deregulation of mitochondrial genes can lead to interruption of the OXPHOS process and accumulation of ROS. Mitochondrial DNA (mtDNA) encodes 13 genes that possess important functions in the electron transport chain. The double-stranded circular DNA comprises the guanine-rich heavy strand and the cytidine-rich light strand. Using Bru-seq, significant inhibition of mtDNA transcription was observed after a 4-hour treatment with QD compounds at higher concentrations (FIG. 10A; FIG. 11). Both compounds decreased COX III protein levels confirming decrease in mtDNA gene products (FIG. 10B). These results strongly suggest disruption of mitochondrial function.

Lower levels of transcription could be a result of decreased DNA templates or effects on transcription efficiency. Using mtDNA specific primers, the mitochondrial DNA content among different treatments was compared. A small but significant decrease in mtDNA content was observed 6 hours after $H_2O_2$ or QD compound treatment (FIG. 11). Downregulation of mtDNA content is a time dependent effect. This decrease in DNA templates could be caused by accumulation of ROS, as suggested by $H_2O_2$ treatment, leading to mtDNA damage and degradation (Shokolenko et al., 2013).

The D-loop (displacement loop) is a noncoding area of the mtDNA composed of a short three-strand structure required for the regulation of mtDNA replication and transcription. This region contains promoters (HSP and LSP) for transcription from the 2 strands of mtDNA and the mtDNA replication origin ($O_H$). mtDNA alterations in D-loop region have been reported as a frequent event in lung, hepatocellular, colorectal and cervical cancers (Guleng et al., 2005, Kabekkodu et al., 2014, Suzuki et al., 2003, Wheelhouse et al., 2005). Cancer patients with D-loop mutations, or in particular with heteroplasmy of the mtDNA D-loop polymorphism, have significantly poorer prognosis (Lievre et al., 2005, Ye et al., 2014).

QDs selectively inhibited the transcription of mtDNA from both the heavy strand promoter HSP2 (top long arrow in FIG. 10A) and the light strand promoter LSP (bottom arrow) on D-loop, thus inhibiting the expression of mitochondrial genes that are essential for mitochondrial oxidative phosphorylation. However, the activity of the heavy strand promoter HSP1 (top short arrow), which regulates transcription of 12s rRNA and 16s rRNA, was not affected by QDs. To provide additional proof in support of the findings, similar studies were performed using UV, a well-established ROS-inducer. No significant effect of UV on transcription from mitochondrial promoters was found. Similarly, no such effect was observed with additional 16 novel drugs and the DNA topoisomerase I inhibitor camptothecin. Thus, the Bru-seq data suggest that the unique mechanism by which QD232 and QD325 inhibit mitochondrial function and induce ROS may be at least partially related to blockade of transcription from the mitochondrial genome.

Exhibit V

This example demonstrates that QD325 Delays Tumor Growth without Systemic Toxicity.

QD232, QD325, QD326 all showed similar cytotoxicity in MiaPaCa-2 and a gemcitabine-resistant cell line MiaPaCa-2-GR (Ali et al., 2010) (Table 4). In the HPV16-E6E7 gene immortalized pancreatic cell line, HPDE (Ouyang et al., 2000), gemcitabine produces similar $IC_{50}$ values as in MiaPaCa-2 cells, while the most potent QD325 showed 3-fold selectivity for MiaPaCa-2 (Table 4). In MiaPaCa-2 derived-xenograft in NOD/SCID mice, QD325 (5 mg/kg) treatment significantly delayed growth of tumors in the treatment period of 44 days. On day 44, when average tumor size in control group was 1291±168 mm$^3$, it was only 308±72 mm$^3$ (p=2.1E6) for QD325 treatment group (FIG. 12A).

Figure 12:
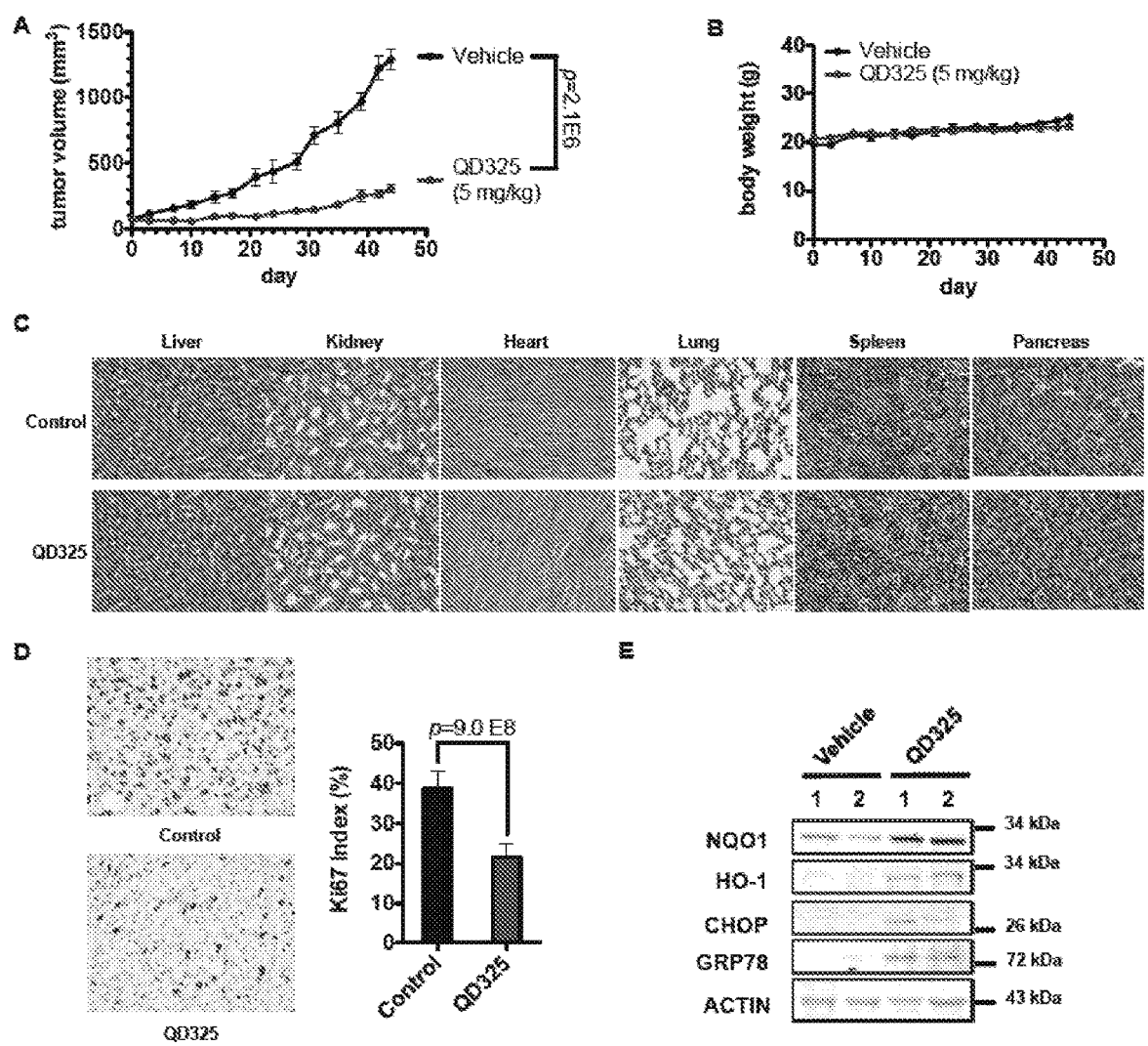
FIG. 12A-E: QD325 inhibits tumor growth of MiaPaCa-2 xenograft without systemic toxicity. A) QD325 treatment at 5 mg/kg inhibits growth of MiaPaCa-2 xenograft in NOD/
Figure 13:
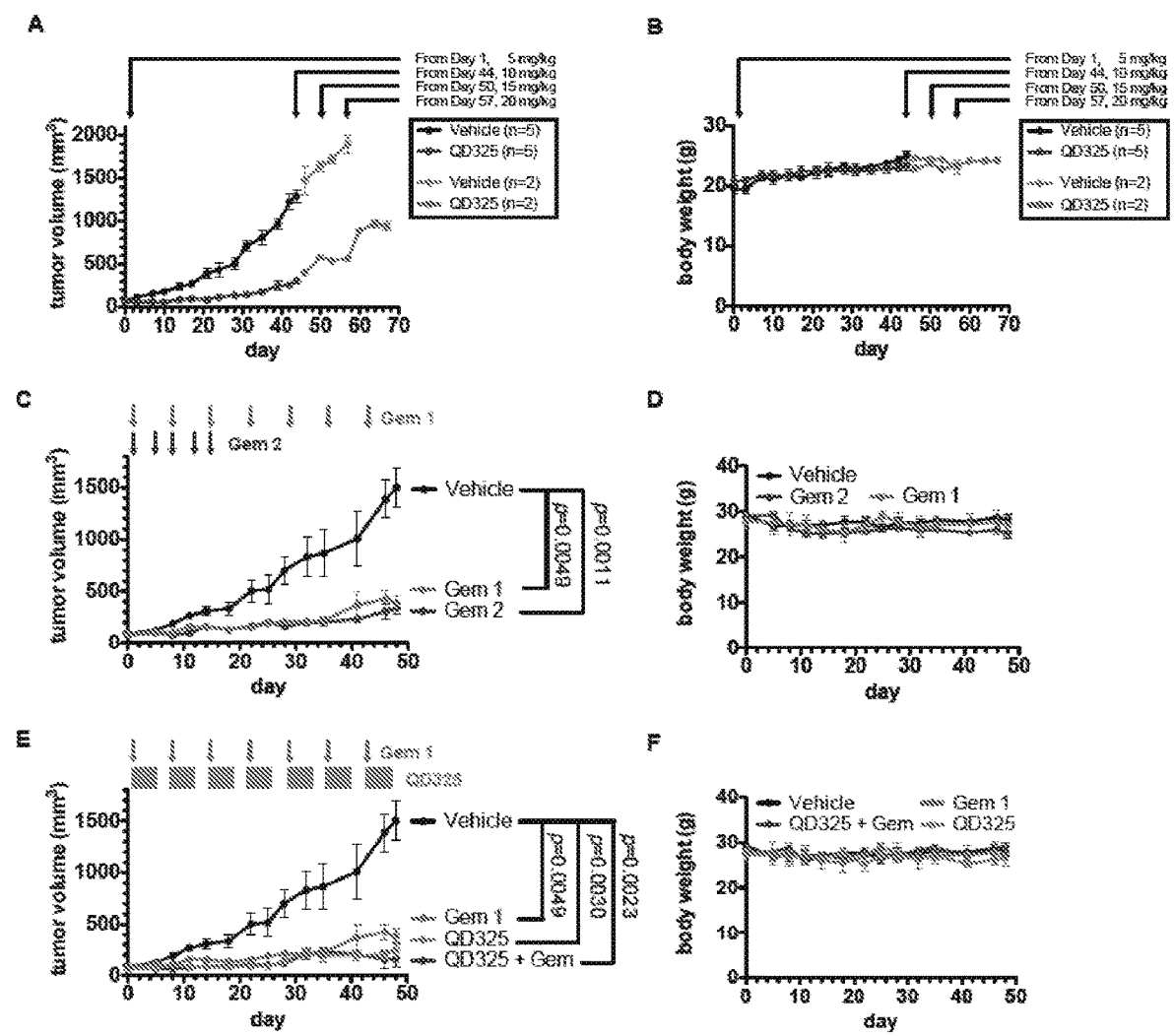

No symptoms of gross toxicity such as weakness, weight loss or lethargy were observed in any treatment group (FIG. 12B). H&E stained organ sections of liver, kidney, heart, lung, spleen and pancreas did not reveal major histopathological changes, further confirming in vivo safety of QD325 (FIG. 12C). Following the 44-day treatment, two mice were kept on each group to evaluate efficacy and safety of QD325 at higher doses. While tumors in the control group exhibited rapid growth, QD325 treatment was able to delay growth of the tumors, and no systemic toxicity was observed at doses as high as 20 mg/kg (FIG. 13A-B).

In line with the tumor growth inhibition, QD325 treatment decreased Ki67 levels in tumor tissues, suggesting inhibition of cell proliferation (FIG. 12D). To further evaluate the mechanisms of action of QD325 in vivo, protein levels of stress responsive markers in tumor lysates were examined. NQO1, HO-1, CHOP and GRP78 protein levels were significantly upregulated in QD325 treated tumors compared to vehicle controls, further confirming induction of oxidative stress and UPR as major mechanisms of action for QD325 in pancreatic cancer models (FIG. 12E).

Gemcitabine is a key component of the standard of care treatment for pancreatic cancer patients. Unfortunately, inherent or acquired resistance to gemcitabine represents a major challenge for treatment of this disease. With this consideration, the potential of administering QD325 as a single agent or in combination with gemcitabine was explored.

In mice studies, gemcitabine is usually given at high doses (40-160 mg/kg) twice weekly. Considering its low tolerance in NOD/SCID mice, antitumor activity of two different gemcitabine treatment schedules in a MiaPaCa-2 xenograft model in this mouse strain was compared: 1) 15 mg/kg once a week for 48 days; 2) 15 mg/kg twice a week for the first 15 days. Similar antitumor activity was achieved by both schedules (FIG. 13C). In both cases, gemcitabine was well tolerated and no weight loss was observed (FIG. 13D). Therefore, schedule 1 was used for comparison of efficacy with QD325 at 5 mg/kg and the combination of gemcitabine and QD325. QD325 was given at 5 mg/kg five times a week and gemcitabine was given at 15 mg/kg once a week (FIG. 13E). At the end of the 48-day treatment period, average tumor size was 1503±189 mm$^3$ for the control group, 387±74 mm$^3$ (p=0.0049) for gemcitabine, 248±72 mm$^3$ (p=0.0030) for QD325, and 163±83 mm$^3$ (p=0.0023) for the combination of gemcitabine and QD325 (FIG. 13E). Single agent treatment with QD325 at 5 mg/kg showed similar anti-tumor activity as gemcitabine. In this experiment, both gemcitabine and QD325 greatly inhibited tumor growth as single agents. Importantly, the combination was well tolerated and no weight loss was observed in any of the treatment groups, suggesting a reasonable safety profile of the drug combination (FIG. 13F).

Example 6

This example demonstrates the general procedure for preparation of compounds QD325-340, 353-359 and intermediates.

The synthesis of compounds QD325-338, 353-357 (Table 2) was carried out using Bracher's methodology, and according with a previously reported procedure, with slight modification.

Scheme 1 illustrates the synthesis of the key synthone QD323 from the readily available dimethoxybenzaldehyde 1. Nitration of compound 1 with concentrated nitric acid in the presence of acetic anhydride under simple magnetic stirring afforded the 3,6-dimethoxy-2-nitrobenzaldehyde (2) in good yield. This regioisomer was converted to the diformamido-derivative 3 by exposition to gaseous HCl. Compound 3 was then cyclized to dimethoxyquinazoline 4 by treatment with zinc powder and acetic acid. Final oxidation by cerium ammonium nitrate resulted in the production of quinazoline-5,8-dione QD323. Regioselective substitution of QD323 with appropriate aminoacylbenzenes in the presence of Ce(III) ions gave QD325-338, 353-357. (Schemes 2 and 3).

Scheme 1$^a$ Synthetic route for the preparation of the key intermediate QD323.

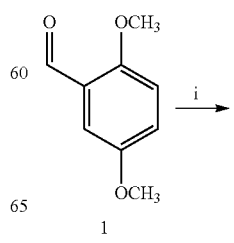

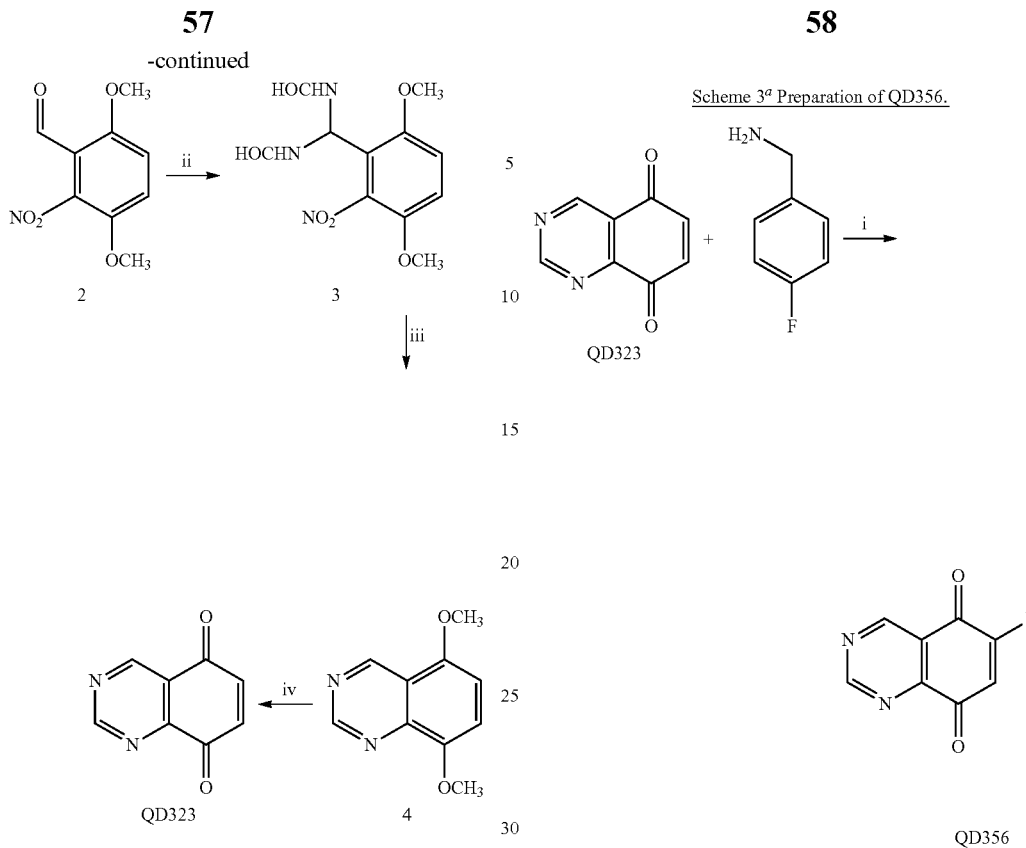

Scheme 3[a] Preparation of QD356.

[a]Reagents and conditions: (i) CeCl$_3$•7H$_2$O, abs EtOH, rt, 2 h.

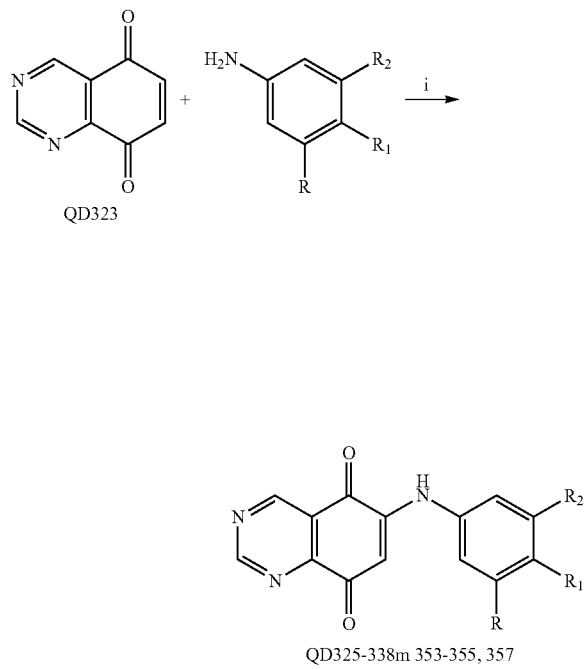

Scheme 2[a] Preparation of compounds QD325-338, 353-355, 357.

[a]Reagents and conditions: (i) CeCl$_3$•7H$_2$O, abs EtOH, rt, 1-6 h.

To evaluate a potential synergistic effect in terms of ROS modulation, conjugation of the quinazoline-5,8-dione scaffold to a triphenylphosphonium functional group was sought. More specifically, it was desired to obtain triphenylphosphonium-based model derivatives of compound QD331 and QD232. Compounds QD340 and QD359 were therefore designed by adapting a phosphine conjugation method, previously used by us. The synthesis of triphenylphosphonium-based compounds QD340 and QD359 is illustrated in Schemes 4 and 5. Initially, 3-bromopropylamine hydrobromide (5) was reacted with triphenylphosphine in refluxing acetonitrile for 16 hours, and the resulting triphenylphosphonium intermediate (6) was easily isolated after treatment with n-hexane/diethyl ether/isopropanol. Next, the 4- and 3-aminobenzamido)propyl)triphenylphosphonium bromides QD339 and QD358 were prepared by conjugating 6 with 4- or 3-aminobenzoic acid, respectively, via a standard coupling protocol using DIPEA, HBtU, DMAP, in CH$_2$Cl$_2$. Finally, QD340 and QD359 were obtained by regioselective substitution of 5 with appropriate 3-aminobenzamido)propyl) triphenylphosphonium bromides (QD339 or QD358) in the presence of Ce(III), according with the above-mentioned procedure.

Scheme 4<sup>a</sup> Preparation of QD339, 340
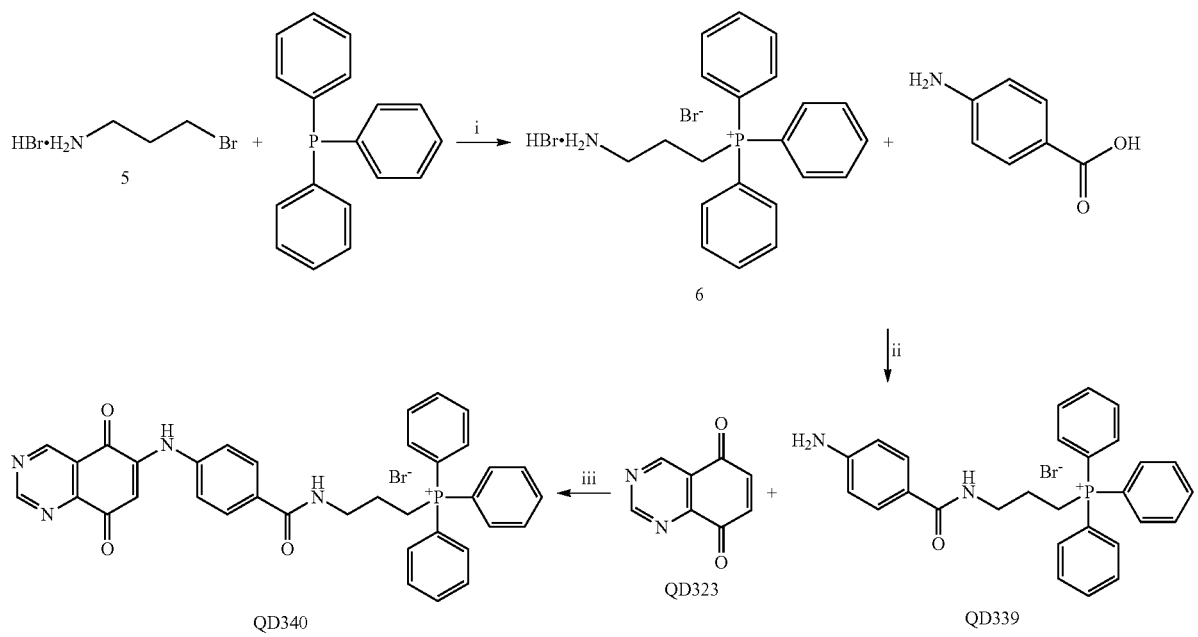
<sup>a</sup>Reagents and conditions: (i) MeCN, reflux, 16 h; (ii) 4-aminobenzoic acid, DIPEA, HBtU, DMAP, $CH_2Cl_2$, rt, 5 h; (iii) $CeCl_3 \cdot 7H_2O$, abs EtOH, rt, 2 h.
Scheme 5<sup>a</sup> Preparation of QD358, 359
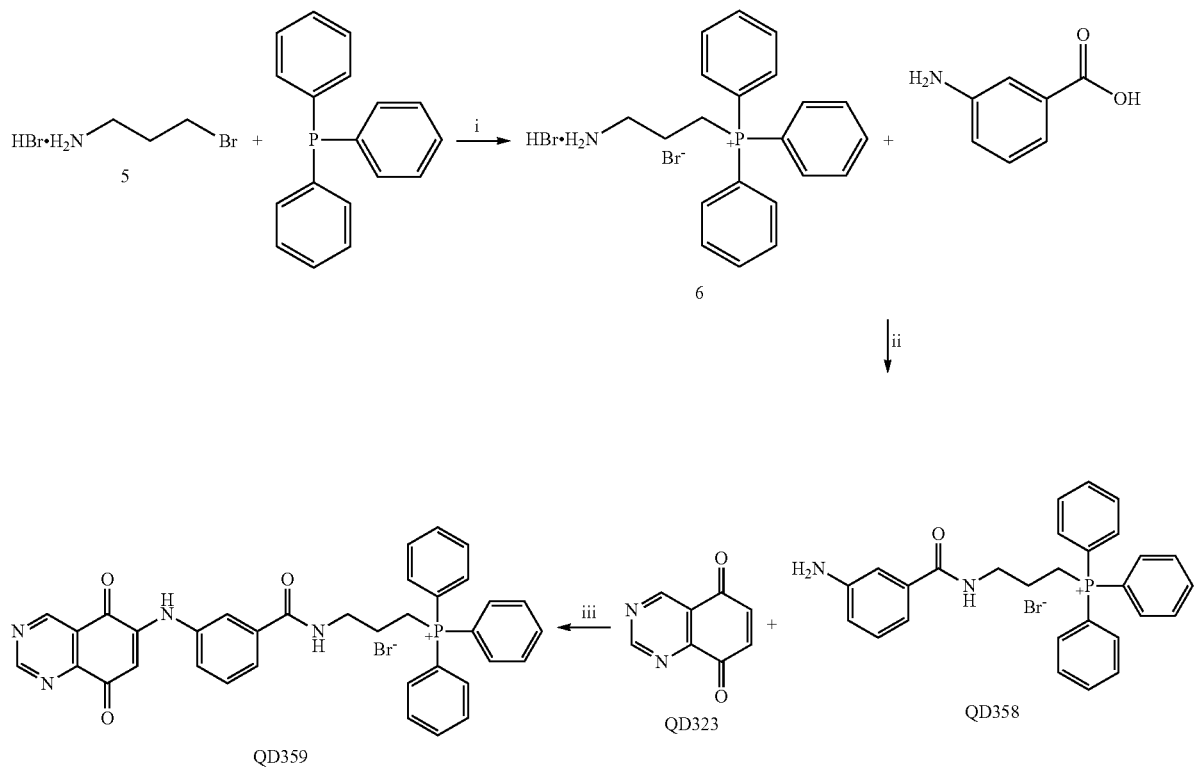
<sup>a</sup>Reagents and conditions: (i) MeCN, reflux, 16 h; (ii) 3-aminobenzoic acid, DIPEA, HBtU, DMAP, $CH_2Cl_2$, rt, 5 h; (iii) $CeCl_3 \cdot 7H_2O$, abs EtOH, rt, 1.5 h.

Preparation of 3,6-dimethoxy-2-nitrobenzaldehyde (2)

Nitric acid (8.0 mL; 179.02 mmol), acetic anhydride (8.0 mL, 84.24 mmol) and 2,5-dimethoxybenzaldehyde (1, 4.0 g, 24.07 mmol) were added at 0° C. with stirring, respectively. After 1.5 h stirring, the mixture was poured onto 20 mL ice/water. The resultant yellow solid was filtered, washed with cold water and then purified by flash chromatography on silica gel using ethyl acetate-petroleum ether (1:1) to give first the regioisomer 2,5-dimethoxy-4-nitrobenzaldehyde, and then (by further elution with only ethyl acetate) the desired compound 2. Yield: 68%. Rf=0.10 (ethyl acetate-petroleum ether 5:5); mp: 167° C. $^1$H-NMR 400 MHz (DMSO-$d_6$): δ 10.25 (s, 1H), 7.70 (d, 1H), 7.48 (d, 1H), 3.95 (s, 3H), 3.86 (s, 3H). $^1$H-NMR 400 MHz (CDCl$_3$): δ 10.39 (s, 1H), 7.30 (d, 1H), 7.12 (d, 1H), 3.97 (s, 3H), 3.89 (s, 3H). MS: m/z 211 [M]$^+$.

Preparation of N,N'-[(3,6-dimethoxy-2-nitrophenyl)methanediyl)diformamide (3)

A solution of 3,6-dimethoxy-2-nitrobenzaldehyde (2, 11.90 g, 56.35 mmol) in formamide (66.5 eq., 150 mL), heated at 40° C., was exposed to dry HCl gas (1 h) until the temperature was 80° C. Then, the solution was cooled to room temperature, and water/ice was added. Pale yellow colored precipitate was formed, which was filtered, dried and triturated with ethyl acetate and petroleum ether to yield the desired compound. Yield: 90%. Rf=0.26 (dichloromethane-methanol 9.5:0.5); mp: 255° C. $^1$H-NMR 400 MHz (DMSO-$d_6$): δ 8.67 (d, 2H), 7.92 (s, 2H), 7.28 (s, 2H), 6.77 (t, 1H), 3.88 (s, 3H), 3.82 (s, 3H). MS: m/z 283 [M$^+$].

Preparation of 5,8-dimethoxyquinazoline (4)

Zinc powder (22.9 g) was added to a suspension of N,N'-[(3,6-dimethoxy-2-nitrophenyl)methanediyl)]diformamide (3, 7.0 g, 24.71 mmol) in triturated ice (92 g) and glacial acetic acid (32 mL), under constant magnetic stirring. The reaction mixture was stirred for 2 h in ice bath, and for 4 h at room temperature. Next, the reaction mixture was dropped on cooled 50% NaOH (120 mL) and the yellow colored suspension thus formed was left without stirring for 1 h. Then, the suspension was filtered to give a yellow powder, which was solubilized in ethyl acetate, filtered, dried over anhydrous Na$_2$SO$_4$, and concentrated to dryness yielding the desired compound. Yield: 79%. Rf=0.46 (dichloromethane-methanol 9.5:0.5); mp: 106° C. $^1$H-NMR 400 MHz (DMSO-$d_6$): δ 9.64 (s, 1H), 9.28 (s, 1H), 7.39 (d, 1H), 7.10 (d, 1H), 3.98 (s, 3H), 3.94 (s, 3H). MS: m/z 190 [M]$^+$ Preparation of quinazoline-5,8-dione (QD323)

A solution of 5,8-dimethoxyquinazoline (4, 0.35 g, 1.84 mmol) in (7:3) acetonitrile:water (10 mL) was cooled at 0° C. in an ice bath and a solution of ceric ammonium nitrate (2.7 eq., 2.72 g, 4.97 mmol) in (9:1) acetonitrile:water (10 mL) was added dropwise. The reaction mixture was stirred for 20 minutes, then poured into ice/water and extracted with CH$_2$Cl$_2$. The organic layer was washed with water, dried over anhydrous Na$_2$SO$_4$ and concentrated to dryness to give a brown powder. Yield: 69%. Rf=0.62 (dichloromethane-methanol 9.5:0.5); mp: >320° C. $^1$H-NMR 400 MHz (DMSO-$d_6$): δ 9.69 (s, 1H), 9.43 (s, 1H), 7.28 (d, 1H), 7.18 (d, 1H). $^{13}$C-NMR 400 MHz (DMSO-$d_6$): δ 184.07, 182.88, 162.08, 156.27, 152.61, 139.46, 137.74, 124.61. MS: m/z 160 [M]$^+$ Preparation of Compounds QD324-327, 329, 331, 332, 334-336, 338, 353-357.

General Method A

A solution of quinazoline-5,8-dione, cerium (III) chloride eptahydrate (CeCl$_3$.7H$_2$O, 1.1 eq.) and (3,4,5)-substituted aniline (1.1 eq.) in absolute ethanol was stirred at room temperature for 1-2 h. Next, most of the ethanol was removed under vacuum, and water was added, followed by the extraction with CH$_2$Cl$_2$. The organic layers were washed with water and brine, dried over anhydrous Na$_2$SO$_4$ and concentrated to dryness. Then, the crude product was purified by flash chromatography to give the expected product.

6-((4-phenoxyphenyl)amino)quinazoline-5,8-dione (QD324)

Quinazoline-5,8-dione (QD323, 0.10 g, 0.62 mmol), cerium (III) chloride eptahydrate (CeCl$_3$.7H$_2$O, 1.1 eq., 0.26 g, 0.69 mmol), 4-phenoxyaniline (1.1 eq., 0.13 g, 0.69 mmol), and absolute ethanol (11 mL). Flash chromatography (ethyl acetate-petroleum ether 6:4) gave compound QD324 as a violet powder. Yield: 65%. Rf=0.30 (ethyl acetate-petroleum ether 6:4); mp: 169-171° C. $^1$H-NMR 400 MHz (CDCl$_3$): δ 9.66 (s, 1H), 9.49 (s, 1H), 7.51 (s, 1H), 7.39 (t, 2H), 7.25 (d, 2H), 7.20-7.15 (m, 1H), 7.09-7.04 (m, 4H), 6.53 (s, 1H). $^{13}$C-NMR 400 MHz (CDCl$_3$): δ 180.65, 180.39, 163.76, 156.48, 156.31, 154.40, 145.15, 130.90, 130.01, 125.25, 124.04, 123.34, 119.76, 119.28, 104.65. MS: m/z 343 [M]$^+$ 6-([1,1'-biphenyl]-4-ylamino)quinazoline-5,8-dione (QD325)

Quinazoline-5,8-dione (QD323, 0.16 g, 1.01 mmol), cerium (III) chloride eptahydrate (CeCl$_3$.7H$_2$O, 1.1 eq., 0.41 g, 1.11 mmol), 4-aminobiphenyl (1.1 eq., 0.19 g, 1.11 mmol), and absolute ethanol (19 mL). Flash chromatography (ethyl acetate-petroleum ether 7:3) gave compound QD325 as a violet powder. Yield: 58%. Rf=0.48 (ethyl acetate-petroleum ether 8:2); mp: 230° C. $^1$H-NMR 400 MHz (CDCl$_3$): δ 9.68 (s, 1H), 9.51 (s, 1H), 7.68 (d, 2H), 7.65 (s, 1H), 7.60 (d, 2H), 7.48 (t, 2H), 7.42-7.36 (m, 3H), 6.73 (s, 1H). $^{13}$C-NMR 400 MHz (CDCl$_3$): δ 180.67, 180.52, 163.78, 156.39, 154.32, 144.33, 139.71, 135.44, 128.99, 128.53, 127.53, 127.00, 123.26, 105.20. MS: m/z 327 [M]$^+$ 6-((3,4,5-trimethoxyphenyl)amino)quinazoline-5,8-dione (QD326)

Quinazoline-5,8-dione (QD323, 0.07 g, 0.44 mmol), cerium (III) chloride eptahydrate (CeCl$_3$.7H$_2$O, 1.1 eq., 0.18 g, 0.48 mmol), 3,4,5-trimethoxyaniline (1.1 eq., 0.09 g, 0.48 mmol), and absolute ethanol (8 mL). Flash chromatography (ethyl acetate-petroleum ether from 7:3 to 8:2) gave compound QD326 as a violet powder. Yield: 88%. Rf=0.18 (ethyl acetate-petroleum ether 8:2); mp: 161-162° C. $^1$H-NMR 400 MHz (CDCl$_3$): δ 9.67 (s, 1H), 9.49 (s, 1H), 7.51 (s, 1H), 6.59 (s, 1H), 6.50 (s, 2H), 3.88 (s, 9H). $^{13}$C-NMR 400 MHz (CDCl$_3$): δ 180.61, 180.40, 163.77, 156.33, 154.15, 144.90, 136.96, 131.87, 123.30, 105.00, 101.20, 61.07, 56.39. MS: m/z 341 [M]$^+$

6-((4-(trifluoromethoxy)phenyl)amino)quinazoline-5,8-dione (QD327)

Quinazoline-5,8-dione (QD323, 0.05 g, 0.31 mmol), cerium (III) chloride eptahydrate (CeCl$_3$.7H$_2$O, 1.1 eq., 0.13 g, 0.34 mmol), 4-(trifluoromethoxy)aniline (1.1 eq., 0.046 mL, 0.34 mmol), and absolute ethanol (6 mL). Flash chromatography (dichloromethane-methanol 9.7:0.3) gave compound QD327 as a dark red powder. Yield: 67%. Rf=0.53 (dichloromethane-methanol 9.5:0.5); mp: 114° C. $^1$H-NMR 400 MHz (CDCl$_3$): δ 9.68 (s, 1H), 9.51 (s, 1H), 7.55 (s, 1H), 7.33 (s, 4H), 6.58 (s, 1H). MS: m/z 335 [M]$^+$

6-((4-(hydroxymethyl)phenyl)amino)quinazoline-5,8-dione (QD329)

Quinazoline-5,8-dione (QD323, 0.05 g, 0.31 mmol), cerium (III) chloride eptahydrate (CeCl$_3$.7H$_2$O, 1.1 eq., 0.13 g, 0.34 mmol), 4-aminobenzyl alcohol (1.1 eq., 0.04 g, 0.34 mmol), and absolute ethanol (6 mL). Flash chromatography (dichloromethane-methanol 9.7:0.3) gave compound QD329 as a brown-red powder. Yield: 27%. Rf=0.30 (dichloromethane-methanol 9.5:0.5); mp: 203° C. $^1$H-NMR 400 MHz (CDCl$_3$): δ 9.67 (s, 1H), 9.50 (s, 1H), 7.59 (s, 1H), 7.47 (d, 2H), 7.29 (d, 2H), 6.64 (s, 1H), 4.75 (s, 2H). MS: m/z 303 [M+Na]$^+$

Methyl 4-((5,8-dioxo-5,8-dihydroquinazolin-6-yl)amino)benzoate (QD331)

Quinazoline-5,8-dione (QD323, 0.06 g, 0.37 mmol), cerium (III) chloride eptahydrate (CeCl$_3$.7H$_2$O, 1.1 eq., 0.15 g, 0.41 mmol), methyl 4-aminobenzoate (1.1 eq., 0.06 g, 0.41 mmol), and absolute ethanol (7.2 mL). Flash chromatography (ethyl acetate-petroleum ether from 6:4 to 7:3) gave compound QD331 as a red powder. Yield: 42%. Rf=0.35 (ethyl acetate-petroleum ether 7:3); mp: 226-230° C. $^1$H-NMR 400 MHz (CDCl$_3$): δ 9.69 (s, 1H), 9.52 (s, 1H), 8.14 (d, 2H), 7.72 (s, 1H), 7.36 (d, 2H), 6.81 (s, 1H), 3.95 (s, 3H). $^{13}$C-NMR 400 MHz (CDCl$_3$): δ 180.75, 180.40, 165.96, 163.85, 156.57, 153.96, 143.34, 140.64, 131.51, 127.69, 123.27, 121.66, 121.55, 106.35, 52.35. MS: m/z 309 [M]$^+$

Ethyl 4-((5,8-dioxo-5,8-dihydroquinazolin-6-yl)amino)benzoate (QD332)

Quinazoline-5,8-dione (QD323, 0.13 g, 0.81 mmol), cerium (III) chloride eptahydrate (CeCl$_3$.7H$_2$O, 1.1 eq., 0.33 g, 0.89 mmol), ethyl 4-aminobenzoate (1.1 eq., 0.15 g, 0.89 mmol), and absolute ethanol (16 mL). Flash chromatography (ethyl acetate-petroleum ether 6.5:3.5) gave compound QD332 as a red powder. Yield: 39%. Rf=0.36 (ethyl acetate-petroleum ether 7:3); mp: 206-207° C. $^1$H-NMR 400 MHz (CDCl$_3$): δ 9.69 (s, 1H), 9.52 (s, 1H), 8.14 (d, 2H), 7.72 (s, 1H), 7.36 (d, 2H), 6.80 (s, 1H), 4.43-4.38 (q, 2H), 1.42 (t, 3H). $^{13}$C-NMR 400 MHz (CDCl$_3$): δ 180.74, 180.42, 165.49, 163.85, 156.56, 153.98, 143.38, 140.53, 131.47, 128.08, 123.27, 121.65, 106.31, 61.31, 14.34. MS: m/z 323 [M]$^+$

6-((4'-fluoro-[1,1'-biphenyl]-4-yl)amino)quinazoline-5,8-dione (QD334)

Quinazoline-5,8-dione (QD323, 0.05 g, 0.31 mmol), cerium (III) chloride eptahydrate (CeCl$_3$.7H$_2$O, 1.1 eq., 0.13 g, 0.34 mmol), 4-amino-4'-fluorobiphenyl (1.1 eq., 0.06 g, 0.34 mmol), and absolute ethanol (6 mL). Flash chromatography (ethyl acetate-petroleum ether from 7:3 to 8:2) gave compound QD334 as a violet powder. Yield: 29%. Rf=0.32 (ethyl acetate-petroleum ether 7:3); mp: 285-289° C. $^1$H-NMR 400 MHz (CDCl$_3$): δ 9.68 (s, 1H), 9.51 (s, 1H), 7.63 (d, 2H), 7.55 (t, 2H), 7.53 (s, 1H), 7.37 (d, 2H), 7.16 (t, 2H), 6.72 (s, 1H). $^{13}$C-NMR 400 MHz (CDCl$_3$): δ 180.64, 180.53, 163.97, 163.79, 161.51, 156.39, 154.30, 144.33, 138.70, 135.98, 135.47, 128.65, 128.39, 123.33, 116.03, 115.82, 105.21. MS: m/z 345 [M]$^+$

6-((4'-ethyl-[1,1'-biphenyl]-4-yl)amino)quinazoline-5,8-dione (QD335)

Quinazoline-5,8-dione (QD323, 0.05 g, 0.34 mmol), cerium (III) chloride eptahydrate (CeCl$_3$.7H$_2$O, 1.1 eq., 0.14 g, 0.37 mmol), 4-amino-4'-ethylbiphenyl (1.1 eq., 0.07 g, 0.37 mmol), and absolute ethanol (6.5 mL). Flash chromatography (ethyl acetate-petroleum ether from 6:4 to 7:3) gave compound QD335 as a red-violet powder. Yield: 60%. Rf=0.36 (ethyl acetate-petroleum ether 7:3); mp: 232° C. $^1$H-NMR 400 MHz (CDCl$_3$): δ 9.66 (s, 1H), 9.49 (s, 1H), 7.68 (s, 1H), 7.66 (d, 2H), 7.51 (d, 2H), 7.34 (d, 2H), 7.30 (d, 2H), 6.71 (s, 1H), 2.74-2.68 (q, 2H), 1.29 (t, 3H). $^{13}$C-NMR 400 MHz (CDCl$_3$): δ 180.67, 180.48, 163.73, 156.35, 154.34, 144.35, 144.09, 139.64, 137.03, 135.15, 128.53, 128.46, 126.89, 123.35, 123.24, 105.11, 28.54, 15.55. MS: m/z 356 [M+1]$^+$

6-((4'-methoxy[1,1'-biphenyl]-4-yl)amino)quinazoline-5,8-dione (QD336)

Quinazoline-5,8-dione (QD323, 0.05 g, 0.34 mmol), cerium (III) chloride eptahydrate (CeCl$_3$.7H$_2$O, 1.1 eq., 0.14 g, 0.37 mmol), 4'-methoxy-biphenyl-4-ylamine (1.1 eq., 0.07 g, 0.37 mmol), and absolute ethanol (6.5 mL). Flash chromatography (ethyl acetate-petroleum ether from 7:3 to 10:0) gave compound QD336 as a dark violet powder. Yield: 69%. Rf=0.29 (ethyl acetate-petroleum ether 7:3); mp: 270-272° C. $^1$H-NMR 400 MHz (CDCl$_3$): δ 9.67 (s, 1H), 9.51 (s, 1H), 7.63 (d, 2H), 7.61 (s, 1H), 7.53 (d, 2H), 7.32 (d, 2H), 7.01 (d, 2H), 6.71 (s, 1H), 3.87 (s, 3H). $^{13}$C-NMR 400 MHz (CDCl$_3$): δ 180.67, 180.47, 163.77, 159.58, 156.36, 154.37, 144.38, 139.38, 134.81, 132.20, 128.05, 128.01, 123.29, 123.19, 114.44, 105.09, 55.40. MS: m/z 357 [M]$^+$

6-((2-fluoro-4'-methyl-[1,1'-biphenyl]-4-yl)amino)quinazoline-5,8-dione (QD338)

Quinazoline-5,8-dione (QD323, 0.06 g, 0.35 mmol), cerium (III) chloride eptahydrate (CeCl$_3$.7H$_2$O, 1.1 eq., 0.14 g, 0.38 mmol), 2-fluoro-4'-methyl-biphenyl-4-ylamine (1.1 eq., 0.08 g, 0.38 mmol), and absolute ethanol (6.7 mL). Flash chromatography (ethyl acetate-petroleum ether, from 6:4 to 8:2) gave compound QD338 as a violet powder. Yield: 60%. Rf=0.26 (ethyl acetate-petroleum ether 7:3); mp: 282-283° C. $^1$H-NMR 400 MHz (CDCl$_3$): δ 9.69 (s, 1H), 9.52 (s, 1H), 7.62 (s, 1H), 7.52 (t, 1H), 7.45 (d, 2H), 7.29 (d, 2H), 7.14 (t, 2H), 6.75 (s, 1H), 2.42 (s, 3H). $^{13}$C-NMR 400 MHz (CDCl$_3$): δ 180.61, 180.47, 163.83, 156.49, 143.93, 138.14, 131.79, 129.40, 128.89, 128.71, 123.31, 118.67, 110.85, 110.58, 105.75, 21.24. MS: m/z 359 [M]$^+$

6-((3-methoxyphenyl)amino)quinazoline-5,8-dione (QD353)

Quinazoline-5,8-dione (QD323, 0.05 g, 0.31 mmol), cerium (III) chloride eptahydrate (CeCl$_3$.7H$_2$O, 1.1 eq., 0.13 g, 0.34 mmol), m-anisidine (1.1 eq., 0.38 mL, 0.34 mmol), and absolute ethanol (6 mL). Flash chromatography (ethyl acetate-petroleum ether 6:4) gave compound QD353 as a dark violet powder. Yield: 43%. Rf=0.30 (ethyl acetate-petroleum ether 7:3); mp: 142° C. $^1$H-NMR 400 MHz (CDCl$_3$): δ 9.67 (s, 1H), 9.50 (s, 1H), 7.56 (s, 1H), 7.36 (t, 1H), 6.88 (d, 2H), 6.83 (d, 2H), 6.82 (s, 1H), 6.69 (s, 1H), 3.84 (s, 3H). $^{13}$C-NMR 400 MHz (CDCl$_3$): δ 180.65, 180.56, 163.76, 160.81, 156.36, 154.28, 144.45, 137.40, 130.75, 123.33, 115.25, 112.07, 109.17, 105.34, 55.53. MS: m/z 281 [M]$^+$

6-((4-methoxyphenyl)amino)quinazoline-5,8-dione (QD354)

Quinazoline-5,8-dione (QD323, 0.06 g, 0.37 mmol), cerium (III) chloride eptahydrate (CeCl$_3$.7H$_2$O, 1.1 eq., 0.15 g, 0.41 mmol), p-anisidine (1.1 eq., 0.05 g, 0.41 mmol), and absolute ethanol (7.2 mL). Flash chromatography (ethyl acetate-petroleum ether from 6.5:3.5 to 8:2) gave compound QD354 as a dark powder. Yield: 41%. Rf=0.32 (ethyl acetate-petroleum ether 7:3); mp: 238° C. $^1$H-NMR 400 MHz (CDCl$_3$): δ 9.66 (s, 1H), 9.48 (s, 1H), 7.49 (s, 1H), 7.21 (d, 2H), 6.98 (d, 2H), 6.48 (s, 1H), 3.85 (s, 3H). $^{13}$C-NMR 400 MHz (CDCl$_3$): δ 180.76, 180.28, 163.73, 156.24, 154.52, 145.34, 128.75, 125.18, 123.36, 115.16, 104.34, 55.62. MS: m/z 281 [M]$^+$

6-((3,4-dimethoxyphenyl)amino)quinazoline-5,8-dione (QD355)

Quinazoline-5,8-dione (QD323, 0.06 g, 0.40 mmol), cerium (III) chloride eptahydrate (CeCl$_3$.7H$_2$O, 1.1 eq., 0.16 g, 0.44 mmol), 3,4-dimethoxyaniline (1.1 eq., 0.067 g, 0.44 mmol), and absolute ethanol (7.6 mL). Flash chromatography (ethyl acetate-petroleum ether from 7:3 to 10:0) gave compound QD355 as a dark powder. Yield: 70%. Rf=0.23 (ethyl acetate-petroleum ether 8:2); mp: 241-242° C. $^1$H-NMR 400 MHz (CDCl$_3$): δ 9.66 (s, 1H), 9.49 (s, 1H), 7.50 (s, 1H), 6.92 (d, 2H), 6.86 (d, 2H), 6.78 (s, 1H), 6.53 (s, 1H), 3.92 (s, 3H), 3.90 (s, 3H). $^{13}$C-NMR 400 MHz (CDCl$_3$): δ 180.73, 180.31, 163.75, 156.75, 156.26, 154.48, 149.97, 148.10, 145.21, 129.02, 123.34, 116.10, 111.74, 107.50, 104.54, 56.18. MS: m/z 333 [M+1]$^+$

6-((4-fluorobenzyl)amino)quinazoline-5,8-dione (QD356)

Quinazoline-5,8-dione (QD323, 0.06 g, 0.40 mmol), cerium (III) chloride eptahydrate (CeCl$_3$.7H$_2$O, 1.1 eq., 0.16 g, 0.44 mmol), 4-fluorobenzylamine (1.1 eq., 0.05 mL, 0.44 mmol), and absolute ethanol (7.6 mL). Flash chromatography (ethyl acetate-petroleum ether from 7:3 to 8:2) gave compound QD356 as an orange powder. Yield: 35%. Rf=0.30 (ethyl acetate-petroleum ether 8:2); mp: 203° C. $^1$H-NMR 400 MHz (CDCl$_3$): δ 9.64 (s, 1H), 9.43 (s, 1H), 7.30 (t, 2H), 7.09 (t, 2H), 6.28 (s, 1H), 6.05 (s, 1H), 4.40 (d, 2H). $^{13}$C-NMR 400 MHz (CDCl$_3$): δ 180.33, 179.62, 163.93, 163.67, 161.47, 156.16, 154.57, 146.96, 130.68, 129.43, 123.35, 116.14, 103.76, 46.30. MS: m/z 283 [M]$^+$

6-((3,5-dimethoxyphenyl)amino)quinazoline-5,8-dione (QD357)

Quinazoline-5,8-dione (QD323, 0.06 g, 0.40 mmol), cerium (III) chloride eptahydrate (CeCl$_3$.7H$_2$O, 1.1 eq., 0.16 g, 0.44 mmol), 3,5-dimethoxyaniline (1.0 eq., 0.07 g, 0.44 mmol), and absolute ethanol (7.6 mL). Flash chromatography (ethyl acetate-petroleum ether from 6:4 to 7:3) gave compound QD357 as a violet powder. Yield: 70%. Rf=0.45 (ethyl acetate-petroleum ether 8:2); mp: 204-206° C. $^1$H-NMR 400 MHz (DMSO-d$_6$): δ 9.66 (s, 1H), 9.43 (s, 1H), 7.05 (s, 1H), 5.97 (s, 2H), 5.72 (s, 2H), 3.62 (s, 6H). $^{13}$C-NMR 400 MHz (CDCl$_3$): δ 183.14, 182.27, 162.43, 159.30, 157.54, 152.64, 150.43, 145.40, 138.54, 125.32, 100.99, 91.24, 55.74. MS: m/z 281 [M]$^+$ Preparation of the Compounds QD328, 330, 333, 337. General Method B A solution of quinazoline-5,8-dione, cerium (III) chloride eptahydrate (CeCl$_3$.7H$_2$O, 1.1 eq.) and (3,4,5)-substituted aniline (1.1 eq.) in absolute ethanol was stirred at room temperature for 2-6 h. Next, most of the ethanol was removed under vacuum, and water was added, followed by the extraction with CH$_2$Cl$_2$. The organic layers were dried over sodium sulfate (Na$_2$SO$_4$) and concentrated to dryness. Then, the crude residue was treated with water, and the solid residue that precipitated was filtered and tritured with petroleum ether to give the desired product.

4-((5,8-dioxo-5,8-dihydroquinazolin-6-yl)amino) benzenesulfonamide (QD328)

Quinazoline-5,8-dione (QD323, 0.05 g, 0.31 mmol), cerium (III) chloride eptahydrate (CeCl$_3$.7H$_2$O, 1.1 eq., 0.13 g, 0.34 mmol), sulfanilamide (1.1 eq., 0.06 g, 0.34 mmol), and absolute ethanol (6 mL). The precipitate was filtered and tritured with petroleum ether gave compound QD328 as a red powder. Yield: 59%. Rf=0.16 (ethyl acetate-petroleum ether 8:2); mp: >320° C. $^1$H-NMR 400 MHz (DMSO-d$_6$): δ 9.72 (s, 1H), 9.64 (s, 1H), 9.44 (s, 1H), 7.88 (d, 2H), 7.60 (d, 2H), 7.38 (s, 2H), 6.46 (s, 1H). $^{13}$C-NMR 400 MHz (DMSO-d$_6$): δ 180.50, 180.32, 162.58, 155.78, 153.46, 145.33, 140.91, 140.20, 127.38, 127.05, 124.19, 123.17, 112.38, 105.11. MS: m/z 331 [M+1]$^+$

4-((5,8-dioxo-5,8-dihydroquinazolin-6-yl)amino) benzamide (QD330)

Quinazoline-5,8-dione (QD323, 0.05 g, 0.31 mmol), cerium (III) chloride eptahydrate (CeCl$_3$.7H$_2$O, 1.1 eq., 0.13 g, 0.34 mmol), 4-aminobenzamide (1.1 eq., 0.05 g, 0.34 mmol), and absolute ethanol (6 mL). The precipitate was filtered and tritured with petroleum ether gave compound QD330 as a brown powder. Yield: 24%. Rf=0.58 (dichloromethane-methanol 9.5:0.5); mp: >320° C. $^1$H-NMR 400 MHz (DMSO-d$_6$): δ 9.65 (s, 1H), 9.63 (s, 1H), 9.43 (s, 1H), 7.95 (d, 2H), 7.49 (d, 2H), 7.38 (s, 2H), 6.42 (s, 1H). MS: m/z 295 [M+1]$^+$

(3-((5,8-dioxo-5,8-dihydroquinazolin-6-yl)amino) phenyl)boronic acid (QD333)

Quinazoline-5,8-dione (QD323, 0.05 g, 0.31 mmol), cerium (III) chloride eptahydrate (CeCl$_3$.7H$_2$O, 1.1 eq., 0.13 g, 0.34 mmol), 3-aminophenylboronic acid (1.1 eq., 0.05 g, 0.34 mmol), and absolute ethanol (6 mL). The precipitate was filtered and tritured with petroleum ether gave compound QD333 as a red powder. Yield: 48%. Rf=0.37 (dichloromethane-methanol 9.5:0.5); mp: 208-210° C. $^1$H-NMR 400 MHz (DMSO-d$_6$): δ 9.61 (s, 1H), 9.52 (s, 1H), 9.41 (s, 1H), 8.20 (s, 2H), 7.77-7.70 (m, 2H), 7.43 (m, 2H), 6.23 (s, 1H). MS: m/z 318 [M+Na]$^+$

6-((4'-amino-[1,1'-biphenyl]-4-yl)amino)quinazoline-5,8-dione (QD337)

Quinazoline-5,8-dione (QD323, 0.05 g, 0.34 mmol), cerium (III) chloride eptahydrate (CeCl$_3$.7H$_2$O, 1.1 eq., 0.14 g, 0.37 mmol), benzidine (1.1 eq., 0.07 g, 0.37 mmol), and absolute ethanol (6.5 mL). The precipitate was filtered and tritured with petroleum ether gave compound QD337 as a dark violet powder. Yield: 16%. Rf=0.71 (dichlorometane-methanol 9.5:0.5); mp: >320° C. $^1$H-NMR 400 MHz (DMSO-d$_6$): δ 9.66 (s, 1H), 9.63 (s, 1H), 9.44 (s, 1H), 7.83 (d, 2H), 7.64 (d, 1H), 7.53 (d, 2H), 7.40 (d, 2H), 6.65 (d, 1H), 6.40 (s, 1H), 5.27 (s, 2H). MS: m/z 342 [M]$^+$

Preparation of (3-aminopropyl)triphenylphosphonium bromide hydrobromide (6)

To a 50 mL round-bottom flask equipped with a magnetic stir bar, triphenylphosphine (1.0 eq., 1.0 g, 3.82 mmol), 3-bromopropylamine hydrobromide (5, 1.0 eq., 0.84 g, 3.82 mmol), and acetonitrile (7 mL), were added. The resulting suspension was heated to reflux and the mixture was stirred for 16 h. The reaction was cooled to room temperature, then n-hexane was added and the resulting solid was filtered, washed with n-hexane, dissolved in 100 mL isopropanol and precipitated with cold diethyl ether, to give a white powder. Yield: 50%; Rf=0.28 (dichlorometane-methanol 9:1); mp: 200° C. $^1$H-NMR 400 MHz (CDCl$_3$): δ 7.95-7.92 (m, 3H), 7.84-7.74 (m, 15H), 3.74 (m, 2H), 3.00-2.98 (m, 2H), 1.85 (m, 2H).

Preparation of (3-(4-aminobenzamido)propyl) triphenylphosphonium bromide (QD339)

To a solution of 4-aminobenzoic acid (1.0 eq., 0.076 g, 0.55 mmol) in CH$_2$Cl$_2$ (12 mL), N,N-diisopropylethylamine (DIPEA, 5 eq. 0.48 mL, 2.75 mmol), and HBtU (1.0 eq., 0.206 g, 0.55 mmol) were added. The reaction mixture was stirred for 15 minutes, and (3-aminopropyl)triphenylphosphonium bromide (6, 3 eq. 0.80 g, 1.66 mmol) and DMAP (0.04 eq., 2.7 g, 0.02 mmol) were added. The resulting mixture was stirred at room temperature for 5 h, filtered, washed with CH$_2$Cl$_2$, and concentrated to dryness. The crude product was purified by flash chromatography on silica gel using dichloromethane-isopropanol (9.5:0.5) to give a beige powder. Yield: 70%; Rf=0.27 (dichlorometane-methanol 9:1); mp: 203-205° C. $^1$H-NMR 400 MHz (CDCl$_3$): δ 8.91 (t, 1H), 8.10 (d, 2H), 7.77-7.72 (m, 9H), 7.61-7.58 (m, 6H), 6.70 (d, 2H), 3.94-3.90 (m, 2H), 3.72-3.71 (m, 2H), 1.95 (m, 2H).

Preparation of (3-(4-((5,8-dioxo-5,8-dihydroquinazolin-6-yl)amino)benzamido)propyl) triphenylphosphonium bromide (QD340)

A solution of quinazoline-5,8-dione (5, 1.0 eq., 0.04 g, 0.25 mmol), cerium (III) chloride eptahydrate (CeCl$_3$.7H$_2$O, 1.1 eq., 0.102 g, 0.27 mmol) and (3-(4-aminobenzamido)propyl)triphenyl phosphonium bromide (1.1 eq., 0.143 g, 0.27 mmol) in absolute ethanol (5 mL) was stirred at room temperature for 2 h. Then, most of the ethanol was removed under vacuum, and water was added, followed by the extraction with CH$_2$Cl$_2$. The organic layers were washed with water, brine, dried over anhydrous sodium sulphate and concentrated to dryness. The crude product was tritured with petroleum ether to give a red powder. Yield: 42%; Rf=0.45 (dichlorometane-methanol 9:1); mp: 205° C. $^1$H-NMR 400 MHz (CDCl$_3$): δ 9.90 (t, 1H), 9.67 (s, 1H), 9.50 (s, 1H), 8.46 (d, 2H), 7.79-7.72 (m, 10H), 7.65-7.62 (m, 6H), 7.37 (d, 2H), 6.74 (s, 1H), 3.97-3.93 (m, 2H), 3.75-3.74 (m, 2H), 2.00 (m, 2H). MS: m/z 342 [M−1]$^+$

Preparation of (3-(3-aminobenzamido)propyl)triphenylphosphonium bromide (QD358)

To a solution of 3-aminobenzoic acid (1.0 eq., 0.076 g, 0.55 mmol) in CH$_2$Cl$_2$ (12 mL), N,N-diisopropylethylamine (DIPEA, 5 eq. 0.48 mL, 2.75 mmol), and HBtU (1.0 eq., 0.206 g, 0.55 mmol) were added. The reaction mixture was stirred for 15 minutes before (3-aminopropyl)triphenylphosphonium bromide (6, 3 eq., 0.80 g, 1.66 mmol) and DMAP (0.04 eq., 2.7 μg, 0.02 mmol) were added. The resulting mixture was stirred at room temperature for 5 h, filtered, washed with CH$_2$Cl$_2$, and concentrated to dryness. The crude product was purified by flash chromatography on silica gel using dichloromethane-isopropanol (9.5:0.5) to give an orange powder. Yield: 59%; Rf=0.45 (dichlorometane-methanol 9:1); mp: 223° C. $^1$H-NMR 400 MHz (CDCl$_3$): δ 8.97 (t, 1H), 7.77-7.73 (m, 10H), 7.62-7.60 (m, 6H), 7.55 (d, 1H), 7.21 (t, 1H), 6.78 (d, 1H), 3.92-3.88 (m, 2H), 3.73-3.72 (m, 2H), 1.97 (m, 2H).

Preparation of (3-(3-((5,8-dioxo-5,8-dihydroquinazolin-6-yl)amino)benzamido)propyl) triphenylphosphonium bromide (QD359)

A solution of quinazoline-5,8-dione (1.0 eq., 0.04 g, 0.25 mmol), cerium (III) chloride eptahydrate (CeCl$_3$.7H$_2$O, 1.1 eq., 0.102 g, 0.27 mmol) and (3-(3-aminobenzamido)propyl) triphenyl phosphonium bromide (1.0 eq., 0.130 g, 0.25 mmol) in absolute ethanol (5 mL) was stirred at room temperature for 1.5 h. Then, most of the ethanol was removed under vacuum, and water was added, followed by the extraction with CH$_2$Cl$_2$. The organic layers were washed with water, dried over anhydrous sodium sulphate and concentrated to dryness. The crude product was purified by flash chromatography on silica gel using dichloromethane-methanol (9.4:0.4) to give a red powder. Yield: 30%; Rf=0.21 (dichlorometane-methanol 9:1); mp: 108-110° C. $^1$H-NMR 400 MHz (CDCl$_3$): δ 9.78 (t, 1H), 9.64 (s, 1H), 9.47 (s, 1H), 8.34 (d, 2H), 8.19 (d, 2H), 7.77-7.73 (m, 10H), 7.64-7.62 (m, 6H), 7.54 (t, 1H), 7.45 (d, 1H), 6.63 (s, 1H), 3.92-3.88 (m, 2H), 3.74-3.73 (m, 2H), 2.05-2.00 (m, 2H). MS: m/z 342 [M−1]$^+$.

Scheme 6$^a$
Preparation of QD385-389

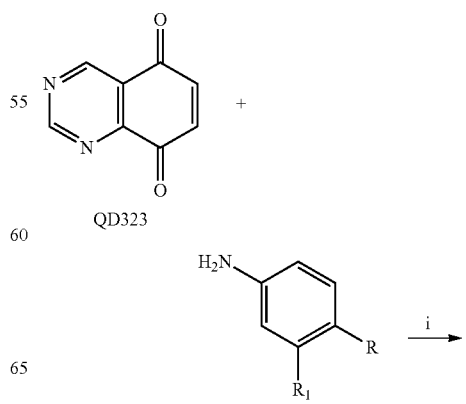

-continued

QD385-QD389

|  | R | $R_1$ |
|---|---|---|
| QD385 | H | 3-Ph |
| OD386 | 4-Cl-Ph | H |
| QD387 | 3,5-Cl-Ph | H |
| QD388 | N-piperidine | H |
| QD389 | N-morpholine | F |

[a]Reagents and conditions: (i) CeCl$_3$•7H$_2$O, abs EtOH, rt, 1.5 hrs

Scheme 7[a] Preparation of QD390, 391

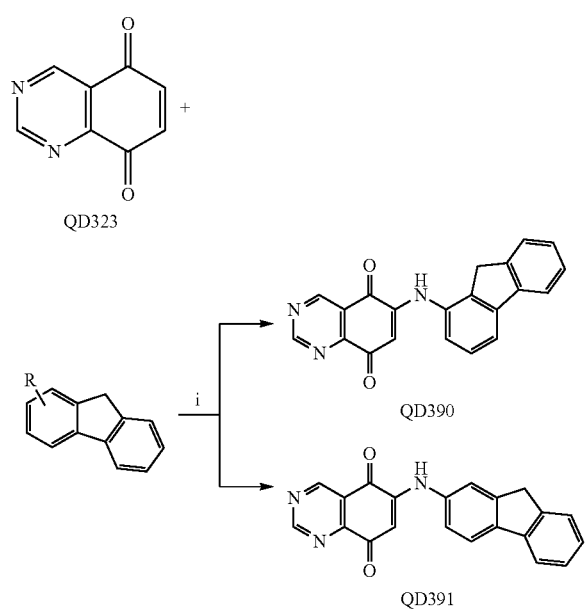

[a]Reagents and conditions: (i) CeCl$_3$•7H$_2$O, abs EtOH, rt, 1.5 hrs

Scheme 8[a]
Preparation of QD392-395

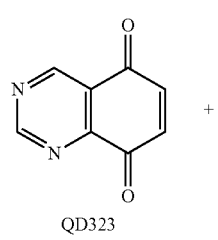 [SMILES: O=C1C=CC(=O)c2ncncc21 ; "QD323"]

-continued

QD392-QD395

|  | R |
|---|---|
| QD392 | 4-Et-Ph |
| QD393 | 4-Cy |
| QD394 | 4-Me-Piperazine |
| QD395 | 2-N-piperidine |

[a]Reagents and conditions: (i) CeCl$_3$•7H$_2$O, abs EtOH, rt, 1.5 hrs

Scheme 9[a]
General method for the preparation of QD396-424

QD396-QD424

|  | R |
|---|---|
| QD396 | 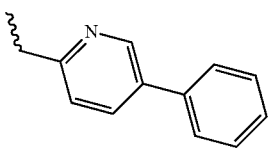 |
| QD397 | 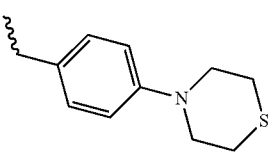 |
| QD398 | |

Scheme 9ᵃ
General method for the preparation of QD396-424
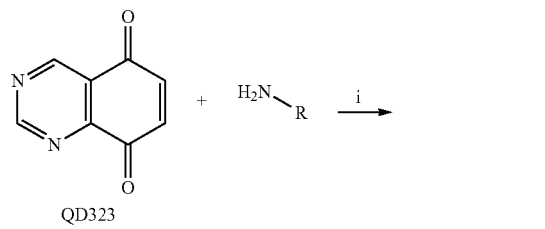
QD323
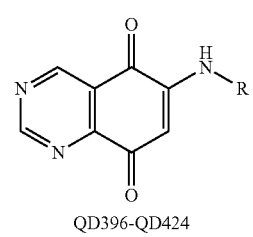
QD396-QD424
| | R |
|---|---|
| QD399 | 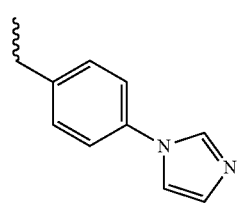 |
| QD400 | 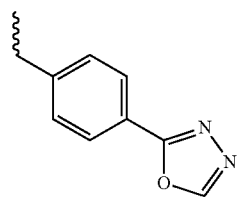 |
| QD401 | 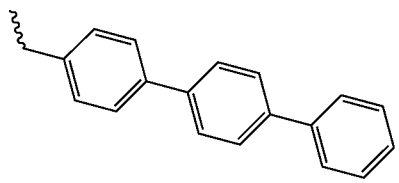 |
| QD402 | 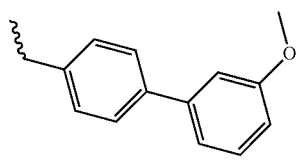 |
| QD403 | 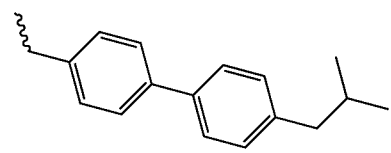 |
Scheme 9ᵃ
General method for the preparation of QD396-424
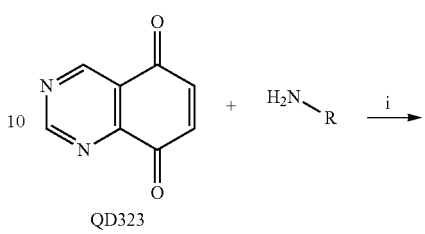
QD323
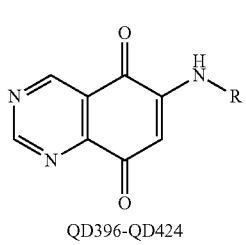
QD396-QD424
| | R |
|---|---|
| QD404 | 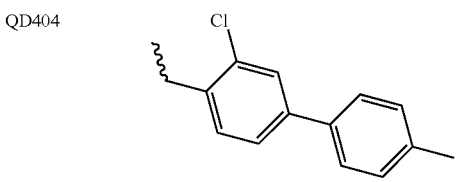 |
| QD405 | 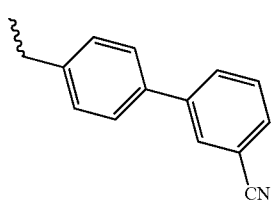 |
| QD406 | 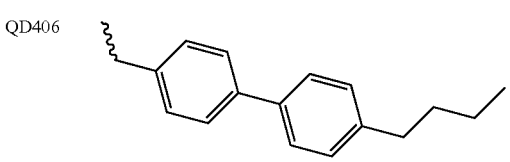 |
| QD407 | 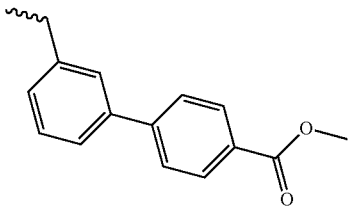 |
| QD408 | 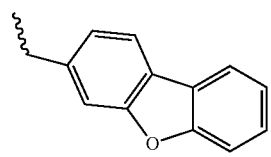 |

-continued
Scheme 9ᵃ
General method for the preparation of QD396-424
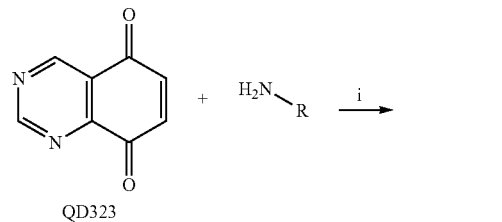
QD323
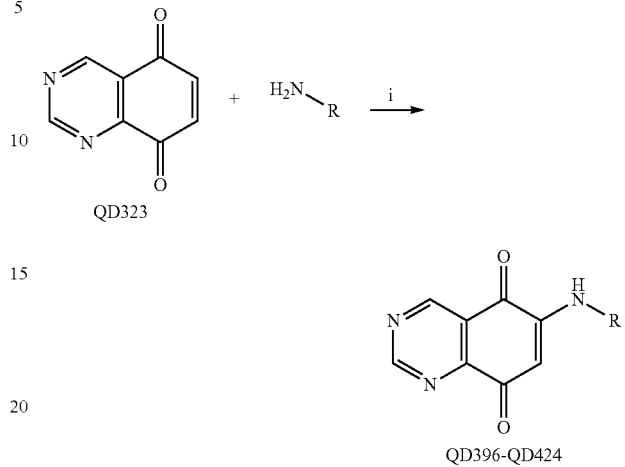
QD323
QD396-QD424
QD396-QD424
| | R | | R |
|---|---|---|---|
| QD409 | 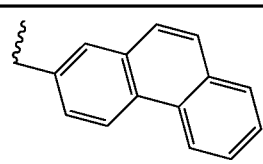 | QD415 | 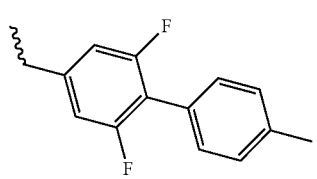 |
| QD410 | 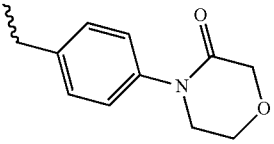 | QD416 | 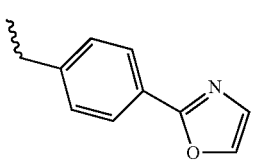 |
| QD411 | 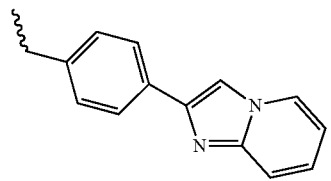 | QD417 | 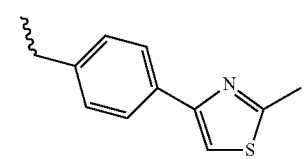 |
| QD412 | 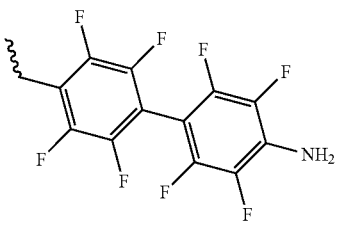 | QD418 | 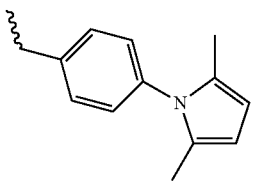 |
| QD413 | 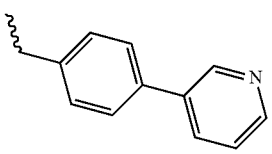 | QD419 | 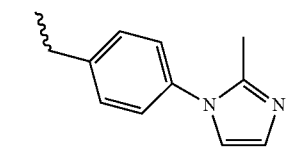 |
| QD414 | 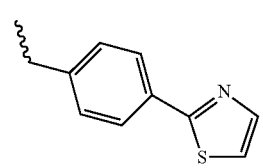 | QD420 | 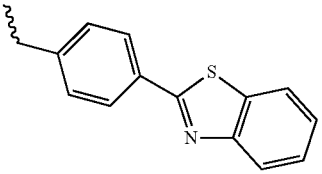 |

Scheme 9[a]
General method for the preparation of QD396-424

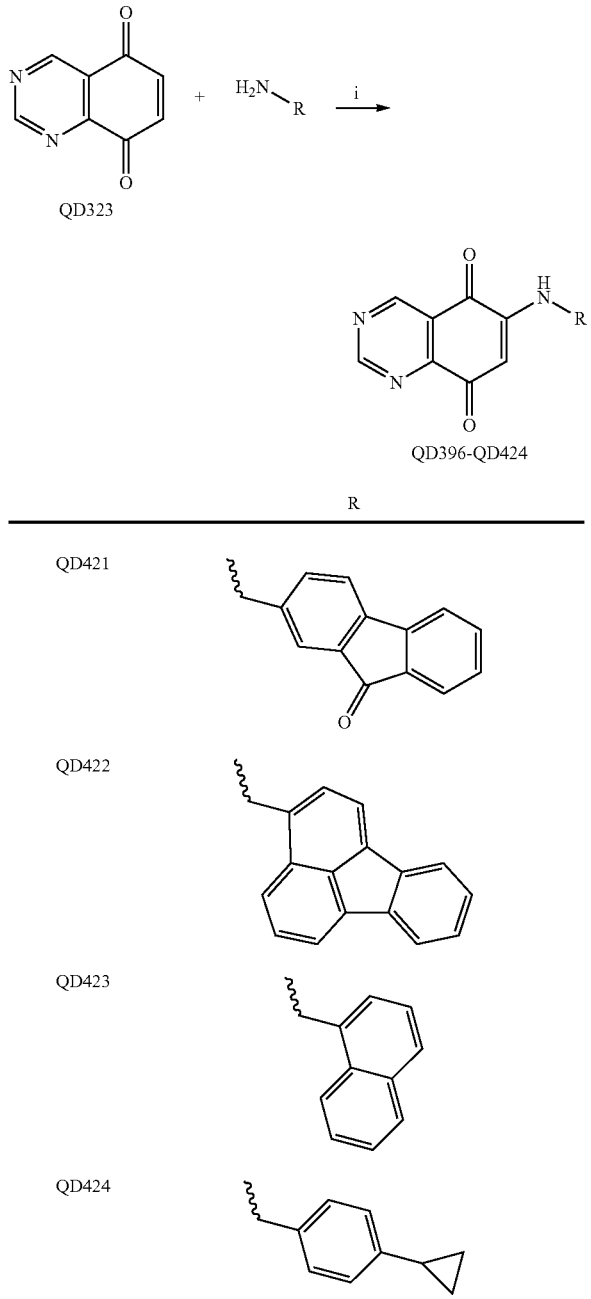

QD323 + H₂N-R →(i)→ QD396-QD424

| | R |
|---|---|
| QD421 | (fluorenone group) |
| QD422 | (fluoranthene group) |
| QD423 | (naphthalene group) |
| QD424 | (4-cyclopropylphenyl group) |

[a]Reagents and conditions: (i) CeCl₃·7H₂O, abs EtOH, rt, 1-3 hrs

Preparation of the Compounds QD385, 386, 387, 388, 389, 390, 391, 392, 393, 394, 395
General Method C A solution of quinazoline-5,8-dione, cerium (III) chloride eptahydrate (CeCl$_3$.7H$_2$O, 1.1 eq.) and substituted aniline (1.0 eq.) in absolute ethanol was stirred at room temperature for 1.5 h. Next, after removing most of the ethanol under vacuum, the crude residue was diluted, extracted with CH$_2$Cl$_2$ and washed with water. The organic layers were dried over sodium sulfate (Na$_2$SO$_4$) and concentrated to dryness. Then, the crude residue was purified by flash chromatography to give the desired product.

General Method for the Preparation of the Compounds QD396, 397, 398, 399, 400, 401, 402, 403, 404, 405, 406, 407, 408, 409, 410, 411, 412, 413, 414, 415, 416, 417, 418, 419, 420, 421, 422, 423, 424

A solution of quinazoline-5,8-dione, cerium (III) chloride eptahydrate (CeCl$_3$.7H$_2$O, 1.1 eq.) and substituted aniline (1.0 eq.) in absolute ethanol was stirred at room temperature for 1.5 h. Next, after removing most of the ethanol under vacuum, the crude residue was diluted with water, extracted with CH$_2$Cl$_2$, and washed with water. The organic layers were dried over sodium sulfate (Na$_2$SO$_4$), concentrated to dryness, and the solid that precipitated was triturated with ether petroleum. Then, the solid residue was filtered and purified by flash chromatography to give the desired product.

6-(Biphenyl-3-ylamino)quinazoline-5,8-dione [QD 385]

Quinazoline-5,8-dione (QD323, 0.050 g, 0.312 mmol), cerium (III) chloride eptahydrate (CeCl$_3$.7H$_2$O, 1.1 eq., 0.128 g, 0.343 mmol), 3-aminobiphenyl (1.0 eq., 0.053 g, 0.312 mmol), and absolute ethanol (6 mL). Flash chromatography (dichloromethane-methanol=9.8:0.2) gave compound QD385 as a violet powder. Yield %: 20. Rf: 0.41 (ether petroleum:ethyl acetate=3:7). mp: 199-200° C. $^1$H-NMR 400 MHz $^1$H-NMR (DMSO-d$_6$): δ 9.63 (s, 1H), 9.43 (s, 1H), 7.69-7.67 (m, 3H), 7.61-7.59 (d, 2H), 7.49-7.46 (t, 2H), 7.41-7.36 (t, 3H), 6.34 (s, 1H). $^{13}$C-NMR (DMSO-d$_6$): δ 163.78, 130.33, 129.03, 127.15, 125.61, 121.74, 105.15. MS: m/z 327 (M$^+$).

6-(4'-Chlorobiphenyl-4-ylamino)quinazoline-5,8-dione [QD 386]

Quinazoline-5,8-dione (QD323, 0.050 g, 0.312 mmol), cerium (III) chloride eptahydrate (CeCl$_3$.7H$_2$O, 1.1 eq., 0.128 g, 0.343 mmol), 4-amino-4'-chlorobiphenyl (1.0 eq., 0.064 g, 0.312 mmol), and absolute ethanol (6 mL). Flash chromatography (ethyl acetate-petroleum ether=5:5) gave compound QD386 as a violet powder. Yield %: 95. Rf: 0.20 (ethyl acetate-petroleum ether=7:3). mp: 292-293° C. $^1$H-NMR (DMSO-d$_6$): δ 9.62 (s, 2H), 9.42 (s, 1H), 7.79-7.77 (d, 2H), 7.76-7.74 (d, 2H), 7.55-7.53 (d, 2H), 7.50-7.48 (d, 2H), 6.35 (s, 1H). $^{13}$C-NMR (DMSO-d$_6$): δ 180.52, 180.03, 162.59, 155.67, 153.74, 145.89, 138.07, 137.42, 135.77, 132.34, 128.91, 128.26, 127.53, 124.06, 104.06. MS: m/z 361 (M$^+$).

6-(3',5'-Dichlorobiphenyl-4-ylamino)quinazoline-5,8-dione [QD 387]

Quinazoline-5,8-dione (QD323, 0.050 g, 0.312 mmol), cerium (III) chloride eptahydrate (CeCl$_3$.7H$_2$O, 1.1 eq., 0.128 g, 0.343 mmol), 4-amino-3',5'-dichlorobiphenyl (1.0 eq., 0.074 g, 0.312 mmol), and absolute ethanol (6 mL). Flash chromatography (ethyl acetate-petroleum ether=5:5) gave compound QD387 as a violet powder. Yield %: 95. Rf: 0.50 (ethyl acetate-petroleum ether=7:3). mp: 260-261° C. $^1$H-NMR (DMSO-d$_6$): δ 9.63 (s, 2H), 9.43 (s, 1H), 7.87-7.85 (d, 2H), 7.79 (s, 2H), 7.61 (s, 1H), 7.52-7.50 (d, 2H), 6.38 (s, 1H). $^{13}$C-NMR (DMSO-d$_6$): δ 180.47, 180.15, 162.60, 155.70, 153.68, 145.75, 142.80, 138.28, 134.68, 133.99, 128.02, 125.20, 123.91, 104.34. MS: m/z 395 (M$^+$).

6-(4-(Piperidin-1-yl)phenylamino)quinazoline-5,8-dione [QD 388]

Quinazoline-5,8-dione (QD323, 0.050 g, 0.312 mmol), cerium (III) chloride eptahydrate (CeCl$_3$.7H$_2$O, 1.1 eq., 0.128 g, 0.343 mmol), 4-(1-piperidinyl)aniline (1.0 eq., 0.055 g, 0.312 mmol), and absolute ethanol (6 mL). Flash chromatography (ethyl acetate-petroleum ether=7:3) gave compound QD388 as a violet powder. Yield %: 66. Rf: 0.29 (ethyl acetate-petroleum ether=7:3). mp: 209° C. $^1$H-NMR (DMSO-d$_6$): δ 9.60 (s, 1H), 9.38 (s, 1H), 7.45 (s, 1H), 7.22-7.20 (d, 2H), 7.02-7.00 (d, 2H), 6.13 (s, 1H), 3.16 (s, 4H), 1.63-1.56 (d, 6H). $^{13}$C-NMR (DMSO-d$_6$): δ 180.65, 179.30, 162.59, 155.51, 154.08, 149.52, 146.47, 127.71, 124.93, 124.12, 115.91, 102.59, 49.23, 25.09, 23.83. MS: m/z 334 (M$^+$).

6-(4-Morpholinophenylamino)quinazoline-5,8-dione [QD 389]

Quinazoline-5,8-dione (QD323, 0.050 g, 0.312 mmol), cerium (III) chloride eptahydrate (CeCl$_3$.7H$_2$O, 1.1 eq., 0.128 g, 0.343 mmol), 4-(4-morpholinyl)aniline (1.0 eq., 0.056 g, 0.312 mmol), and absolute ethanol (6 mL). Flash chromatography (ethyl acetate-petroleum ether=7:3) gave compound QD389 as a violet powder. Yield %: 88. Rf: 0.10 (ethyl acetate-petroleum ether=7:3). mp: 226-227° C. $^1$H-NMR (DMSO-d$_6$): δ 9.60 (s, 1H), 9.47 (s, 1H, H—N), 9.39 (s, 1H), 7.26-7.24 (d, 2H), 7.05-7.03 (d, 2H), 6.14 (s, 1H), 3.76 (s, 4H), 3.15 (s, 4H). $^{13}$C-NMR (DMSO-d$_6$): δ 180.62, 179.41, 162.59, 155.53, 149.03, 146.49, 128.56, 124.97, 115.40, 102.70, 66.00, 48.18. MS: m/z 336 (M$^+$).

6-(9H-Fluoren-4-ylamino)quinazoline-5,8-dione [QD390]

Quinazoline-5,8-dione (QD323, 0.050 g, 0.312 mmol), cerium (III) chloride eptahydrate (CeCl$_3$.7H$_2$O, 1.1 eq., 0.128 g, 0.343 mmol), 1-aminofluorene (1.0 eq., 0.057 g, 0.312 mmol), and absolute ethanol (6 mL). Flash-chromatography (ethyl acetate-petroleum ether=7:3) gave compound QD390 as a violet powder. Yield %: 69. Rf: 0.46 (ethyl acetate-petroleum ether=7:3). mp: 217° C. $^1$H-NMR (CDCl$_3$): δ 9.68 (s, 1H), 9.53 (s, 1H), 7.57-7.55 (d, 2H), 7.52-7.49 (t, 1H), 7.45-7.41 (t, 1H), 7.38-7.35 (t, 1H), 7.31-7.29 (d, 1H), 6.43 (s, 1H), 3.86 (s, 2H). $^{13}$C-NMR (CDCl$_3$): δ 163.78, 156.33, 128.79, 127.74, 127.25, 125.18, 121.70, 120.42, 119.04, 105.53. MS: m/z 339 (M$^+$).

6-(9H-Fluoren-2-ylamino)quinazoline-5,8-dione [QD 391]

Quinazoline-5,8-dione (QD323, 0.050 g, 0.312 mmol), cerium (III) chloride eptahydrate (CeCl$_3$.7H$_2$O, 1.1 eq., 0.128 g, 0.343 mmol), 2-aminofluorene (1.0 eq., 0.057 g, 0.312 mmol), and absolute ethanol (6 mL). Flash chromatography (ethyl acetate-petroleum ether=5:5) gave compound QD391 as a violet powder. Yield %: 92. Rf: 0.14 (ethyl acetate-petroleum ether=7:3). mp: 236-237° C. $^1$H-NMR (DMSO-d$_6$): δ 9.62 (s, 2H), 9.43 (s, 1H), 8.00-7.97 (d, 1H), 7.92-7.91 (d, 1H), 7.62-7.60 (d, 2H), 7.43-7.39 (t, 2H), 7.35-7.32 (t, 1H), 6.35 (s, 1H), 4.00 (s, 1H). $^{13}$C-NMR (DMSO-d$_6$): δ 155.64, 153.82, 146.13, 144.27, 143.19, 140.42, 138.78, 136.25, 126.84, 125.13, 124.14, 122.77, 120.67, 120.54, 119.99, 103.74, 65.70. MS: m/z 339 (M$^+$).

6-(4'-Ethylbiphenyl-4-ylamino)quinazoline-5,8-dione [QD 392]

Quinazoline-5,8-dione (QD323, 0.050 g, 0.312 mmol), cerium (III) chloride eptahydrate (CeCl$_3$.7H$_2$O, 1.1 eq., 0.128 g, 0.343 mmol), 4-amino-4'-ethylbiphenyl (1.0 eq., 0.061 g, 0.312 mmol), and absolute ethanol (6 mL). Flash chromatography (ethyl acetate-petroleum ether=5:5) gave compound QD392 as a violet powder. Yield %: 77. Rf: 0.19 (ether petroleum:ethyl acetate=5:5). mp: 247° C. $^1$H-NMR 400 MHz (DMSO-d$_6$): δ 9.63 (s, 2H), 9.43 (s, 1H), 7.76-7.74 (d, 2H), 7.64-7.62 (d, 2H), 7.49-7.47 (d, 2H), 7.33-7.31 (d, 2H), 6.36 (s, 1H), 2.69-2.63 (m, 2H), 1.24-1.21 (t, 3H). $^{13}$C-NMR 100 MHz (DMSO-d$_6$): δ 185.78, 185.24, 167.73, 161.00, 159.01, 151.19, 148.40, 142.53, 141.91, 133.63, 132.54, 131.68, 129.33, 109.12, 33.02, 20.77. MS: m/z 355 (M$^+$).

6-(4-Cyclohexylphenylamino)quinazoline-5,8-dione [QD 393]

Quinazoline-5,8-dione (QD323, 0.050 g, 0.312 mmol), cerium (III) chloride eptahydrate (CeCl$_3$.7H$_2$O, 1.1 eq., 0.128 g, 0.343 mmol), 4-cyclohexylaniline (1.0 eq., 0.055 g, 0.312 mmol), and absolute ethanol (6 mL). Flash chromatography (ethyl acetate-petroleum ether=5:5) gave compound QD393 as a violet powder. Yield %: 53. Rf: 0.24 (ether petroleum:ethyl acetate=5:5). mp: 234° C. $^1$H-NMR (DMSO-d$_6$): δ 9.61 (s, 1H), 9.53 (s, 1H), 9.40 (s, 1H), 7.34-7.28 (m, 4H), 6.21 (s, 1H), 1.82-1.80 (m, 5H), 1.73-1.70 (d, 1H), 1.47-1.33 (m, 5H). $^{13}$C-NMR (DMSO-d$_6$): δ 180.60, 162.58, 155.59, 153.85, 145.32, 127.53, 123.91, 43.26, 38.87, 26.29, 25.53. MS: m/z 333 (M$^+$).

6-(4-(4-Methylpiperazin-1-yl)phenylamino)quinazoline-5,8-dione [QD 394]

Quinazoline-5,8-dione (QD323, 0.050 g, 0.312 mmol), cerium (III) chloride eptahydrate (CeCl$_3$.7H$_2$O, 1.1 eq., 0.128 g, 0.343 mmol), 4-(4-methylpiperazin-1-yl)aniline (1.0 eq., 0.060 g, 0.312 mmol), and absolute ethanol (6 mL). Trituration with ether petroleum and 1-2 drops of diethyl ether gave compound QD394 as a violet powder. Yield %: 41. Rf: 0.15 (ether petroleum:ethyl acetate=3:7) mp: 204-205° C. $^1$H-NMR (DMSO-d$_6$): δ 9.60 (s, 1H), 9.46 (s, 1H), 9.39 (s, 1H), 7.24-7.22 (d, 2H), 7.04-7.01 (d, 2H), 6.13 (s, 1H), 3.19-3.17 (m, 4H), 2.47 (s, 4H), 2.23 (s, 3H). MS: m/z 349 (M$^+$).

6-(4-(Pyridin-2-yl)phenylamino)quinazoline-5,8-dione [QD 395]

Quinazoline-5,8-dione (QD323, 0.075 g, 0.468 mmol), cerium (III) chloride eptahydrate (CeCl$_3$.7H$_2$O, 1.1 eq., 0.192 g, 0.515 mmol), 4-(2-pyridil)aniline (1.0 eq., 0.080 g, 0.468 mmol), and absolute ethanol (9 mL). Flash chromatography (ethyl acetate-petroleum ether=2:8) gave compound QD395 as a violet powder. Yield %: 54. Rf: 0.16 (ether petroleum:ethyl acetate=2:8) mp: 239° C. $^1$H-NMR (DMSO-d$_6$): δ 9.67 (s, 1H), 9.63 (s, 1H), 9.44 (s, 1H), 8.69-8.65 (d, 1H), 8.21-8.18 (d, 2H), 8.01-7.99 (d, 1H), 7.92-7.88 (m, 1H), 7.56-7.53 (dd, 2H), (m, 1H), 6.43 (s, 1H). MS: m/z 328 (M$^+$).

Example VII

This example describes the experimental procedures for Examples I-VI.
Cell Culture.
MiaPaCa-2, Panc-1 and BxPC-3 pancreatic cancer cell lines were obtained from the ATCC. Normal pancreatic cells HPDE and HPNE were kindly provided (Translational Oncology Program, University of Southern California, Ann Arbor, Mich.). Gemcitabine resistant cell line MiaPaCa-2-GR (gemcitabine resistant) was kindly provided (Department of Pathology, Wayne State University, Detroit, Mich.). All cell lines were cultured as monolayer and maintained in RPMI1640 supplemented with 10% fetal bovine serum (FBS) in a humidified atmosphere with 5% $CO_2$ at 37° C. MiaPaCa-2-GR culture was supplemented with 200 nM gemcitabine.

MTT Assay.

Cytotoxicity of compounds was evaluated with 3-(4,5-dimethylthiazol-2-yl)-2,5-diphenyltetrazolium bromide (MTT) assay. Cells were placed in 96-well plate at 3000-8000 cells/well. After overnight attachment, compounds were added to the wells at sequential dilutions (30 nM-10 µM for most cell lines). After 72 h treatment, MTT was added into the media to a final concentration of 300 µg/mL. Cells were incubated for 3 h at 37° C., and the insoluble formazan converted by viable cells were dissolved in 150 µL of DMSO. Absorbance at 570 nm was read by microplate reader (Molecular devices, Sunnyvale, Calif.), and inhibition of cell proliferation was calculated using the following formula: Inhibition of cell proliferation (%)=(1−$OD_{treatment}$/$OD_{control}$)×100%

ROS Detection Assay.

Cells were detached by 0.05% trypsin-EDTA, neutralized, centrifuged (1200 rpm, 5 min) and resuspended in cell culture media. Suspension were then treated with 20 µM cell permeable H2DCFDA for 30 min at 37° C. Cells were then centrifuged (1200 rpm, 5 min) and washed with cell culture media to remove excess probe. After washing, cells were placed in black-wall 384-well plate at 20,000 cells/well, incubated for 30 min and treated by compounds at designated conditions. Fluorescent signal were then read at 493 nm/523 nm on BioTek H1 plate reader for ROS detection.

Bru-Seq Analysis for Nascent RNA Synthesis.

Bru-seq analysis was performed as previously reported (Paulsen et al., 2014). Briefly, 4×10⁶ MiaPaCa-2 cells were placed in 10 cm dishes on Day 1. On Day 2, cells were treated with DMSO, QD232 or QD325 for 4 h. Bromouridine was added into the media to label newly synthesized nascent RNA in the last 30 min of treatment to a final concentration of 2 mM. Cells were then collected in TRIZOL and total RNA was isolated. Bromouridine containing RNA population was further isolated and sent for sequencing. Sequencing reads were mapped to the HG19 reference genome. Pre-ranked gene lists were generated for each treatment through ranking genes by fold changes in gene synthesis levels compared with control, and analyzed with GSEA (Broad Institute, MA) (Subramanian et al., 2005, Mootha et al., 2003)

Western Blotting.

Cells (4×10⁵) were cultured in 60 mm tissue dishes and treated with DFC compounds at designated concentrations. After treatment, cells were lysed with cell lysis buffer at 4° C. for 30 min and centrifuged (12000 rpm, 10 min, 4° C.). Protein concentrations of supernatants were measured with BCA assay (Thermo Fisher Scientific). 40 µg protein per sample was subjected to SDS-PAGE analysis. Proteins were then electro transferred to methanol activated immobilon-FL PVDF membranes (EMD Millipore, Billerica, Mass.). Membranes were blocked with 5% skim milk in TBST buffer and incubated with primary antibodies (anti-NQO1, anti-HO-1, anti-CHOP, and anti-GAPDH from Cell Signaling, anti-COXIII, anti-ACTIN and anti-GRP78 from Santa Cruz Biotechnology) 1:1000 dilutions overnight at 4° C. Membranes were then washed with TBST (10 min×3), incubated with Dylight 800-conjugated secondary antibodies (Thermo Fisher Scientific, Rockford, Ill.) 1:5000 dilutions in 5% milk for 1 h at room temperature, and washed with TBST (10 min×2) and TBS (10 min). Fluorescent signal was then scanned by Odyssey Imaging Systems (LI-COR Biosciences, Lincoln, Nebr.).

Measurement of mtDNA Content by qPCR.

To assess mtDNA content, genomic DNA was isolated with QIAamp® DNA mini kit (Qiagen, Germantown, Md.) from MiaPaCa-2 cells. The mtDNA content was evaluated by co-amplifying a DNA fragment encoding mitochondrial 12S rRNA (forward primer: 5'-TAGCCCTAAACCT-CAACAGT-3'; reverse primer: 5'-TGCGCTTACTTTGTAG CCTTCAT-3') and a DNA fragment encoding the nuclear 18S rRNA (forward primer: 5'-CCCTGCC CTTTGTACA-CACC-3'; reverse primer: 5'-GATCCGAGGGCCTCACTA-3'). (Vadrot et al., 2012) Real-time qPCR was performed on Viia7 cycler (Applied Biosystems). Amplifications were monitored and analyzed by measuring the intercalation of the fluorescent dye from Fast SYBR® Green Master Mix (Applied Biosystems). Relative mtDNA contents were calculated using 18S rRNA as gene reference.

Xenograft Studies.

MiaPaCa-2 cells (2.0×10⁶) in a 100 µL suspension of RPMI1640 was injected subcutaneously into dorsal flank of 6-week NOD/SCID mice. Tumor size was monitored twice a week through caliper measurement using the following equation: $V=d^2 \times D/2$, where d represents width and D represents length of the tumor. In study 1, mice were randomly grouped (n=5 per group) when average tumor size reached 65 mm³. Daily treatment was given at five days on two days off cycles. QD325 was given at 5 mg/kg in 100 µL vehicle (5% DMSO, 60% Propylene glycol, 35% Saline) by intraperitoneal injection. Study was concluded on Day 44 when average tumor size in the group reached 1200 mm³. Unpaired t test was performed for data analysis and p<0.05 was considered significant. For tolerance test, two mice remained on each group beyond day 44 and QD325 dose was gradually increased to 20 mg/kg until day 67. Procedures for study 2 with gemcitabine treatment are detailed in supplemental information.

Histochemical Analysis.

On necropsy, tumors, hearts, kidneys, livers, lungs, spleens and pancreases were collected, fixed in 10% neutral buffered formalin, embedded in paraffin, and sectioned. Sections (5 µM) were stained with hematoxylin and eosin to facilitate histologic examination. For Ki67 expression level, immunohistochemistry staining was performed on sections with Ki67 antibody. Embedding, sectioning and staining of samples were performed by ULAM pathology core for animal research at the University of Michigan. Representative images were taken on Olympus IX83 microscope with 20× magnification.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

The entire disclosure of each of the following scientific articles is incorporated by reference for all purposes:

ALAM, J., STEWART, D., TOUCHARD, C., BOINAPALLY, S., CHOI, A. M. & COOK, J. L. 1999. Nrf2, a Cap'n'Collar transcription factor, regulates induction of the heme oxygenase-1 gene. *J Biol Chem*, 274, 26071-8.

ALEXEYEV, M., SHOKOLENKO, I., WILSON, G. & LEDOUX, S. 2013. The maintenance of mitochondrial DNA integrity—critical analysis and update. *Cold Spring Harb Perspect Biol*, 5, a012641.

ALI, S., ALMHANNA, K., CHEN, W., PHILIP, P. A. & SARKAR, F. H. 2010. Differentially expressed miRNAs in the plasma may provide a molecular signature for aggressive pancreatic cancer. *Am J Transl Res*, 3, 28-47.

ARLT, A., SEBENS, S., KREBS, S., GEISMANN, C., GROSSMANN, M., KRUSE, M. L., SCHREIBER, S. & SCHAFER, H. 2013. Inhibition of the Nrf2 transcription factor by the alkaloid trigonelline renders pancreatic cancer cells more susceptible to apoptosis through decreased proteasomal gene expression and proteasome activity. *Oncogene*, 32, 4825-35.

CHOI, A. M. & ALAM, J. 1996. Heme oxygenase-1: function, regulation, and implication of a novel stress-inducible protein in oxidant-induced lung injury. *Am J Respir Cell Mol Biol*, 15, 9-19.

COHEN, S. J., ZALUPSKI, M. M., MODIANO, M. R., CONKLING, P., PATT, Y. Z., DAVIS, P., DORR, R. T., BOYTIM, M. L. & HERSH, E. M. 2010. A phase I study of imexon plus gemcitabine as first-line therapy for advanced pancreatic cancer. *Cancer Chemother Pharmacol*, 66, 287-94.

CONROY, T., DESSEIGNE, F., YCHOU, M., BOUCHE, O., GUIMBAUD, R., BECOUARN, Y., ADENIS, A., RAOUL, J. L., GOURGOU-BOURGADE, S., DE LA FOUCHARDIERE, C., BENNOUNA, J., BACHET, J. B., KHEMISSA-AKOUZ, F., PERE-VERGE, D., DELBALDO, C., ASSENAT, E., CHAUFFERT, B., MICHEL, P., MONTOTO-GRILLOT, C., DUCREUX, M., GROUPE TUMEURS DIGESTIVES OF, U. & INTERGROUP, P. 2011. FOLFIRINOX versus gemcitabine for metastatic pancreatic cancer. *N Engl J Med*, 364, 1817-25.

DENICOLA, G. M., KARRETH, F. A., HUMPTON, T. J., GOPINATHAN, A., WEI, C., FRESE, K, MANGAL, D., YU, K. H., YEO, C. J., CALHOUN, E. S., SCRIMIERI, F., WINTER, J. M., HRUBAN, R. H., IACOBUZIO-DONAHUE, C., KERN, S. E., BLAIR, I. A. & TUVESON, D. A. 2011. Oncogene-induced Nrf2 transcription promotes ROS detoxification and tumorigenesis. *Nature*, 475, 106-9.

DHILLON, H., CHIKARA, S. & REINDL, K. M. 2014. Piperlongumine induces pancreatic cancer cell death by enhancing reactive oxygen species and DNA damage. *Toxicol Rep*, 1, 309-318.

DINKOVA-KOSTOVA, A. T., HOLTZCLAW, W. D., COLE, R. N., ITOH, K., WAKABAYASHI, N., KATOH, Y., YAMAMOTO, M. & TALALAY, P. 2002. Direct evidence that sulfhydryl groups of Keap1 are the sensors regulating induction of phase 2 enzymes that protect against carcinogens and oxidants. *Proc Natl Acad Sci USA*, 99, 11908-13.

DINKOVA-KOSTOVA, A. T. & TALALAY, P. 2000. Persuasive evidence that quinone reductase type 1 (DT diaphorase) protects cells against the toxicity of electrophiles and reactive forms of oxygen. *Free Radic Biol Med*, 29, 231-40.

DORR, R. T., RAYMOND, M. A., LANDOWSKI, T. H., ROMAN, N. O. & FUKUSHIMA, S. 2005. Induction of apoptosis and cell cycle arrest by imexon in human pancreatic cancer cell lines. *Int J Gastrointest Cancer*, 36, 15-28.

FALKENBERG, M., LARSSON, N. G. & GUSTAFSSON, C. M. 2007. DNA replication and transcription in mammalian mitochondria. *Annu Rev Biochem*, 76, 679-99.

FRUEHAUF, J. P. & MEYSKENS, F. L., JR. 2007. Reactive oxygen species: a breath of life or death? *Clin Cancer Res*, 13, 789-94.

GULENG, G., LOVIG, T., MELING, G. I., ANDERSEN, S. N. & ROGNUM, T. O. 2005. Mitochondrial microsatellite instability in colorectal carcinomas—frequency and association with nuclear microsatellite instability. *Cancer Lett*, 219, 97-103.

HALLIWELL, B. & ARUOMA, O. I. 1991. DNA damage by oxygen-derived species. Its mechanism and measurement in mammalian systems. *FEBS Lett*, 281, 9-19.

HARDING, H. P., ZHANG, Y., BERTOLOTTI, A., ZENG, H. & RON, D. 2000. Perk is essential for translational regulation and cell survival during the unfolded protein response. *Mol Cell*, 5, 897-904.

HAYES, J. D. & MCMAHON, M. 2009. NRF2 and KEAP1 mutations: permanent activation of an adaptive response in cancer. *Trends Biochem Sci*, 34, 176-88.

HAZE, K, YOSHIDA, H., YANAGI, H., YURA, T. & MORI, K. 1999. Mammalian transcription factor ATF6 is synthesized as a transmembrane protein and activated by proteolysis in response to endoplasmic reticulum stress. *Mol Biol Cell*, 10, 3787-99.

HETZ, C. 2012. The unfolded protein response: controlling cell fate decisions under ER stress and beyond. *Nat Rev Mol Cell Biol*, 13, 89-102.

JAISWAL, A. K. 2004. Nrf2 signaling in coordinated activation of antioxidant gene expression. *Free Radic Biol Med*, 36, 1199-207.

KABEKKODU, S. P., BHAT, S., MASCARENHAS, R., MALLYA, S., BHAT, M., PANDEY, D., KUSHTAGI, P., THANGARAJ, K., GOPINATH, P. M. & SATYAMOORTHY, K. 2014. Mitochondrial DNA variation analysis in cervical cancer. *Mitochondrion*, 16, 73-82.

KIM, R., EMI, M., TANABE, K. & MURAKAMI, S. 2006. Role of the unfolded protein response in cell death. *Apoptosis*, 11, 5-13.

KONG, B., QIA, C., ERKAN, M., KLEEFF, J. & MICHALSKI, C. W. 2013. Overview on how oncogenic Kras promotes pancreatic carcinogenesis by inducing low intracellular ROS levels. *Front Physiol*, 4, 246.

LI, X., FANG, P., MAI, J., CHOI, E. T., WANG, H. & YANG, X. F. 2013. Targeting mitochondrial reactive oxygen species as novel therapy for inflammatory diseases and cancers. *J Hematol Oncol*, 6, 19.

LIEVRE, A., CHAPUSOT, C., BOUVIER, A. M., ZINZINDOHOUE, F., PIARD, F., ROIGNOT, P., ARNOULD, L., BEAUNE, P., FAIVRE, J. & LAURENT-PUIG, P. 2005. Clinical value of mitochondrial mutations in colorectal cancer. *J Clin Oncol*, 23, 3517-25.

LISTER, A., NEDJADI, T., KITTERINGHAM, N. R., CAMPBELL, F., COSTELLO, E., LLOYD, B., COPPLE, I. M., WILLIAMS, S., OWEN, A., NEOPTOLEMOS, J. P., GOLDRING, C. E. & PARK, B. K. 2011. Nrf2 is overexpressed in pancreatic cancer: implications for cell proliferation and therapy. *Mol Cancer*, 10, 37.

MALHOTRA, J. D. & KAUFMAN, R. J. 2007. Endoplasmic reticulum stress and oxidative stress: a vicious cycle or a double-edged sword? *Antioxid Redox Signal*, 9, 2277-93.

MONTOYA, J., GAINES, G. L. & ATTARDI, G. 1983. The pattern of transcription of the human mitochondrial rRNA genes reveals two overlapping transcription units. *Cell*, 34, 151-9.

MOON, E. J. & GIACCIA, A. 2014. Dual roles of NRF2 in tumor prevention and progression: Possible implications in cancer treatment. *Free Radic Biol Med*.

MOOTHA, V. K., LINDGREN, C. M., ERIKSSON, K. F., SUBRAMANIAN, A., SIHAG, S., LEHAR, J., PUIG-SERVER, P., CARLSSON, E., RIDDERSTRALE, M., LAURILA, E., HOUSTIS, N., DALY, M. J., PATTERSON, N., MESIROV, J. P., GOLUB, T. R., TAMAYO, P., SPIEGELMAN, B., LANDER, E. S., HIRSCHHORN, J. N., ALTSHULER, D. & GROOP, L. C. 2003. PGC-1alpha-responsive genes involved in oxidative phosphorylation are coordinately downregulated in human diabetes. *Nat Genet*, 34, 267-73.

NA, H. K. & SURH, Y. J. 2014. Oncogenic potential of Nrf2 and its principal target protein heme oxygenase-1. *Free Radic Biol Med*, 67, 353-65.

NIOI, P., MCMAHON, M., ITOH, K., YAMAMOTO, M. & HAYES, J. D. 2003. Identification of a novel Nrf2-regulated antioxidant response element (ARE) in the mouse NAD(P)H:quinone oxidoreductase 1 gene: reassessment of the ARE consensus sequence. *Biochem J*, 374, 337-48.

NISHITOH, H. 2012. CHOP is a multifunctional transcription factor in the ER stress response. *J Biochem*, 151, 217-9.

OJALA, D., MONTOYA, J. & ATTARDI, G. 1981. tRNA punctuation model of RNA processing in human mitochondria. *Nature*, 290, 470-4.

OUYANG, H., MOU, L., LUK, C., LIU, N., KARASKOVA, J., SQUIRE, J. & TSAO, M. S. 2000. Immortal human pancreatic duct epithelial cell lines with near normal genotype and phenotype. *Am J Pathol*, 157, 1623-31.

OYADOMARI, S. & MORI, M. 2004. Roles of CHOP/GADD153 in endoplasmic reticulum stress. *Cell Death Differ*, 11, 381-9.

PATHANIA, D., KUANG, Y., SECHI, M. & NEAMATI, N. 2015. Mechanisms underlying the cytotoxicity of a novel quinazolinedione-based redox modulator, QD232, in pancreatic cancer cells. *Br J Pharmacol*, 172, 50-63.

PATHANIA, D., SECHI, M., PALOMBA, M., SANNA, V., BERRETTINI, F., SIAS, A., TAHERI, L. & NEAMATI, N. 2014. Design and discovery of novel quinazolinedione-based redox modulators as therapies for pancreatic cancer. *Biochim Biophys Acta*, 1840, 332-43.

PAULSEN, M. T., VELOSO, A., PRASAD, J., BEDI, K., LJUNGMAN, E. A., MAGNUSON, B., WILSON, T. E. & LJUNGMAN, M. 2014. Use of Bru-Seq and BruChase-Seq for genome-wide assessment of the synthesis and stability of RNA. *Methods*, 67, 45-54.

PAULSEN, M. T., VELOSO, A., PRASAD, J., BEDI, K., LJUNGMAN, E. A., TSAN, Y. C., CHANG, C. W., TARRIER, B., WASHBURN, J. G., LYONS, R., ROBINSON, D. R., KUMAR-SINHA, C., WILSON, T. E. & LJUNGMAN, M. 2013. Coordinated regulation of synthesis and stability of RNA during the acute TNF-induced proinflammatory response. *Proc Natl Acad Sci USA*, 110, 2240-5.

PELICANO, H., CARNEY, D. & HUANG, P. 2004. ROS stress in cancer cells and therapeutic implications. *Drug Resist Updat*, 7, 97-110.

ROSS, D., KEPA, J. K., WINSKI, S. L., BEALL, H. D., ANWAR, A. & SIEGEL, D. 2000. NAD(P)H:quinone oxidoreductase 1 (NQO1): chemoprotection, bioactivation, gene regulation and genetic polymorphisms. *Chem Biol Interact*, 129, 77-97.

RYAN, D. P., HONG, T. S. & BARDEESY, N. 2014. Pancreatic adenocarcinoma. *N Engl J Med*, 371, 1039-49.

SABHARWAL, S. S. & SCHUMACKER, P. T. 2014. Mitochondrial ROS in cancer: initiators, amplifiers or an Achilles' heel? *Nat Rev Cancer*, 14, 709-21.

SALAZAR, J. J. & VAN HOUTEN, B. 1997. Preferential mitochondrial DNA injury caused by glucose oxidase as a steady generator of hydrogen peroxide in human fibroblasts. *Mutat Res*, 385, 139-49.

SHAMU, C. E. & WALTER, P. 1996. Oligomerization and phosphorylation of the Ire1p kinase during intracellular signaling from the endoplasmic reticulum to the nucleus. *EMBO J*, 15, 3028-39.

SHOKOLENKO, I. N., WILSON, G. L. & ALEXEYEV, M. F. 2013. Persistent damage induces mitochondrial DNA degradation. *DNA Repair* (Amst), 12, 488-99.

SIEGEL, R., MA, J., ZOU, Z. & JEMAL, A. 2014. Cancer statistics, 2014. *CA Cancer J Clin*, 64, 9-29.

SUBRAMANIAN, A., TAMAYO, P., MOOTHA, V. K., MUKHERJEE, S., EBERT, B. L., GILLETTE, M. A., PAULOVICH, A., POMEROY, S. L., GOLUB, T. R., LANDER, E. S. & MESIROV, J. P. 2005. Gene set enrichment analysis: a knowledge-based approach for interpreting genome-wide expression profiles. *Proc Natl Acad Sci USA*, 102, 15545-50.

SUZUKI, M., TOYOOKA, S., MIYAJIMA, K., IIZASA, T., FUJISAWA, T., BEKELE, N. B. & GAZDAR, A. F. 2003. Alterations in the mitochondrial displacement loop in lung cancers. *Clin Cancer Res*, 9, 5636-41.

VADROT, N., GHANEM, S., BRAUT, F., GAVRILESCU, L., PILARD, N., MANSOURI, A., MOREAU, R. & REYL-DESMARS, F. 2012. Mitochondrial DNA maintenance is regulated in human hepatoma cells by glycogen synthase kinase 3beta and p53 in response to tumor necrosis factor alpha. *PLoS One*, 7, e40879.

VERFAILLIE, T., GARG, A. D. & AGOSTINIS, P. 2013. Targeting ER stress induced apoptosis and inflammation in cancer. *Cancer Lett*, 332, 249-64.

VON HOFF, D. D., ERVIN, T., ARENA, F. P., CHIOREAN, E. G., INFANTE, J., MOORE, M., SEAY, T., TJULANDIN, S. A., MA, W. W., SALEH, M. N., HARRIS, M., RENI, M., DOWDEN, S., LAHERU, D., BAHARY, N., RAMANATHAN, R. K., TABERNERO, J., HIDALGO, M., GOLDSTEIN, D., VAN CUTSEM, E., WEI, X., IGLESIAS, J. & RENSCHLER, M. F. 2013. Increased survival in pancreatic cancer with nab-paclitaxel plus gemcitabine. *N Engl J Med*, 369, 1691-703.

WHEELHOUSE, N. M., LAI, P. B., WIGMORE, S. J., ROSS, J. A. & HARRISON, D. J. 2005. Mitochondrial D-loop mutations and deletion profiles of cancerous and noncancerous liver tissue in hepatitis B virus-infected liver. *Br J Cancer*, 92, 1268-72.

YAKES, F. M. & VAN HOUTEN, B. 1997. Mitochondrial DNA damage is more extensive and persists longer than nuclear DNA damage in human cells following oxidative stress. *Proc Natl Acad Sci USA*, 94, 514-9.

YE, K., LU, J., MA, F., KEINAN, A. & GU, Z. 2014. Extensive pathogenicity of mitochondrial heteroplasmy in healthy human individuals. *Proc Natl Acad Sci USA*, 111, 10654-9.

ZHANG, D. D. & HANNINK, M. 2003. Distinct cysteine residues in Keap1 are required for Keap1-dependent ubiquitination of Nrf2 and for stabilization of Nrf2 by chemopreventive agents and oxidative stress. *Mol Cell Biol*, 23, 8137-51.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:
1. A compound having Formula I:

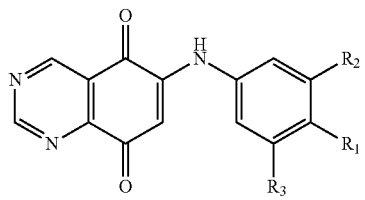

(Formula I)

or Formula II:

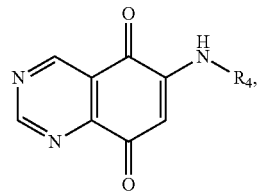

(Formula II)

including pharmaceutically acceptable salts thereof; wherein $R_1$, $R_2$, $R_3$, and $R_4$, independently include any chemical moiety that permits the resulting compound to induce ROS and inhibit mitochondrial activity within cancer cells, wherein $R_1$ is selected from the group consisting of: Hydrogen,

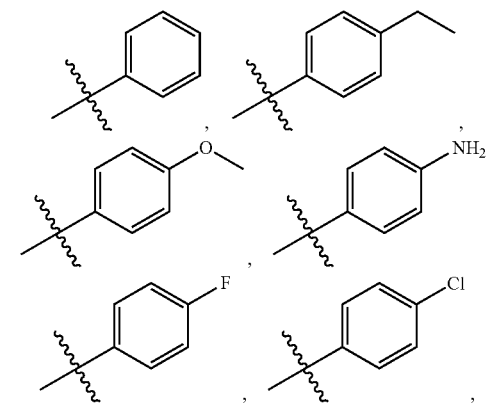

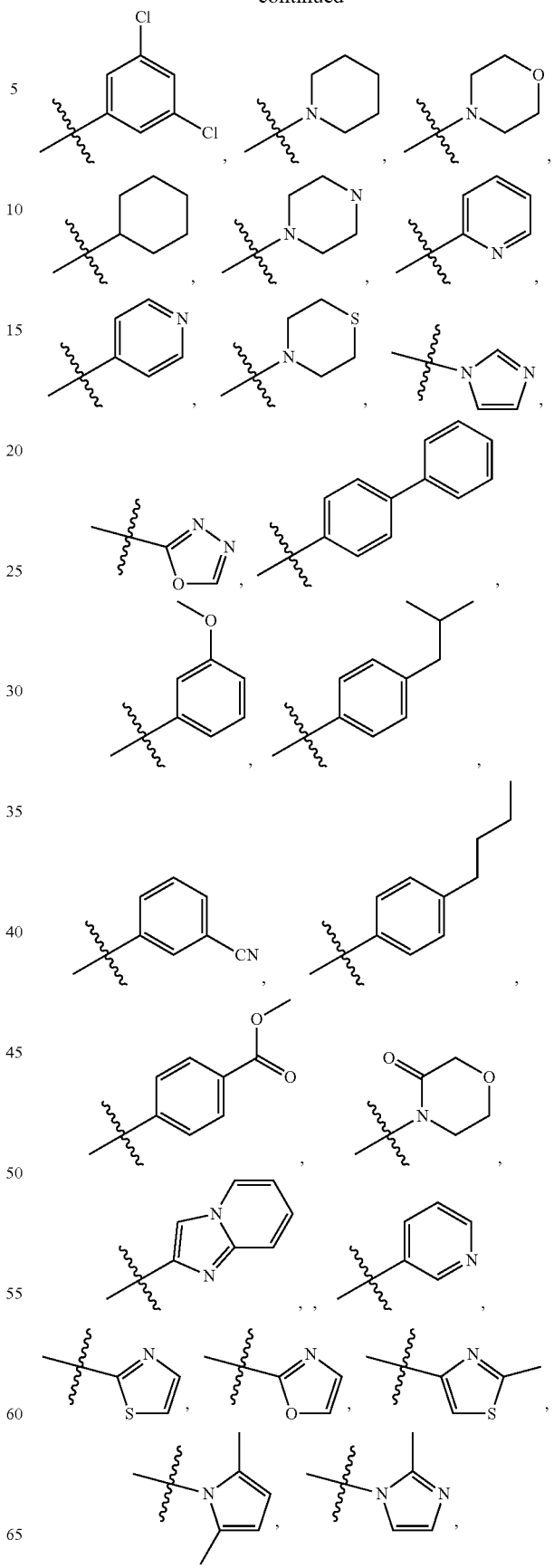

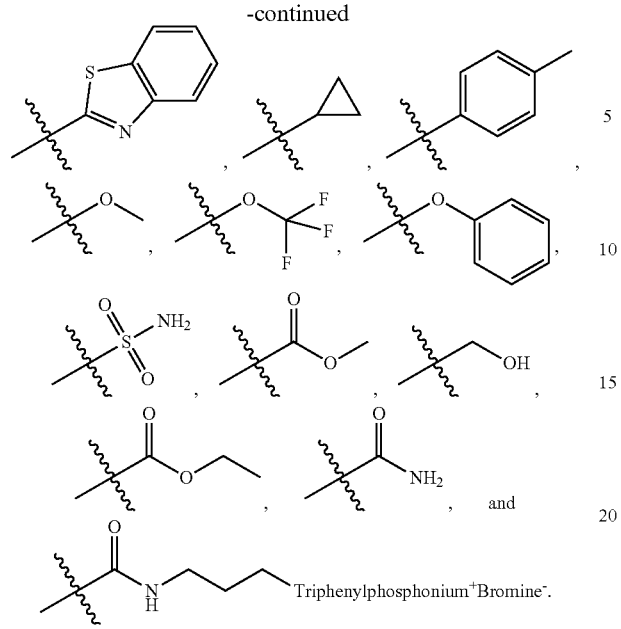
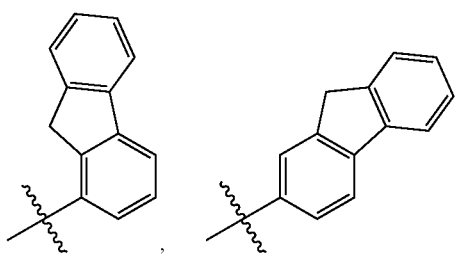
wherein R₂ is selected from the group consisting of Hydrogen,
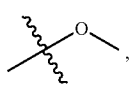 [SMILES: *OC]
Fluorine, and
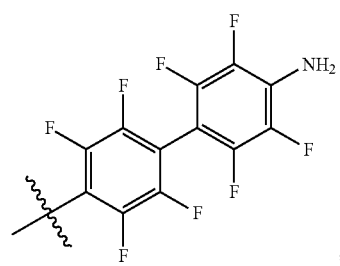
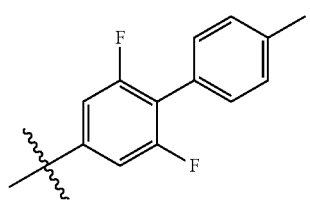
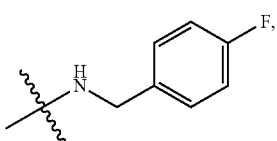
wherein R₃ is selected from the group consisting of Hydrogen,
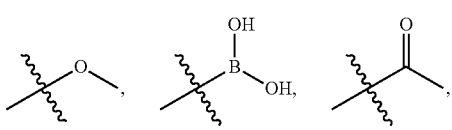
Fluorine, and
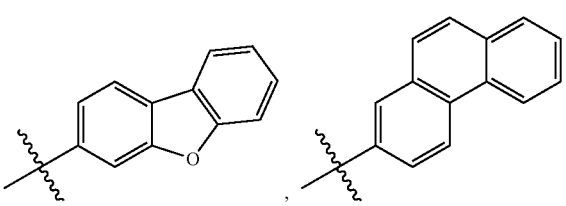
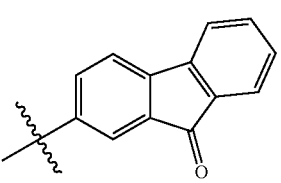
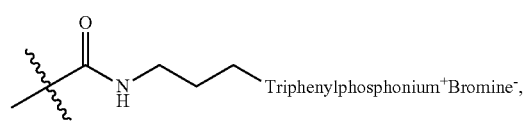
and
wherein R₄ is selected from the group consisting of Hydrogen,
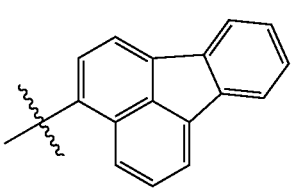

89
-continued
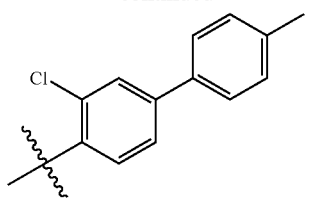
,
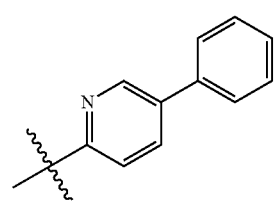
,
90
-continued
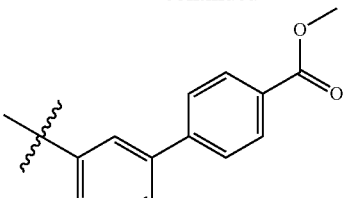
, and
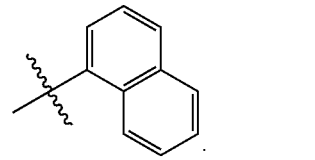
.
2. The compound of claim 1, wherein said compound is selected from the group consisting of:
(325)
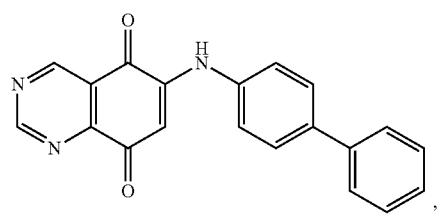
,
(356)
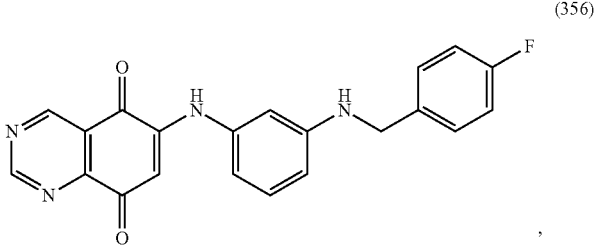
,
(335)
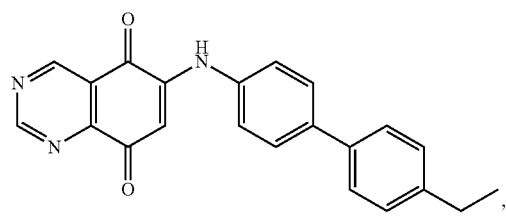
,
(336)
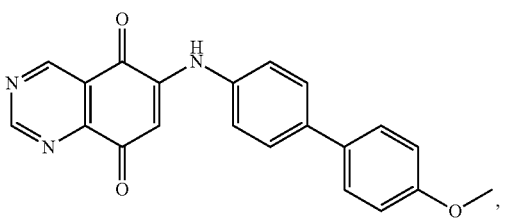
,
(337)
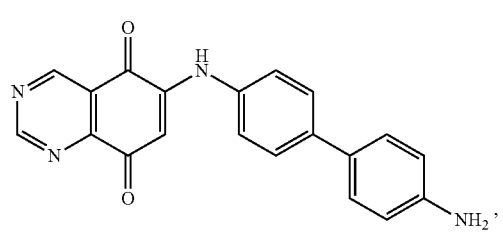
,
(334)
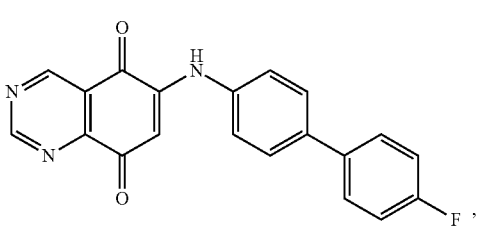
,
(338)
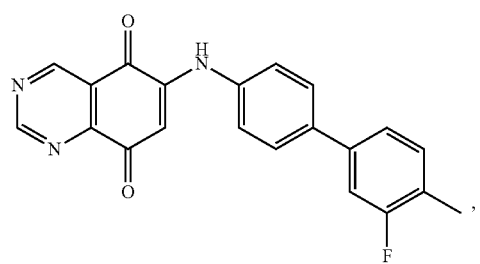
,
(326)
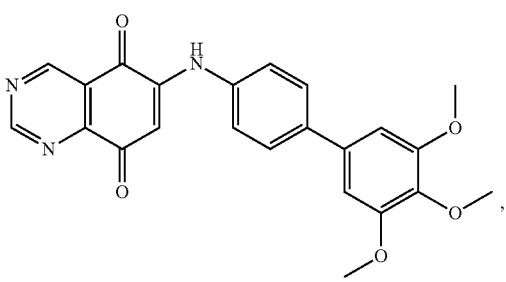
, (353) 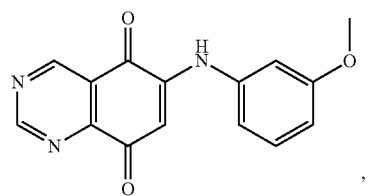
(354) 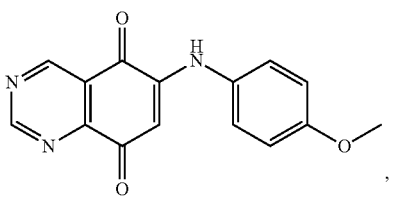
(355) 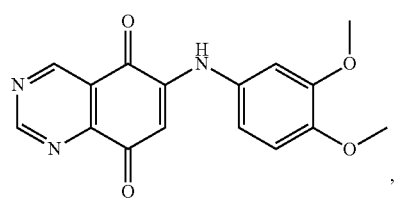
(357) 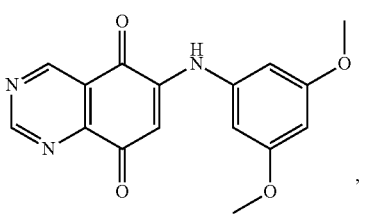
(327) 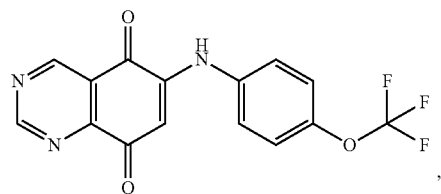
(324) 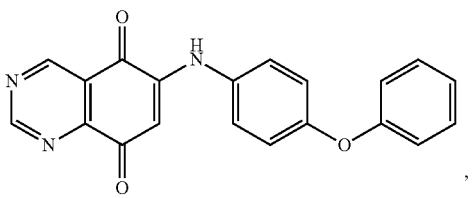
(328) 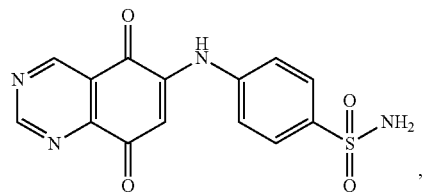
(333) 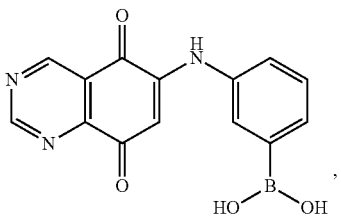
(331) 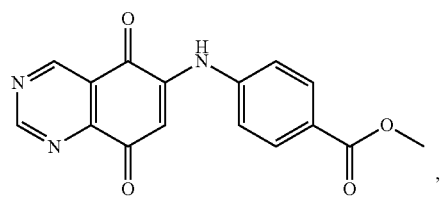
(329) 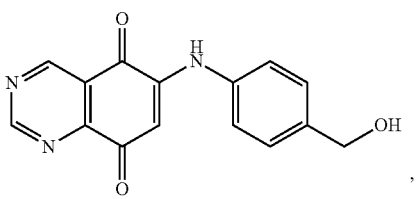
(332) 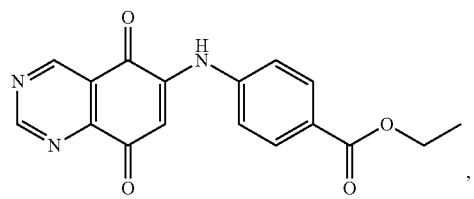
(330) 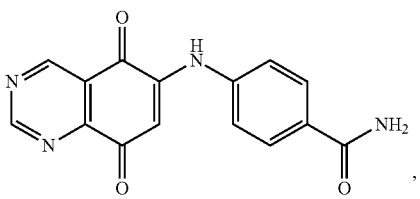
(340) 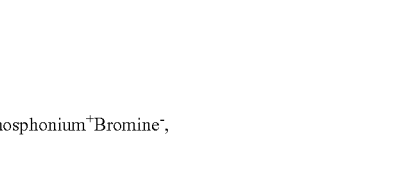
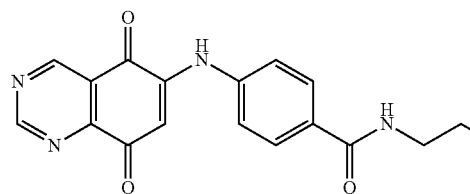

-continued
(359)
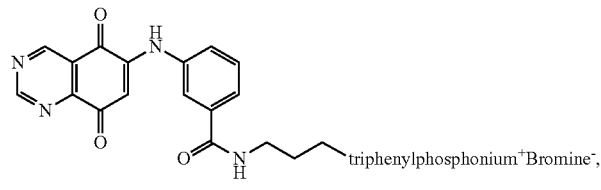
(396)
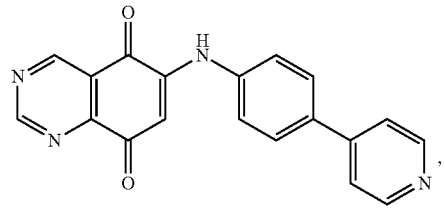
(397)
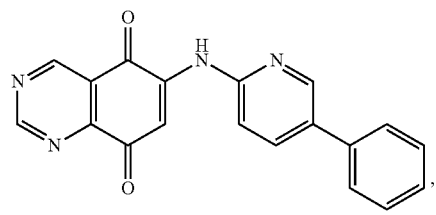
(398)
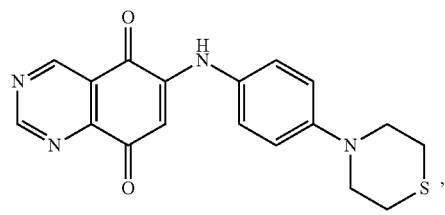
(399)
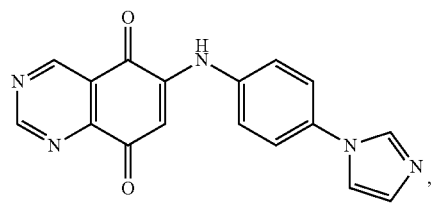
(400)
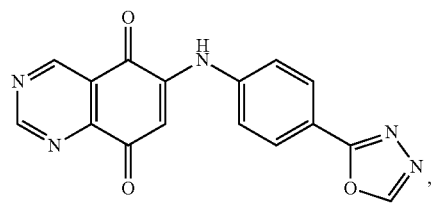
(401)
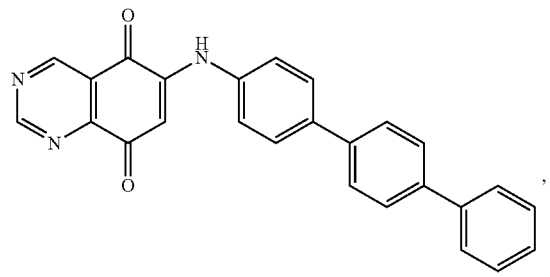
(402)
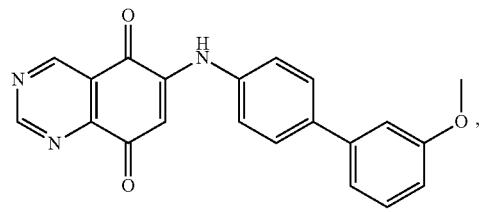
(403)
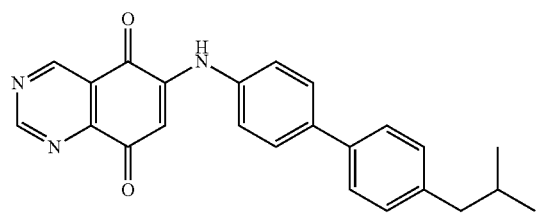
(404)
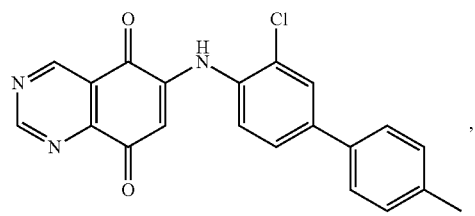
(405)
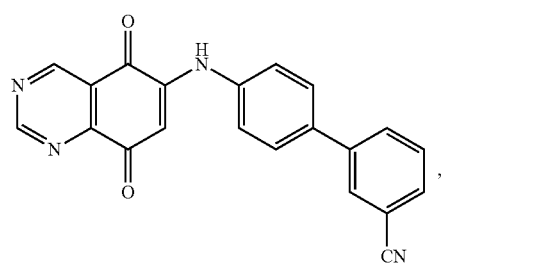
(406)
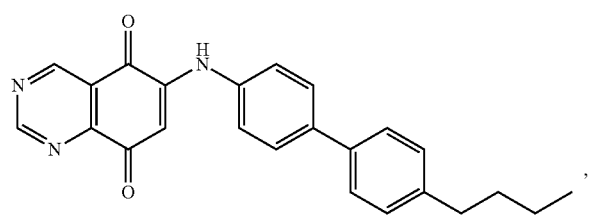

(407) 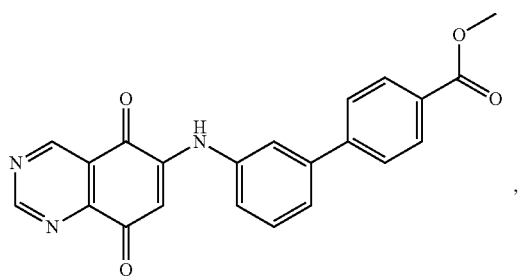
(408) 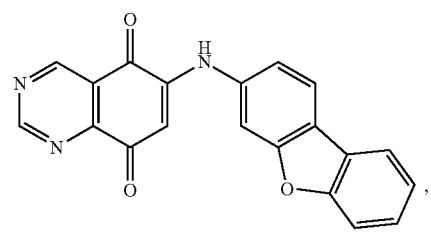
(409) 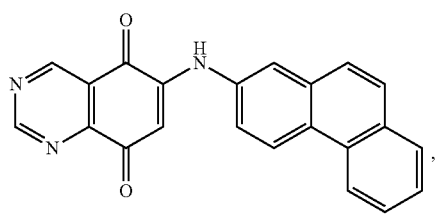
(410) 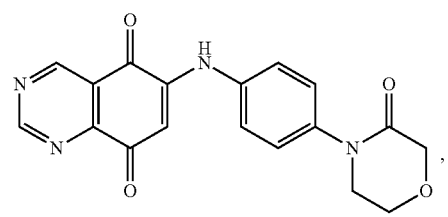
(411) 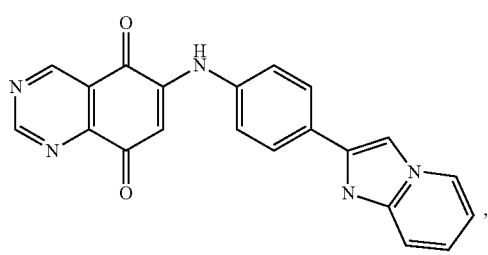
(412) 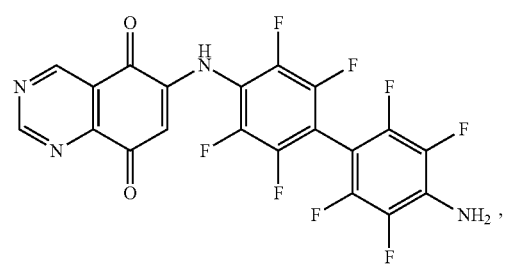
(413) 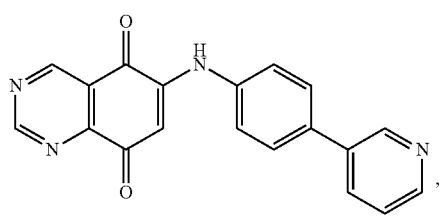
(414) 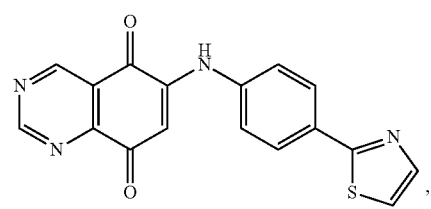
(415) 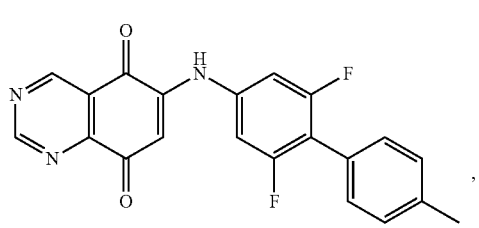
(416) 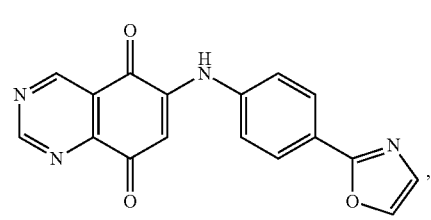
(417) 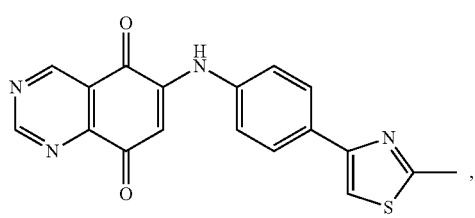
(418) 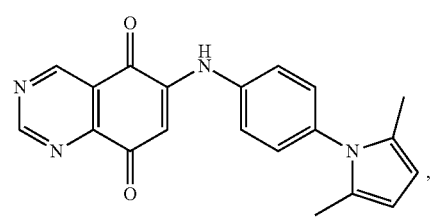

(419)
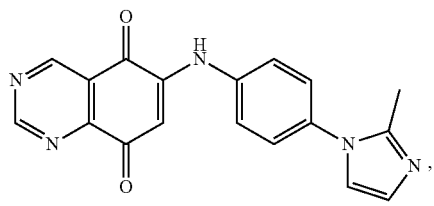

(420)
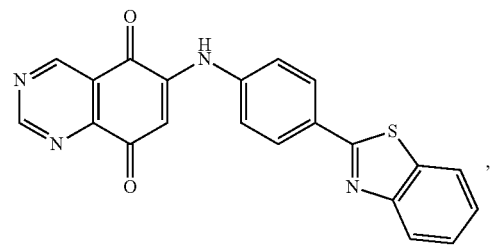

(421)
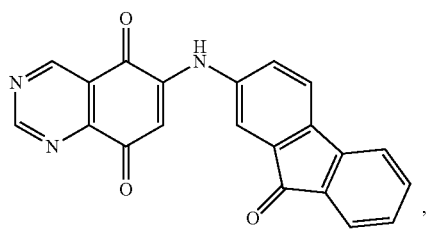

(422)

(423)
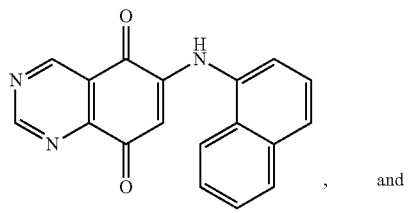
and (424)

or a pharmaceutically acceptable salt thereof.

3. A pharmaceutical composition comprising a compound of claim 1.

4. A method of treating pancreatic cancer and/or PDAC in a patient comprising administering to said patient a therapeutically effective amount of the pharmaceutical composition of claim 3.

5. The method of claim 4, wherein said patient is a human patient.

6. The method of claim 4 further comprising administering to said patient one or more anticancer agents.

7. The method of claim 6 wherein said anticancer agent is a chemotherapeutic agent.

8. The method of claim 6 wherein said anticancer agent is radiation therapy.

9. A kit comprising a compound of claim 1, one or more anticancer agents, wherein said compound is to be administered together with one or more anticancer agents, and instructions for administering said compound to a patient having a hyperproliferative disease, wherein said hyperproliferative disease is cancer, wherein said cancer is pancreatic cancer and/or PDAC.

* * * * *